US010562941B2

(12) United States Patent
Tweten

(10) Patent No.: US 10,562,941 B2
(45) Date of Patent: Feb. 18, 2020

(54) PNEUMOLYSIN MUTANTS AND METHODS OF USE THEREOF

(71) Applicant: The Board of Regents of the University of Oklahoma, Norman, OK (US)

(72) Inventor: Rodney K. Tweten, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 124 days.

(21) Appl. No.: 15/527,919

(22) PCT Filed: Nov. 20, 2015

(86) PCT No.: PCT/US2015/061859
§ 371 (c)(1),
(2) Date: May 18, 2017

(87) PCT Pub. No.: WO2016/081839
PCT Pub. Date: May 26, 2016

(65) Prior Publication Data

US 2018/0312552 A1 Nov. 1, 2018

Related U.S. Application Data

(60) Provisional application No. 62/082,848, filed on Nov. 21, 2014.

(51) Int. Cl.
*C07K 14/315* (2006.01)
*A61K 39/09* (2006.01)
*A61K 38/00* (2006.01)
*A61K 39/00* (2006.01)

(52) U.S. Cl.
CPC ........ *C07K 14/3156* (2013.01); *A61K 39/092* (2013.01); *A61K 38/00* (2013.01); *A61K 39/00* (2013.01); *A61K 2039/55505* (2013.01)

(58) Field of Classification Search
None
See application file for complete search history.

(56) References Cited

U.S. PATENT DOCUMENTS

| | | | |
|---|---|---|---|
| 4,686,102 | A | 8/1987 | Ridchey et al. |
| 5,565,204 | A | 10/1996 | Kuo et al. |
| 6,224,880 | B1 | 5/2001 | Chan et al. |
| 6,632,441 | B2 | 10/2003 | Schlievert et al. |
| 6,716,432 | B1 | 4/2004 | Paton et al. |
| 6,764,686 | B2 | 7/2004 | Minetti et al. |
| 6,887,480 | B1 | 5/2005 | Adamou et al. |
| 6,903,184 | B1 | 6/2005 | Ades et al. |
| 7,045,132 | B2 | 5/2006 | Sampson et al. |
| 7,122,194 | B2 | 10/2006 | Johnson et al. |
| 7,125,548 | B2 | 10/2006 | Smith |
| 7,132,107 | B2 | 11/2006 | Adamou et al. |
| 7,217,791 | B2 | 5/2007 | Chen et al. |
| 7,262,024 | B2 | 8/2007 | Hamel et al. |
| 7,820,789 | B2 | 10/2010 | Kirkham et al. |
| 8,128,939 | B2 | 3/2012 | Tweten |
| 8,758,766 | B2 | 6/2014 | Oloo et al. |
| 9,181,308 | B2 | 11/2015 | Tuomanen et al. |
| 9,844,587 | B2 | 12/2017 | Tuomanen et al. |
| 2009/0285846 | A1 | 11/2009 | Tweten |
| 2010/0166795 | A1 | 7/2010 | Mitchell et al. |
| 2014/0023674 | A1 | 1/2014 | Tuomanen et al. |
| 2014/0341942 | A1 | 11/2014 | Oloo et al. |
| 2018/0078633 | A1 | 3/2018 | Tuomanen et al. |

FOREIGN PATENT DOCUMENTS

| | | |
|---|---|---|
| WO | 1990006951 | 6/1990 |
| WO | 2005076696 | 8/2005 |
| WO | 2005/108419 A1 | 11/2005 |
| WO | 2005/108580 A1 | 11/2005 |

OTHER PUBLICATIONS

Burgess et al. (J. Cell Biol. 111:2129-2138, 1990).*
Lazar et al. (Mol. Cell. Biol., 8:1247-1252, 1988).*
EP Application No. 15861711.8; Rodney K. Tweten, filed Jul. 5, 2011; Extended European Search Report dated May 4, 2018.
International Search Report, dated Apr. 1, 2016, in PCT/US2015/061859, filed Nov. 20, 2015.
Written Opinion of the International Searching Authority, dated Apr. 1, 2016, in PCT/US2015/061859, filed Nov. 20, 2015.
Harvey, et al.; "The Impact of Pneumolysin on the Macrophage Response to *Streptococcus pneumoniae* is Strain-Dependent," PLOS One (2014) vol. 9, No. 8, pp. 1-9.
Walker, et al.; "Molecular Cloning, Characterization, and Complete Nucleotide Sequence of the Gene for Pneumolysin, the Sulfhydryl-Activated Toxin of *Streptococcus pneumoniae*," Infection and Immunity (1987),vol. 55, No. 5, pp. 1184-1189.
Anonymous: "Prevention of Pneumococcal Disease: Recommendations of the Advisory Committee on Immunication Practices (ACIP)," Morbidity and Mortality Weekly Report-Recommendations and Reports (1997), vol. 46, 20 pages.
Alexander, et al.; "Amino Acid Changes Affecting the Activity of Pneumolysin Alter the Behavior of Pneumococci in Pneumonia," Microbial Pathogenesis, Academic Press Limited, New York, NY (1998), vol. 24, No. 3, pp. 167-174.

(Continued)

*Primary Examiner* — Brian Gangle
(74) *Attorney, Agent, or Firm* — Dunlap Codding, P.C.

(57) ABSTRACT

The present disclosure provides, in various embodiments, immunogenic mutants of cholesterol-dependent cytolysins, such as pneumolysin, which have reduced hemolytic activity and reduced pore-forming activity in comparison to their wild type protein. The present disclosure also provides, in various embodiments, nucleic acids which encode such mutants, and methods of the use of such mutants.

19 Claims, 9 Drawing Sheets
(2 of 9 Drawing Sheet(s) Filed in Color)
Specification includes a Sequence Listing.

(56) References Cited

OTHER PUBLICATIONS

Berry, et al.; "Effect of Defined Point Mutations in the Pneumolysin Gene on the Virulence of *Streptococcus pneumoniae*," Infection and Immunity (1995), vol. 63, No. 5, pp. 1969-1974.
Boslego, et al.; "Vaccines and Immunotherapy," Pergaman Press (19911) Gonorrhea Vaccines, Chapter 17, pp. 211-223.
Bowie, et al.; "Deciphering the Message in Protein Sequences: Tolerance to Amino Acid Substitutions," Science (1990), vol. 257, pp. 1306-1310.
Ellis; "Plotkin & Mortimer—Vaccines," W.B. Saunders Company (1988), "New Technologies for Making Vaccines," Chapter 29, pp. 568-575.
Greenspan, et al.; "Defining Epitopes: It's Not as Easy as It Seems," Nature Biotechnology (1999), vol. 17, pp. 936-937.
Kirkham, et al.; 4th International Symposium on Pneumococcal and Pneumococcal Diseases, Helinski, Finland (online) www.congrer.fi/isppd-4/immages/abstract/pdf.
EP08827230.7; Rodney K. Tweten; filed Nov. 11, 2009; European Search Report dated Dec. 30, 2010.
EP11174235.9; Rodney K. Tweten; filed Jul. 15, 2011; European Search Report dated Sep. 22, 2011.
Kirkham, et al., Immunology 113(s1):2, Nov. 26, 2004, Abstract.
Kirkham, et al., "Construction and Immunological Characterization of a Novel Nontoxic Protective Pneumolysin Mutant for Use in Future Pneumococcal Vaccines Journal," (2006), vol. 74, No. 1, pp. 586-593.
Ramachandran, et al., "Structural Insights into the Membrane-Anchoring Mechanism of a Cholesterol-Dependent Cytolysin," Nat. Struct. Biol., (2002), vol. 9, pp. 823-827.
Soltani, et al., "Specific Protein-Membrane Contacts are Required for Prepore and Pore Assembly by a Cholesterol-Dependent Cytolysin," J. Biol. Chem. (2007), vol. 282, No. 21, pp. 15709-15716.
Soltani, et al., "Structural Elements of the Cholesterol-Dependent Cytolysins that are Responsible for their Cholesterol-Sensitive Membrane Interactions," PNAS, (2007), vol. 104, No. 51, pp. 20226-20231.
Tweten, "MiniReview: Cholesterol-Dependent Cytolysins, a Family of Versatile Pore-Forming Toxins," Infection and Immunity, (2005), vol. 73, No. 10, pp. 6199-6209.
AU Application No. 2008287286; Rodney K. Tweten, filed Nov. 11, 2009, First Examination Report dated Jun. 5, 2012.
CA Application No. 2,683,748; Rodney K. Tweten, filed Oct. 13, 2009; First Office Action dated Jun. 5, 2014.
EP Application No. 11174235.9; Rodney K. Tweten; filed Jul. 5, 2011; Extended European Search Report dated Jan. 13, 2012.
International Search, dated Apr. 9, 2009 in PCT/US08/60250, filed Apr. 14, 2008.
Written Opinion of the International Searching Authority, dated Apr. 9, 2009 in PCT/US08/60250, filed Apr. 14, 2008.
Shatursky, et al.; "The Mechanism of Membrane Insertion for a Cholesterol-Dependent Cytolysin: A Novel Paradigm for Pore-Forming Toxins," Cell (1999) vol. 99, pp. 293-299.
EP Application No. 11174235.9; Rodney K. Tweten, filed Jul. 5, 2011; Examination Report dated Apr. 16, 2013.
U.S. Appl. No. 12/102,696; Rodney K. Tweten, filed Apr. 14, 2008; Office Action dated Nov. 13, 2009.
U.S. Appl. No. 12/102,696; Rodney K. Tweten, filed Apr. 14, 2008; Response to Office Action dated Dec. 11, 2009.
U.S. Appl. No. 12/102,696; Rodney K. Tweten, filed Apr. 14, 2008; Office Action dated Jul. 13, 2010.
U.S. Appl. No. 12/102,696; Rodney K. Tweten, filed Apr. 14, 2008; Response to Office Action dated Jan. 11, 2011.
U.S. Appl. No. 12/102,696; Rodney K. Tweten, filed Apr. 14, 2008; Final Office Action dated Mar. 31, 2011.
U.S. Appl. No. 12/102,696; Rodney K. Tweten, filed Apr. 14, 2008; Amendment and Response to Final Office Action dated Jul. 27, 2011.
U.S. Appl. No. 12/102,696; Rodney K. Tweten, filed Apr. 14, 2008; Advisory Action dated Sep. 14, 2011.
U.S. Appl. No. 12/102,696; Rodney K. Tweten, filed Apr. 14, 2008; Request for Continued Examination dated Sep. 29, 2011.
U.S. Appl. No. 12/102,696; Rodney K. Tweten, filed Apr. 14, 2008; Notice of Allowance dated Oct. 27, 2011.
U.S. Appl. No. 13/401,460; Rodney K. Tweten, filed Feb. 12, 2012; Office Action dated Nov. 10, 2014.
U.S. Appl. No. 13/401,460; Rodney K. Tweten, filed Feb. 12, 2012; Response to Office Action dated Jan. 12, 2015.
U.S. Appl. No. 13/401,460; Rodney K. Tweten, filed Feb. 12, 2012; Office Action dated Jan. 26, 2015.
U.S. Appl. No. 13/401,460; Rodney K. Tweten, filed Feb. 12, 2012; Amendment and Response to Office Action dated May 21, 2015.
U.S. Appl. No. 13/401,460; Rodney K. Tweten, filed Feb. 12, 2012; Notice of Allowance dated Sep. 13, 2015.
AU Application No. 2008287286; Rodney K. Tweten, filed Nov. 11, 2009; Response to Examination Report dated Sep. 18, 2013.
AU Application No. 2008287286; Rodney K. Tweten, filed Nov. 11, 2009; Notice of Acceptance dated Sep. 26, 2013.
CA Application No. 2,683,748; Rodney K. Tweten, filed Oct. 13, 2009; Response to Examiner's Report dated Dec. 3, 2014.
CA Application No. 2,683,748; Rodney K. Tweten, filed Oct. 13, 2009; Notice of Allowance dated Aug. 6, 2015.
EP Application No. 111742359; Rodney K. Tweten, filed Jul. 5, 2011; European Search Report dated Jan. 13, 2012.
EP Application No. 111742359; Rodney K. Tweten, filed Jul. 5, 2011; Response to Written Opinion dated Aug. 10, 2012.
EP Application No. 111742359; Rodney K. Tweten, filed Jul. 5, 2011; Reply to Examination Report dated Jul. 26, 2013.
EP Application No. 111742359; Rodney K. Tweten, filed Jul. 5, 2011; Examination Report dated Dec. 13, 2013.
EP Application No. 111742359; Rodney K. Tweten, filed Jul. 5, 2011; Reply to Examination Report dated Apr. 8, 2014.
EP Application No. 111742359; Rodney K. Tweten, filed Jul. 5, 2011; Notice of Allowance dated May 22, 2014.
J. C. Paton, et al., Activation of Human Complement by the Pneumococcal Toxin Pneumolysin, Infection and Immunity (1984) 43:1085-1087.
F. D. Saunders, et al., Pneumolysin, the Thiol-Activated Toxin of *Streptococcus pneumoniae*, Does Not Require a Thiol Group for In Vitro Activity, Infection and Immunity (1989) 57:2547:2552.
T. J. Mitchell, et al., Complement Activation and Antibody Binding by Pneumolysin via a Region of the Toxin Homologous to a Human Acute-Phase Protein, Molecular Microbiology (1991) 5:1883-1888.

* cited by examiner

```
Cereolysin      M--------- ---------- ---------- ---------- ---------- ---------- ---------- 1
Anthrolysin     MI-------- ---------- ---------- ---------- ---------- ---------- ---------- 2
Thuringiolysin  MI-------- ---------- ---------- ---------- ---------- ---------- ---------- 2
Perfringolysin  MI-------- ---------- ---------- ---------- ---------- ---------- ---------- 2
Alveolysin      M--------- ---------- ---------- ---------- ---------- ---------- ---------- 1
Caniolysin      MK-------- ---------- ---------- ---------- ---------- ---------- ---------- 2
Equisimilysin   M--------- ---------- ---------- ---------- ---------- ---------- ---------- 1
Streptolysin O  M--------- ---------- ---------- ---------- ---------- ---------- ---------- 1
Novyiolysin     MK-------- ---------- ---------- ---------- ---------- ---------- ---------- 2
Tetanolysin     MN-------- ---------- ---------- ---------- ---------- ---------- ---------- 2
Ivanolysin      M--------- ---------- ---------- ---------- ---------- ---------- ---------- 1
Listeriolysin   M--------- ---------- ---------- ---------- ---------- ---------- ---------- 1
Seeligeriolysin M--------- ---------- ---------- ---------- ---------- ---------- ---------- 1
Suilysin        MR-------- ---------- ---------- ---------- ---------- ---------- ---------- 2
Pneumolysin     MA-------- ---------- ---------- ---------- ---------- ---------- ---------- 2
Mitilysin (PLY) ma-------- ---------- ---------- ---------- ---------- ---------- ---------- 2
Intermedilysin  MK-------- ---------- ---------- ------TKQ- ---------- ---------- ---------- 5
Viridanolysin   MNQEKRLHRF VKKCGLGVCS AVVAAFLLNA QGVALATEQG NRPVETENIA RGKQASQSST AYGGAATRAV 70
Pyolysin        MKR------- ---------- ---------- ---------- ---------- ---------- ---------- 3

Cereolysin      ---------- ---------- ---------- ---------- --NIKKNTKR RKFLACLLVS LCTINYSSIS 29
Anthrolysin     ---------- ---------- ---------- ---------- FLNIKKNTKR RKFLACLLVS LCTIHYSSIS 32
Thuringiolysin  ---------- ---------- ---------- ---------- FLNIKKNGKR RKFLTCVLVS LCTLNYSSTS 32
Perfringolysin  ---------- ---------- ---------- ---------- ------RFKK TKLIASIAMA LCLFSQPVIS 26
Alveolysin      ---------- ---------- ---------- ---------- -KKKSNHLKG RKVLVSLLVS LQVFAFASIS 30
Caniolysin      ---------- ---------- ---------- ---------- DMSNKKIFKK YSRVAGLLTA ALIVGNLVTA 32
Equisimilysin   ---------- ---------- ---------- ---------- --SNKKIFKK YSRVAGLLTA ALIVGNLVTA 29
Streptolysin O  ---------- ---------- ---------- ---------- --SNKKTFKK YSRVAGLLTA ALIIGNLVTA 29
Novyiolysin     ---------- ---------- ---------- ---------- KS-LKTIIRS ISFLS--ILT LTCSCNFITS 29
Tetanolysin     ---------- ---------- ---------- ---------- KNVLKFVSRS LLIFS--MTG LISNYNSSNV 30
Ivanolysin      ---------- ---------- ---------- ---------- ---------- -KKIMLLLMT LLLVSLPLAQ 20
Listeriolysin   ---------- ---------- ---------- ---------- ---------- -KKIMLVFIT LILVSLPIAQ 20
Seeligeriolysin ---------- ---------- ---------- ---------- ---------- -KIFGLVIMS LLFVSLPITQ 20
Suilysin        ---------- ---------- ---------- ---------- --------KS SHLILSSIVS LALVGVTPLS 24
Pneumolysin     ---------- ---------- ---------- ---------- N--------- ---------- ---------- 3
Mitilysin (PLY) ---------- ---------- ---------- ---------- n--------- ---------- ---------- 3
Intermedilysin  ---------- ---------- ---------- ---------- -----NIARK LSR--VVLLS TLV------- 21
Viridanolysin   DGNVDSDYGH HSVTHTNFED NAWWQVDLGK TENVGKVKLY NRGDGNVANR LSNFDVVLLN EAKQEVARQH 140
Pyolysin        ---------- ---------- ---------- ---------- --------KA FASLVASVVA AATVTMPTAS 25
```

Figure 1A

| | | | | | | | | |
|---|---|---|---|---|---|---|---|---|
| Cereolysin | FAET------ | ---------- | ---------- | -QASNATDVT | KNASG----- | ---------- | ---------- | 47 |
| Anthrolysin | FAET------ | ---------- | ---------- | -QAGNATGAI | KNASD----- | ---------- | ---------- | 50 |
| Thuringiolysin | FAET------ | ---------- | ---------- | -QAGHATDIT | KNASS----- | ---------- | ---------- | 50 |
| Perfringolysin | FSK------- | ---------- | ---------- | -------DIT | DKNQS----- | ---------- | ---------- | 37 |
| Alveolysin | SA-------- | ---------- | ---------- | --------AP | TEPND----- | ---------- | ---------- | 39 |
| Caniolysin | NADSNKQNTA | NTETTTTNEQ | PKPESSELTT | EKAGQKMDDM | LNSNDMIKLA | PKEMPLESAE | KEEKKSEDNK | 102 |
| Equisimilysin | NADSNKQNTA | NTETTTTNEQ | PKPESSELTT | EKAGQKMDDM | LNSNDMIKLA | PKEMPLESAE | KEEKKSEDNK | 99 |
| Streptolysin O | NAESNKQNTA | STETTTTSEQ | PKPESSELTI | EKAGQKMDDM | LNSNDMIKLA | PKEMPLESAE | KEEKKSEDKK | 99 |
| Novyiolysin | TQK-NV---- | ---------- | ---------- | --------SL | LSGPNKVI-- | ---------- | -----KPKK- | 48 |
| Tetanolysin | LAKGNVEE-- | ---------- | ---------- | -------HSL | INNGQVVT-- | ---------- | -----SNTKC | 54 |
| Ivanolysin | EAQA-DASVY | SYQGI-ISHM | APPASPP--- | ---------- | ---------- | ---------- | -----AKPKT | 50 |
| Listeriolysin | QTEAKDASAF | NKENL-ISSM | APPASPP--- | ---------- | ---------- | ---------- | -----ASPKT | 51 |
| Seeligeriolysin | QPEARDVPAY | DRSEVTISPA | ETPESPP--- | ---------- | ---------- | ---------- | -----ATPKT | 52 |
| Suilysin | VLA------- | ---------- | ---------- | ---------- | ---------- | ---------- | ---------- | 27 |
| Pneumolysin | ---------- | ---------- | ---------- | ---------- | ---------- | ---------- | ---------- | 3 |
| Mitilysin (PLY) | ---------- | ---------- | ---------- | ---------- | ---------- | ---------- | ---------- | 3 |
| Intermedilysin | ---LSSAAPI | SAAFAETPTK | PKAAQTEKKP | EK-------- | -------KP- | --------EN | SNSEAAK--- | 61 |
| Viridanolysin | FDSLNGKAEL | EVFF--TAKD | ARYVKVELKT | KN-------- | -------TPL | SLAEVEVFRS | ATTQVGQDRT | 193 |
| Pyolysin | FAAGLGNSSG | LTDGLSAPRA | SISPTDKVDL | KSA------- | ---------- | ---------- | ---------- | 58 |

| | | | | | | | | |
|---|---|---|---|---|---|---|---|---|
| Cereolysin | ---------I | DTGIANLKYN | NQEVLAVNGD | KVESFVPKES | INSNGKFVVV | EREKKSLTTS | PVDISIIDSV | 108 |
| Anthrolysin | ---------I | NTGIANLKYD | SRDILAVNGD | KVESFIPKES | INSNGKFVVV | EREKKSLTTS | PVDILIIDSV | 111 |
| Thuringiolysin | ---------I | DTGIGNLTYN | NQEVLAVNGD | KVESFVPKES | INSNGKFVVV | EREKKSLTTS | PVDISIIDSV | 111 |
| Perfringolysin | ---------I | DSGISSLSYN | RNEVLASNGD | KIESFVPKEG | KKAGNKFIVV | ERQKRSLTTS | PVDISIIDSV | 98 |
| Alveolysin | ---------I | DMGIAGLNYN | RNEVLAIQGD | QISSFVPKEG | IQSNGKFIVV | ERDKKSLTTS | PVDISIVDSI | 100 |
| Caniolysin | KSEEDHTEEI | NDKIYSLNYN | ELEVLAKNGE | TIENFVPKEG | VKKADKFIVI | ERKKKNINTT | PVDISIIDSV | 172 |
| Equisimilysin | KSEEDHTEEI | NDKIYSLNYN | ELEVLAKNGE | TIENFVPKEG | VKKADKFIVI | ERKKKNINTT | PVDISIIDSV | 169 |
| Streptolysin O | KSEEDHTEEI | NDKIYSLNYN | ELEVLAKNGE | TIENFVPKEG | VKKADKFIVI | ERKKKNINTT | PVDISIIDSV | 169 |
| Novyiolysin | ------TKSL | DDRIYGLKYD | PNKILSFNGE | KVENFVPNEG | FSTPDKYIVI | KREKKSISDS | TADIAVIDSM | 112 |
| Tetanolysin | NLAKDNSSDI | DKNIYGLSYD | PRKILSYNGE | QVENFVPAEG | FENPDKFIVV | KREKKSISDS | TADISIIDSI | 124 |
| Ivanolysin | PVEKKNAAQI | DQYIQGLDYD | KNNILVYDGE | AVKNVPPKAG | YKEGNQYIVV | EKKKKSINQN | NADIQVINSL | 120 |
| Listeriolysin | PIEKKHADEI | DKYIQGLDYN | KNNVLVYHGD | AVTNVPPRKG | YKDGNEYIVV | EKKKKSINQN | NADIQVVNAI | 121 |
| Seeligeriolysin | PVEKKHAEEI | NKYIWGLNYD | KNSILVYQGE | AVTNVPPKKG | YKDGSEYIVV | EKKKKGINQN | NADISVINAI | 122 |
| Suilysin | ----DSKQDI | NQYFQSLTYE | PQEILTNEGE | YIDNPPATTG | MLENGRFVVL | RREKKNITNN | SADIAVIDAK | 93 |
| Pneumolysin | -------KAV | NDFILAMNYD | KKKLLTHQGE | SIENRFIKEG | NQLPDEFVVI | ERKKRSLSTN | TSDISVTATN | 66 |
| Mitilysin (PLY) | -------kav | ndfilamdyd | kkkllthqge | sienrfikeg | nqlpdefvvi | erkkrslstn | tsdisvtatn | 66 |
| Intermedilysin | -------KAL | NDYIWGLQYD | KLNILTHQGE | KLKNHSSREA | FHRPGEYVVI | EKKKQSISNA | TSKLSVSSAN | 124 |
| Viridanolysin | APVVDQTSAL | KDYLFGLTYN | PLDILTRKGE | TLENRYNTSA | KEQNGEFVVV | EKIKKTLSTG | TADVSING-- | 261 |
| Pyolysin | --QETDETGV | DKYIRGLKYD | PSGVLAVKGE | SIENVPVTKD | QLKDGTYTVF | KHERKSFNNL | RSDISAFDAN | 126 |

Figure 1B

| | | | | | | | | |
|---|---|---|---|---|---|---|---|---|
| Cereolysin | VNRTYPGAVQ | LANKAFADNQ | PSLLVAKRKP | LNISIDLPGM | -RKENTITVQ | NPTYGNVAGA | VDDLVSTWNE | 177 |
| Anthrolysin | VNRTYPGAVQ | LANKAFADNQ | PSLLVAKRKP | LNISIDLPGM | -RKENTITVQ | NPTYGNVAGA | VDDLVSTWNE | 180 |
| Thuringiolysin | ANRTYPGAVQ | LANKAFADNQ | PSLLVAKRKP | LNISIDLPGM | -RKENTITVQ | NPTYGNVAGA | VDDLVSTWNE | 180 |
| Perfringolysin | NDRTYPGALQ | LADKAFVENR | PTILMVKRKP | ININIDLPGL | -KGENSIKVD | DPTYGKVSGA | IDELVSKWNE | 167 |
| Alveolysin | TNRTYPGAIQ | LANKDFADNQ | PSLVMAARKP | LDISIDLPGL | -KNENTISVQ | NPNYGTVSSA | IDQLVSTWGE | 169 |
| Caniolysin | TDRTYPAALQ | LANKGFTENK | PDAVVTKRNP | QKIHIDLPGM | -GDKATVEVN | DPTYANVSTA | IDNLVNQWHD | 241 |
| Equisimilysin | TDRTYPAALQ | LANKGFTENK | PDAVVTKRNP | QKIHIDLPGM | -GDKATVEVN | DPTYANVSTA | IDNLVNQWHD | 238 |
| Streptolysin O | TDRTYPAALQ | LANKGFTENK | PDAVVTKRNP | QKIHIDLPGM | -GDKATVEVN | DPTYANVSTA | IDNLVNQWHD | 238 |
| Novyiolysin | NDKTYPGAIQ | LANRNLIENK | PNIVSCERKP | ITISIDLPGM | -GEEGKTTIT | SPTYSSVKAG | IDSLLNKWNS | 181 |
| Tetanolysin | NDRTYPGAIQ | LANRNLMENK | PDIISCERKP | ITISVDLPGM | -AEDGKKVVN | SPTYSSVNSA | INSILDTWNS | 193 |
| Ivanolysin | ASLTYPGALV | KANSELVENQ | PDVLPVKRDS | VTLSIDLPGM | VNHDNEIVVQ | NATKSNINDG | VNTLVDRWNN | 190 |
| Listeriolysin | SSLTYPGALV | KANSELVENQ | PDVLPVKRDS | LTLSIDLPGM | TNQDNKIVVK | NATKSNVNNA | VNTLVERWNE | 191 |
| Seeligeriolysin | SSLTYPGALV | KANRELVENQ | PNVLPVKRDS | LTLSVDLPGM | TKKDNKIFVK | NPTKSNVNNA | VNTLVERWND | 192 |
| Suilysin | AANIYPGALL | RADQNLLDNN | PTLISIARGD | LTLSLNLPGL | ANGDSHTVVN | SPTRSTVRTG | VNNLLSKWNN | 163 |
| Pneumolysin | DSRLYPGALL | VVDETLLENN | PTLLAVDRAP | MTYSIDLPGL | ASSDSFLQVE | DPSNSSVRGA | VNDLLAKWHQ | 136 |
| Mitilysin (PLY) | dsrlypgall | vvdetllenn | ptllavdrap | mtysidlpgl | assdsflqve | dpsnssvrga | vndllakwhq | 136 |
| Intermedilysin | DDRIFPGALL | KADQSLLENL | PTLIPVNRGK | TTISVNLPGL | KNGESNLTVE | NPSNSTVRTA | VNNLVEKWIQ | 194 |
| Viridanolysin | NQNVFLGGLY | KANQNLLENQ | PELISLARAK | GTVSVDLPGM | IHSENKIEA- | NPTTSGMQEA | MNTLVEKWTK | 330 |
| Pyolysin | NAHVYPGALV | LANKDLAKGS | PTSIGIARAP | QTVSVDLPGL | VDGKNKVVIN | NPTKSSVTQG | LNGLLDGWIQ | 196 |

| | | | | | | | | |
|---|---|---|---|---|---|---|---|---|
| Cereolysin | KYSTTH-TLP | ARMQYTESMV | YSKSQIASAL | NVNAKYLDNS | LNIDFNAVAN | GEKKVMVAAY | KQIFYTVSAE | 246 |
| Anthrolysin | KYSTTH-TLP | ARMQYTESMV | YSKSQIASAL | NVNAKYLDNS | LNIDFNAVAN | GEKKVMVAAY | KQIFYTVSAE | 249 |
| Thuringiolysin | KYSETH-TLP | ARMQYTESMV | YSKSQIASAL | NVNAKYLDNS | LNIDFNAVAN | GEKKVMVAAY | KQIFYTVSAE | 249 |
| Perfringolysin | KYSSTH-TLP | ARTQYSESMV | YSKSQISSAL | NVNAKVLENS | LGVDFNAVAN | NEKKVMILAY | KQIFYTVSAD | 236 |
| Alveolysin | KYSSTH-TLP | ARLQYAESMV | YSQNQISSAL | NVNAKVLNGT | LGIDFNAVAN | GEKKVMVAAY | KQIFYTVSAG | 238 |
| Caniolysin | NYSGGN-TLP | ARTQYTESMV | YSKSQIEAAL | NVNSKILDGT | LGIDFKSISK | GEKKVMIAAY | KQIFYTVSAN | 310 |
| Equisimilysin | NYSGGN-TLP | ARTQYTESMV | YSKSQIEAAL | NVNSKILDGT | LGIDFKSISK | GEKKVMIAAY | KQIFYTVSAN | 307 |
| Streptolysin O | NYSGGN-TLP | ARTQYTESMV | YSKSQIEAAL | NVNSKILDGT | LGIDFKSISK | GEKKVMIAAY | KQIFYTVSAN | 307 |
| Novyiolysin | HYSSIY-SIP | TRFSYSDSMV | YSKSQLSAKL | GCNFKALNKA | LDIDFDSIYK | GQKKVMLLAY | KQIFYTVNVD | 250 |
| Tetanolysin | KYSSKY-TIP | TRMSYSDTMV | YSQSQLSAAV | GCNFKALNKA | LNIDFDSIFK | GEKKVMLLAY | KQIFYTVSVD | 262 |
| Ivanolysin | KYSEEYPNIS | AKIDYDQEMA | YSESQLVAKF | GAAFKAVNNS | LNVNFGAISE | GKVQEEVINF | KQIYYTVNVN | 260 |
| Listeriolysin | KYAQAYPNVS | AKIDYDDEMA | YSESQLIAKF | GTAFKAVNNS | LNVNFGAISE | GKMQEEVISF | KQIYYNVNVN | 261 |
| Seeligeriolysin | KYSKAYPNIN | AKIDYSDEMA | YSESQLIAKF | GTAFKAVNNS | LNVNFEAISD | GKVQEEVISF | KQIYYNINVN | 262 |
| Suilysin | TYAGEYGNTQ | AELQYDETMA | YSMSQLKTKF | GTSFEKIAVP | LDINFDAVNS | GEKQVQIVNF | KQIYYTVSVD | 233 |
| Pneumolysin | DYGQVN-NVP | ARMQYEKITA | HSMEQLKVKF | GSDFEKTGNS | LDIDFNSVHS | GEKQIQIVNF | KQIYYTVSVD | 205 |
| Mitilysin (PLY) | dygqvn-nvp | armqyekita | hsmeqlkvkf | gsdfektgns | ldidfnsvhs | gekqiqivnf | kqiyytvsvd | 205 |
| Intermedilysin | KYSKTH-AVP | ARMQYESISA | QSMSQLQAKF | GADFSKVGAP | LNVDFSSVHK | GEKQVFIANF | RQVYYTASVD | 263 |
| Viridanolysin | NYSSSH-SVP | ARVQYESTTA | YSMNQLKAKF | GADFEKAGAP | LKIDFEAVQK | GEKQIEVVNF | KQIYYTATFD | 399 |
| Pyolysin | RNSK-YPDHA | AKISYDETMV | TSKRQLEAKL | GLGFEKVSAK | LNVDFDAIHK | RERQVAIASF | KQIYYTASVD | 265 |

Figure 1C

```
Cereolysin       LPNNPSDLFD NSVTFDELTR KGVSNSAPPV MVSNVAYGRT IYVKLETTSK SKDVQAAFKA LLK----NNS 312
Anthrolysin      LPNNPSDLFD NSVTFDELTR KGVSNSAPPV MVSNVAYGRT VYVKLETTSK SKDVQAAFKA LLK----NNS 315
Thuringiolysin   LPNNPSDLFD NSVTFDELTR KGVSNSAPPV MVSNVAYGRT VYVKLETTSK SKDVQAAFKA LLK----NNS 315
Perfringolysin   LPKNPSDLFD DSVTFNDLKQ KGVSNEAPPL MVSNVAYGRT IYVKLETTSS SKDVQAAFKA LIK----NTD 302
Alveolysin       LPNNPSDLFD DSVTFAELAR KGVSNEAPPL MVSNVAYGRT IYVKLETTSK SNDVQTAFKL LLN----NPS 304
Caniolysin       LPNNPADVFD KSVTFKELQA KGVSNEAPPL FVSNVAYGRT VFVKLETSSK SNDVEAAFSA ALK----GTD 376
Equisimilysin    LPNNPADVFD KSVTFKELQR KGVSNEAPPL FVSNVAYGRT VFVKLETSSK SNDVEAAFSA ALK----GTD 373
Streptolysin O   LPNNPADVFD KSVTFKDLQR KGVSNEAPPL FVSNVAYGRT VFVKLETSSK SNDVEAAFSA ALK----GTD 373
Novyiolysin      APNHPSDFFG DKVTFNDLAK KGVNSKNPPV YVSSVSYGRT IYVKLETTSK SANVKAAFKA LIE----NQN 316
Tetanolysin      PPNRPSDLFG DSVTFDELAL KGINNNNPPA YVSNVAYGRT IYVKLETTSK SSHVKAAFKA LIN----NQD 328
Ivanolysin       EPTSPSRFFG KSVTKENLQA LGVNAENPPA YISSVAYGRD IFVKLSTSSH STRVKAAFDT AFK----GKS 326
Listeriolysin    EPTRPSRFFG KAVTKEQLQA LGVNAENPPA YISSVAYGRQ VYLKLSTNSH STKVKAAFDA AVS----GKS 327
Seeligeriolysin  EPTSPSKFFG GSVTKEQLDA LGVNAENPPA YISSVAYGRQ VYVKLSSSSH SNKVKTAFEA AMS----GKS 328
Suilysin         EPESPSKLFA EGTTVEDLKR NGITDEVPPV YVSSVSYGRS MFIKLETSSR STQVQAAFKA AIK----GVD 299
Pneumolysin      AVKNPGDVFQ DTVTVEDLKQ RGISAERPLV YISSVAYGRQ VYLKLETTSK SDEVEAAFEA LIK----GVK 271
Mitilysin (PLY)  avknpgdvfq dtvtvedlrq rgisadrplv yissvaygrq vylklettsk sdeveaafea lik----gvk 271
Intermedilysin   SPNSPSALFG SGITPTDLIN RGVNSKTPPV YVSNVSYGRA MYVKFETTSK STKVQAAIDA VVK----GAK 329
Viridanolysin    APTNPAAVFD KSVTPEDLKQ RGVDSQTPPV YVSNVSYGRQ IYVKFESTSK STELKAAINA VIK----GAT 465
Pyolysin         TPTSPHSVFG PNVTAQDLKD RGVNNKNPLG YISSVSYGRQ IFVKLETTST SNDVQAAFSG LFKAKFGNLS 335

Cereolysin       VETSGQYKDI FEESTFTAVV LGGDAKEHNK VVTKDFNEIR NIIKDNAELS LKNPAYPISY TSTFLKDNST 382
Anthrolysin      VETSGQYKDI FEESTFTAVV LGGDAKEHNK VVTKDFNEIR NIIKDNAELS FKNPAYPISY TSTFLKDNAT 385
Thuringiolysin   VETSGQYKDI FEESTFTAVV LGGDAKEHNK VVTKDFNEIR NIIKDNAELS FKNPAYPISY TSTFLKDNAT 385
Perfringolysin   IKNSQQYKDI YENSSFTAVV LGGDAQEHNK VVTKDFDEIR KVIKDNATFS TKNPAYPISY TSVFLKDNSV 372
Alveolysin       IQASGQYKDI YENSSFTAVV LGGDAQTHNQ VVTKDFNVIQ SVIKDNAQFS SKNPAYPISY TSVFLKDNSI 374
Caniolysin       VKTNGKYSDI LENSSFTAVV LGADAAEHNK VVTKDFDVIR NVIKANATFS RKNPAYPISY TSVFLKNNKI 446
Equisimilysin    VKTNGKYSDI LENSSFTAVV LGGDAAEHNK VVTKDFDVIR NVIKDNATFS RKNPAYPISY TSVFLKNNKI 443
Streptolysin O   VKTNGKYSDI LENSSFTAVV LGGDAAEHNK VVTKDFDVIR NVIKDNATFS RKNPAYPISY TSVFLKNNKI 443
Novyiolysin      ISSNSEYKNI LNQSSFTATV LGGGAKEHNK VITKNFDEIR NIITNNSEYS PRNPGYPIAY TTSFLKDNSV 386
Tetanolysin      ISSNAEYKDI LNQSSFTATV LGGGAQEHNK IITKDFDEIR NIIKNNSVYS PQNPGYPISY TTTFLKDNSI 398
Ivanolysin       VKGDTELENI IQNASFKAVI YGGSAKDEVE IIDGDLSKLR DILKQGANFD KKNPGVPIAY TTNFLKDNQL 396
Listeriolysin    VSGDVELTNI IKNSSFKAVI YGGSAKDEVQ IIDGNLGDLR DILKKGATFN RETPGVPIAY TTNFLKDNEL 397
Seeligeriolysin  VKGDVELTNI IKNSSFKAVI YGGSAKEEVE IIDGNLGELR DILKKGSTYD RENPGVPISY TTNFLKDNDL 398
Suilysin         ISGNAEYQDI LKNTSFSAYI FGGDAGSAAT VVSGNIETLK KIIEEGARYG KLNPGVPISY STNFVKDNRP 369
Pneumolysin      VAPQTEWKQI LDNTEVKAVI LGGDPSSGAR VVTGKVDMVE DLIQEGSRFT ADHPGLPISY TTSFLRDNVV 341
Mitilysin (PLY)  vapqtewkqi ldntevkavi lggdpssgar vvtgkvdmve dliqegsrft adhpglpisy ttsflrdnvv 341
Intermedilysin   LKAGTEYENI LKNTKITAVV LGGNPGEASK VITGNIDTLK DLIQKGSNFS AQSPAVPISY TTSFVKDNSI 399
Viridanolysin    IAPNSEWSRL LKNTSVTAVI VGGNASGAAK VVTGTVENLK ELIREGANFS AQSPAVPISY KTAFLKDNAQ 535
Pyolysin         TEFKAKYADI LNKTRATVYA VGGSARGGVE VATGNIDALK KIIKEESTYS TKVPAVPVSY AVNFLKDNQL 405
```

Figure 1D

PNEUMOLYSIN MUTANTS AND METHODS OF USE THEREOF

CROSS REFERENCE TO RELATED APPLICATIONS/INCORPORATION BY REFERENCE STATEMENT

This application is a US national stage application filed under 35 USC § 371 of International Application No. PCT/US2015/061859, filed Nov. 20, 2015; which claims priority to U.S. provisional application Ser. No. 62/082,848, filed Nov. 21, 2014. The entire contents of the above-referenced patent applications are hereby expressly incorporated herein by reference.

STATEMENT REGARDING FEDERALLY SPONSORED RESEARCH OR DEVELOPMENT

This invention was made with government support under Contract Number AI037657 awarded by the National Institutes of Health (NIH). The government has certain rights in the invention.

BACKGROUND

The cholesterol-dependent cytolysins (CDCs) are a large family of pore-forming toxins that are produced by more than 20 species from the genera *Clostridium, Streptococcus, Listeria, Bacillus*, and *Arcanobacterium*. The pore-forming mechanism of these toxins exhibits two hallmark characteristics: an absolute dependence on the presence of membrane cholesterol and the formation of an extraordinarily large pore. Each CDC is produced as a soluble monomeric protein that, with the exception of one member, is secreted by a type II secretion system. Upon encountering a eukaryotic cell, the CDCs undergo a transformation from a soluble monomeric protein to a membrane-embedded supramolecular pore complex. The conversion of the monomers to an oligomeric, membrane-inserted pore complex requires some extraordinary changes in the structure of the monomer.

Although the CDCs are well known as beta-hemolytic proteins, it has become increasingly apparent that bacterial pathogens use these proteins in much more sophisticated ways than as simple hemolysins or general cell-lytic agents. The CDC structure also exhibits a plasticity that has allowed the evolution of unique features for some CDCs, without compromising the fundamental pore-forming mechanism. Some of these features are reflected in CDCs that activate complement, that utilize a nonsterol receptor, that exhibit a pH-sensitive, poreforming mechanism, or that can function as a protein translocation channel.

CDCs are β-sheet-rich, four-domain proteins. A highly conserved tryptophan-rich undecapeptide is present in domain 4, which participates in the binding of some CDCs to cholesterol-rich membranes. In addition, three other short hydrophobic loops (Loops L1, L2 and L3) juxtaposed to the undecapeptide at the tip of domain 4 have been shown to also insert into the membrane surface and anchor the CDC to the membrane in a perpendicular orientation. After membrane binding, the CDC monomers diffuse laterally to initiate formation of the membrane oligomer.

Once the prepore complex reaches a large size, presumably a complete ring structure, it then makes the transition to the pore complex. The transmembrane pore is formed when two α-helical bundles in domain 3 of each monomer within the prepore complex are converted to two extended amphipathic transmembrane β-hairpins (TMHs). Upon the conversion of the prepore to the pore, the height of the prepore structure undergoes a vertical collapse of about 40 Angstroms. The collapse of the prepore structure brings the domain 3 TMHs within striking distance of the membrane surface, at which point they undergo a concerted insertion into the membrane that results in the formation of the large transmembrane β-barrel pore. The CDC pore is large: it is comprised of 35 to 50 monomers and exhibits a diameter of 250 to 300 Angstroms.

During the process of the CDC monomer interaction with the membrane, the undecapeptide and the three other short loops (L1, L2, and L3) at the tip of the domain 4 β-sandwich insert into the membrane upon the interaction of the CDC monomers with the membrane surface. These loops do not penetrate deeply into the membrane and apparently do not directly participate in the structure of the transmembrane pore. One function of the loops appears to be to anchor the monomers to the membrane in an upright position. Domain 4 exists in a perpendicular orientation to the membrane and is surrounded by the aqueous milieu, even in the oligomeric state.

Domain 4 of the CDCs mediates membrane recognition, whether it is via cholesterol or another receptor, as in the case of ILY (Intermedilysin).

The CDCs are also capable of lysis of a wide variety of nucleated cell types in vitro, and this capacity has in turn been used by many investigators to permeabilize various eukaryotic cell types with CDCs. Despite the ability of these toxins to perform as general cell-lytic agents in vitro, it has not yet been demonstrated that cell lysis is a primary function of the CDCs during an infection. The contribution of CDCs to infection has been studied for example in *Listeria monocytogenes, Streptococcus pyogenes, Streptococcus pneumoniae, Arcanobacterium pyogenes*, and *Clostridium perfringens*. The results of some of these studies suggest that the bacteria use the CDCs in more sophisticated ways than as general cytolytic agents. It also appears that the CDC structure has undergone some unique evolutionary transformations that facilitate the pathogenic mechanism of these bacterial species.

*Streptococcus pneumoniae* is an important agent of disease in humans, especially among infants, the elderly, persons with chronic illness, and immunocompromised persons. It is a bacterium frequently isolated from patients with invasive diseases such as bacteremia/septicemia, pneumonia, and meningitis with high morbidity and mortality throughout the world. Even with appropriate antibiotic therapy, pneumococcal infections still result in many deaths. Although the advent of antimicrobial drugs has reduced the overall mortality from pneumococcal disease, the presence of resistant pneumococcal strains has become a major problem in the world today and underscores the need for treating and preventing pneumococcal infection by methods in addition to antimicrobials. Effective pneumococcal vaccines could have a major impact on the morbidity and mortality associated with *S. pneumoniae* disease. Such vaccines would also potentially be useful to prevent otitis media in infants and young children. New immunogenic pneumococcal vaccines that provide long-term immunity are clearly needed, especially for children aged less than 2 years, because incidence of disease is high and antibody responses to the polysaccharide vaccine antigens are poor in this age group.

Each year in the United States, pneumococcal disease accounts for an estimated 3,000 cases of meningitis, 50,000 cases of bacteremia, 500,000 cases of pneumonia, and 7 million cases of otitis media.

Severe pneumococcal infections result from dissemination of bacteria to the bloodstream and the central nervous system. In 1997, data from community-based studies indicated that overall annual incidence of pneumococcal bacteremia in the United States was an estimated 15-30 cases per 100,000; the rate was higher for persons aged greater than or equal to 65 years (50-83 cases per 100,000) and for children aged less than or equal to 2 years (160 cases per 100.000). In adults, 60%-87% of pneumococcal bacteremia was associated with pneumonia; in young children, the primary sites of infection were frequently not identified.

In the United States, the risk for acquiring bacteremia is lower among white persons than among persons in other racial/ethnic groups (i.e., blacks, Alaskan Natives, and American Indians). Black adults have a threefold to fivefold higher overall incidence of bacteremia (49-58 cases per 100,000) than whites. Rates of invasive pneumococcal disease are exceptionally high among Alaskan Natives and American Indians. The age-adjusted annual incidence of invasive pneumococcal infection among Alaskan Natives and Alaskan Native children aged less than 2 years was determined by a prospective surveillance study to be 74 cases and 624 cases per 100,000, respectively. Rates for meningitis and bacteremic pneumonia are eightfold to tenfold higher for Alaskan Natives of all ages than for other U.S. population groups. The highest incidence rates for any U.S. population have been reported among specific American Indian groups (e.g., Apache). The overall annual incidence for such groups is 156 cases per 100,000; the incidence for children aged 1-2 years in these groups is 2,396 cases per 100,000.

In the United States, the estimated overall annual incidence of pneumococcal meningitis is one to two cases per 100,000. The incidence of pneumococcal meningitis is highest among children aged 6-24 months and persons aged greater than or equal to 65 years. Rates for blacks are twice as high as those for whites and Hispanics. Because the incidence of *Haemophilus influenzae* type b (Hib) meningitis in children rapidly decreased following the introduction of Hib conjugate vaccines, *S. pneumoniae* has become the most common cause of bacterial meningitis in the United States (26).

Strains of drug-resistant *S. pneumoniae* (DRSP) have become increasingly common in the United States and in other parts of the world. In some areas, as many as 35% of pneumococcal isolates have been reported to have intermediate-level (minimum inhibitory concentration {MIC} equal to 0.1-1.0 μg/mL) or high-level (MIC greater than or equal to 2 μg/mL) resistance to penicillin. Many penicillin-resistant pneumococci are also resistant to other antimicrobial drugs (e.g., erythromycin, trimethoprim-sulfamethoxazole, and extended-spectrum cephalosporins). High-level penicillin resistance and multidrug resistance often complicate the management of pneumococcal infection and make choosing empiric antimicrobial therapy for suspected cases of meningitis, pneumonia, and otitis media increasingly difficult. Treating patients infected with nonsusceptible organisms may require the use of expensive alternative antimicrobial agents and may result in prolonged hospitalization and increased medical costs. The impact of antimicrobial resistance on mortality is not clearly defined. Emerging antimicrobial resistance further emphasizes the need for preventing pneumococcal infections by vaccination.

The currently available pneumococcal vaccines, PNEUMOVAX®23 (Merck & Co., Inc., Kenilworth, N.J.) and PNU-IMMUNE®23 (Lederle-Praxis Biologicals, Pearl River, N.Y.), include 23 purified capsular polysaccharide antigens of *S. pneumoniae* (serotypes 1, 2, 3, 4, 5, 6B, 7F, 8, 9N, 9V, 10A, 11A, 12F, 14, 15B, 17F, 18C, 19A, 19F, 20, 22F, 23F, and 33F). These vaccines were licensed in the United States in 1983 and replaced an earlier 14-valent formulation that was licensed in 1977. One dose (0.5 mL) of the 23-valent vaccine contains 25 μg of each capsular polysaccharide antigen dissolved in isotonic saline solution with phenol (0.25%) or thimerosal (0.01%) added as preservative and no adjuvant. As of 1997, the 23 capsular types in the vaccine represented at least 85%-90% of the serotypes that cause invasive pneumococcal infections among children and adults in the United States. The six serotypes (6B, 9V, 14, 19A, 19F, and 23F) that most frequently caused invasive drug-resistant pneumococcal infection in the United States as of 1997 are represented in the 23-valent vaccine. As noted below, the desirability of a vaccine solely comprised of capsular polysaccharides is limited.

Pneumolysin in particular is a key component in the pathogenesis of streptococcal pneumonia, which kills over a million humans per year worldwide. The use of pneumolysin as a part of a vaccine for *Streptococcus pneumoniae* lung infections and otitis media could provide important benefits, since vaccines based on the capsular polysaccharide are losing effectiveness due to genetic variation and are difficult to generate, as there are more than 90 different capsular serotypes of *Streptococcus pneumoniae*. The immunity to one capsular type does not protect against another capsular type. The currently available pneumococcal vaccine discussed above, which comprises 23 capsular polysaccharides from the strains that most frequently cause disease, has significant shortcomings related primarily to the poor immunogenicity of some capsular polysaccharides, the diversity of the serotypes and the differences in the distribution of serotypes over time, geographic areas, and age groups. Currently, a point mutation variant of pneumolysin has been used for vaccine development. This pneumolysin mutant (referred to as "Pd-B") contains a single mutation at position 433 (wherein the native tryptophan residue has been changed to a phenylalanine). This mutation in pneumolysin is in the conserved undecapeptide of Domain 4, the structure within the cholesterol-dependent cytolysins (CDCs) which had long been thought to mediate binding to mammalian membranes.

While the pneumolysin Pd-B mutant is conventionally used for vaccine development, this protein is still able to undergo a variety of structural transitions that occur after binding to the membrane of mammalian cells. These changes dramatically alter its structure and may decrease its ability to stimulate an effective neutralizing immune response in a patient, primarily because the structure of pneumolysin that the patient's immune system may "see" will be that of the terminal cell-bound oligomeric complex instead of the initial structure of the soluble monomeric pneumolysin. More importantly, the current genetically toxoided pneumolysin is still hampered by an unacceptable level of toxicity. The basis for this toxicity is not yet clear, but likely results from the fact that this toxoid can still bind to and oligomerize on mammalian cells.

Therefore, mutants of cholesterol-dependent cytolysins, such as (but not limited to) pneumolysin, which have reduced toxicity and reduced hemolytic activity, yet which stimulate an immune response against corresponding disease organisms, would be of great benefit.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Several embodiments of the present disclosure are hereby illustrated in the appended drawings. It is to be noted, however, that the appended drawings only illustrate several typical embodiments and are therefore not intended to be considered limiting of the scope of the disclosure. Further, in the appended drawings, like or identical reference numerals may be used to identify common or similar elements, and not all such elements may be so numbered. The figures are not necessarily to scale, and certain features and certain views of the figures may be shown exaggerated in scale or in schematic in the interest of clarity and conciseness.

FIGS. 1A-E contain an amino acid alignment comparison of native amino acid sequences of various cholesterol-dependent cytolysins. The amino acid sequences of each protein identified herein correspond to the SEQ ID NO's in Table 1 herein; for example, Cereolysin in FIG. 1A-E corresponds in SEQ ID NO:2 in Table 1, and SEQ ID No:18 (PAF) in Table 1 corresponds to Viridanolysin in FIG. 1A-E.

DETAILED DESCRIPTION

Figure 1E:
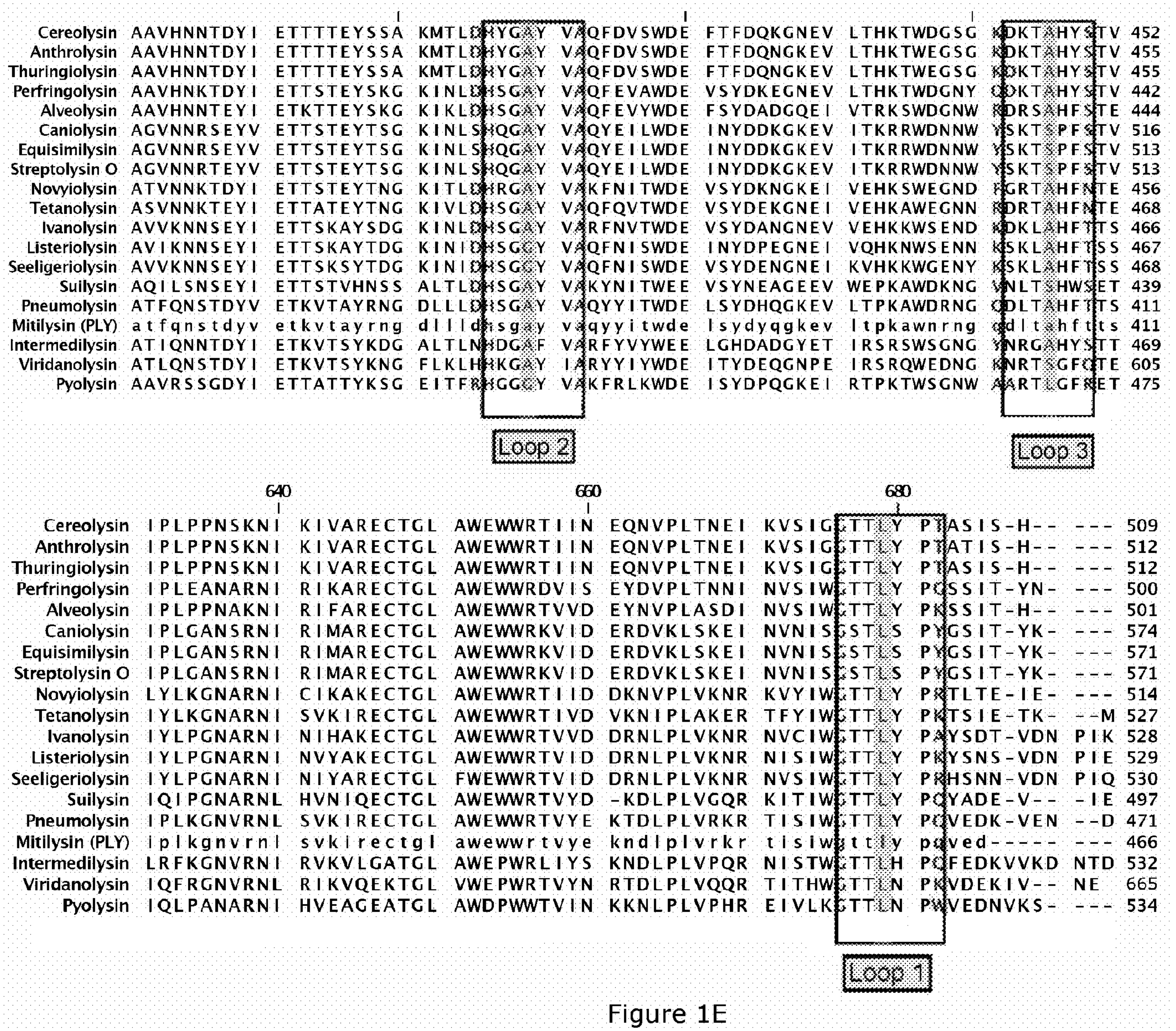

Before explaining at least one embodiment of the inventive concepts in detail by way of exemplary drawings, experimentation, results, and laboratory procedures, it is to be understood that the present disclosure is not limited to the details of composition, components, and methods as set forth in the following description or illustrated in the drawings, experimentation, and/or results. The present disclosure is capable of other embodiments or of being practiced or carried out in various ways. As such, the language used herein is intended to be given the broadest possible scope and meaning, and the embodiments are meant to be exemplary, not exhaustive. Also, it is to be understood that the phraseology and terminology employed herein is for the purpose of description and should not be regarded as limiting.

Unless otherwise defined herein, scientific and technical terms used in the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Green and Sambrook (Molecular Cloning: A Laboratory Manual (4th ed., Cold Spring Harbor Laboratory Press, Cold Spring Harbor, N.Y. (2012)) and Coligan et al. (Current Protocols in Immunology, Current Protocols, Wiley Interscience (1994)), which are expressly incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

All patents, published patent applications, and non-patent publications mentioned in the present specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference. In particular, the entire contents of the following patents and patent applications are hereby expressly incorporated herein by reference: U.S. Ser. No. 13/401,460, filed Feb. 21, 2012; U.S. Ser. No. 12/102,696, filed Apr. 14, 2008, now U.S. Pat. No. 8,128,939, issued Mar. 6, 2012; U.S. Ser. No. 60/923,281, filed Apr. 13, 2007; and U.S. Ser. No. 62/082,848, filed Nov. 21, 2014.

All of the compositions and/or methods described and/or otherwise contemplated herein can be made and executed without undue experimentation in light of the present disclosure. While the compositions and methods disclosed and/or otherwise contemplated herein have been described in terms of particular embodiments, it will be apparent to those of skill in the art that variations may be applied to the compositions and/or methods, and in the steps or in the sequence of steps of the methods, described or otherwise contemplated herein without departing from the concept, spirit, and scope of the present disclosure. All such similar substitutes and modifications apparent to those skilled in the art are deemed to be within the spirit, scope, and concept of the inventive concepts as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one." and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"). "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C. or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout the specification and claims, unless the context requires otherwise, the terms "substantially" and "about" will be understood to not be limited to the specific terms qualified by these adjectives/adverbs, but will be understood to indicate a value includes the inherent variation of error for the device, the method being employed to determine the value and/or the variation that exists among study subjects. Thus, said terms allow for minor variations and/or deviations that do not result in a significant impact thereto. For example, in certain instances the term "about" is used to indicate that a value includes the inherent variation of error for the device, the method being employed to determine the value and/or the variation that exists among study subjects. Similarly, the term "substantially" may also relate to 80% or higher, such as 85% or higher, or 90% or higher, or 95% or higher, or 99% or higher, and the like.

The terms "purified protein" or "isolated protein" as used herein mean that the protein or fragment is sufficiently free of contaminants or cell components with which the protein normally occurs as to distinguish the protein from the contaminants or cell components. It is not contemplated that "purified" necessitates having a preparation that is technically totally pure (homogeneous), but purified as used herein means the protein or polypeptide fragment is sufficiently separated from contaminants or cell components with which it normally occurs to provide the protein in a state where it can be used in an assay, such as immunoprecipitation or ELISA. For example, the purified protein can be in an electrophoretic gel.

The term "mutant" when used herein to describe a polypeptide refers to a polypeptide which is less than 100% identical to an amino acid sequence of the corresponding wild type (native) polypeptide, and in particular to a synthetic or recombinant polypeptide wherein one or more amino acid residue positions of the wild type polypeptide have been substituted. The term "variant" may be used interchangeably with the term "mutant."

The mutant CDCs described herein may be combined with one or more pharmaceutically-acceptable excipients, including carriers, vehicles, and diluents, to form immunogenic compositions. The term pharmaceutically-acceptable excipient as used herein is intended to refer to solvents or other materials in which the mutant CDCs (e.g., mutant pneumolysin polypeptides) disclosed herein can be disposed to improve solubility, deliverability, dispersion, stability, and/or conformational integrity. Examples of such pharmaceutically-acceptable excipients include, but are not limited to, water, saline solutions (such as physiological saline solutions and buffered saline solutions at neutral pH such as phosphate buffered saline (PBS)), ethanol, sugars, dextrose, glycerol, and/or polyalcohols (such as mannitol and sorbitol). Other types of carriers include liposomes or polymers and the like.

The term "pharmaceutically acceptable" refers to a material that is not biologically or otherwise undesirable, i.e., the material may be administered to an individual along with the selected compound without causing any undesirable biological effects or interacting in an undesirable manner with any of the other components of the pharmaceutical composition in which it is contained.

The mutant CDCs or immunogenic compositions containing said mutant CDCs may further be combined with an adjuvant such as (but not limited to) Freund's incomplete adjuvant, Freund's Complete adjuvant, alum, monophosphoryl lipid A, alum phosphate or hydroxide, QS-21, salts, i.e., $AlK(SO_4)_2$, $AlNa(SO_4)_2$, $AlNH_4(SO_4)_2$, silica, kaolin, and/or carbon polynucleotides (i.e., poly IC and poly AU). Non-limiting examples of adjuvants include QuilA, Alhydrogel, and the like. The term "adjuvant" refers to a substance that is capable of enhancing, accelerating, or prolonging an immune response when give with the immunogen of the composition. Optionally, the mutant CDCs contemplated herein can be combined with immunomodulators and immunostimulants, such as but not limited to, interleukins, interferons, and the like. Many vaccine and other pharmaceutical formulations are known to those of skill in the art.

By "biologically active" is meant the ability to modify the physiological system of an organism. A molecule can be biologically active through its own functionalities, or may be biologically active based on its ability to activate or inhibit molecules having their own biological activity.

The term "immunogenic" where used herein is intended to refer to the ability of a substance to elicit an immune response. For example, an "immunogenic composition" is a composition comprising a mutant CDC, such as a mutant pneumolysin polypeptide, which is able to elicit an immune response in a subject animal, such as the production of antibodies, when administered thereto. The term "vaccine" refers to an immunogenic composition for administration to a subject for eliciting an immune response against a particular antigen. For example, a vaccine comprising one or more of the mutant pneumolysin polypeptides disclosed herein is a vaccine for use in the treatment of a disease or condition caused by the bacterium *Streptococcus pneumoniae*.

The term "patient" or "subject" as used herein includes human and veterinary subjects. "Mammal" for purposes of treatment refers to any animal classified as a mammal, including (but not limited to) humans, domestic animals (such as, but not limited to, dogs and cats), farm animals (such as, but not limited to, cows, horses, pigs, goats, and sheep), laboratory animals (such as, but not limited to, mice, rats, rabbits, guinea pigs, and chinchillas), nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

The phrase "administering a therapeutically effective amount" or "administering a prophylactically effective amount" is intended to provide a therapeutic benefit in the treatment, reduction in occurrence, prevention, or management of a disease. The specific amount that is therapeutically effective can be readily determined by the ordinary medical practitioner, and can vary depending on factors known in the art, such as the type of disease/cancer, the patient's history and age, the stage of disease, and the co-administration of other agents.

A "disorder" is any condition that would benefit from treatment with the polypeptide. This includes chronic and acute disorders or diseases including those pathological conditions which predispose the mammal to the disorder in question.

The term "therapeutically effective amount" refers to an amount of a biologically active molecule or conjugate or derivative thereof sufficient to exhibit a desired therapeutic effect without undue adverse side effects (such as toxicity, irritation and allergic response) commensurate with a reasonable benefit/risk ratio when used in the manner of the inventive concepts. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease in conjunction with the pharmaceutical compositions of the present disclosure. This concurrent therapy can be sequential therapy, where the patient is treated first with one drug and then the other, or the two drugs are given simultaneously.

The terms "administration" and "administering," as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the present disclosure (and/or the methods of administration of same) may be designed to provide delayed, controlled or sustained release using formulation techniques which are well known in the art.

The terms "substitution," "insertion," "addition," and "deletion" are used herein with reference to amino acid or nucleotide sequences. A "substitution" refers to a replacement of one or more nucleotides or amino acids by different nucleotides or amino acids, respectively. An "insertion" or "addition" is that change in a nucleotide or amino acid sequence which has resulted in the addition of one or more nucleotides or amino acid residues, respectively, as compared to the naturally occurring sequence. A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions, or any combination thereof may be used to arrive at a final mutant polypeptide.

Generally, a few amino acids are changed to minimize the alteration of the molecule. However, larger changes may be tolerated in certain circumstances.

In certain embodiments, amino acid substitutions can be the result of replacing one amino acid with another amino acid having similar structural and/or chemical properties, such as the replacement of an isoleucine with a valine, i.e., conservative amino acid replacements. Insertions or deletions may optionally be in the range of 1 to 5 amino acids.

In embodiments, substitutions can be made in accordance with known "conservative substitutions." A "conservative substitution" refers to the substitution of an amino acid in one class by an amino acid in the same class, where a class is defined by common physicochemical amino acid side chain properties and high substitution frequencies in homologous proteins found in nature.

In contrast, in certain embodiments, substitutions are non-conservative. A "non-conservative substitution" refers to the substitution of an amino acid in one class with an amino acid from another class.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "nucleic acid molecule" includes RNA, DNA and cDNA molecules. It will be understood that, as a result of the degeneracy of the genetic code, a multitude of nucleotide sequences encoding a given mutant CDC protein may be produced. The present disclosure includes every possible variant nucleotide sequence thereof, all of which are possible given the degeneracy of the genetic code.

A "heterologous" nucleic acid construct or sequence has a portion of thereof which is not native to the cell in which it is expressed. The term "heterologous." with respect to a control sequence, refers to a control sequence (i.e., promoter or enhancer) that does not function in nature to regulate the same gene the expression of which it is currently regulating. Generally, heterologous nucleic acid sequences are not endogenous to the cell or are not part of the genome in which they are present; rather, the heterologous sequences have been added to the cell, such as by infection, transfection, transformation, microinjection, electroporation, or the like. A "heterologous" nucleic acid construct may contain a control sequence/DNA coding sequence combination that is the same as, or different from, a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The terms "chimeric gene" or "heterologous nucleic acid construct," as utilized herein, refer to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present disclosure, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "recombinant" includes reference to a cell or vector that has been modified by the introduction of a heterologous nucleic acid sequence; in addition, the term "recombinant" can also refer to a cell that is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the terms "transformed," "stably transformed," or "transgenic," with reference to a cell, means the cell has a non-native (heterologous) nucleic acid sequence integrated into its genome or has an episomal plasmid that is maintained through multiple generations.

As used herein, the term "expression" refers to the process by which a polypeptide is produced based on the nucleic acid sequence of a gene. The process includes both transcription and translation.

The term "introduced," in the context of inserting a nucleic acid sequence into a cell, refers to any method of insertion of a nucleic acid sequence into a cell, including but not limited to, "transfection," "transformation," and/or "transduction" methods. The term "introduced" also includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

Turning now to the present disclosure, certain embodiments are directed to compositions comprising one or more non-toxic mutants of cholesterol-dependent cytolysins (CDCs). The compositions may be used, for example, in vaccines directed against corresponding disease pathogens, or may be used in diagnostic or screening methods or other analytical methods such as detection methods.

The organisms which produce the native forms of the CDCs have various pathological effects, including but not limited to those listed below.

*Clostridium perfringens* is a causative agent of various human and animal diseases, often characterized by enterotoxemia or soft tissue infections such as gas gangrene. Experimental evidence suggests a role for perfringolysin O in blunting the immune response by affecting neutrophil function.

*Bacillus cereus* (source of Cereolysin O) is an infrequent cause of serious nongastrointestinal infection, particularly in drug addicts, the immunosuppressed, neonates, and postsurgical patients, especially when prosthetic implants such as ventricular shunts are inserted. Ocular infections are the commonest types of severe infection, including endophthalmitis, anophthalmitis, and keratitis, usually with the characteristic formation of corneal ring abscesses.

*Bacillus alvei* can cause endophthalmitis and may cause pneumonia and empyema.

*Streptococcus dysgalactiae* subsp. *equisimilis* has been shown to be involved in many different types of human disease syndromes.

*Streptococcus canis* typically causes disease in animals, primarily dogs. It can cause disease in humans, most often soft tissue infections, bacteremia, urinary infections, bone infections or pneumonia.

*Streptococcus* causes a variety of diseases including strep throat, rheumatic fever, soft tissue infections (i.e., the flesh-ing eating bacteria), and many others. Streptolysin O has been shown to be a major pathogenic factor in many of these diseases.

Tetanolysin is produced by *Clostridium* tetanus that is the cause of tetanus.

*Listeria ivanovii* is an infection of animals and primarily causes abortion in sheep.

*Listeria monocytogenes* causes food borne illness in humans; the most severe food borne illness caused thereby is a meningitis. It is especially problematic for pregnant women where the infection may be subclinical in the mother but fatal for the fetus. Listeriolysin is a critical pathogenic factor for these diseases, without it the bacterium is avirulent.

*Streptococcus suis* is a cause of septicemia, meningitis, endocarditis, arthritis and, occasionally, other infections in pigs, and is increasingly a problem in humans, more and more outbreaks are being reported with symptoms that include high fever, malaise, nausea and vomiting, followed by nervous symptoms, subcutaneous hemorrhage, septic shock and coma.

Certain embodiments of the present disclosure provide non-toxic mutants of native (wild type) pneumolysin ("PLY;" SEQ ID NO: 1) of *S. pneumoniae* (encoded by mutants of SEQ ID NO:20). These PLY mutants exhibit several potential advantages over the pneumolysin mutant (Pd-B) which has previously been used for vaccine development, particularly in that they substantially lack hemolytic activity in comparison to the wild type PLY protein. For example, the PLY mutants of the present disclosure lack the ability to bind to mammalian membranes, and thus will not undergo any of the structural changes that normally result when the wild type PLY toxin binds to the membrane (as does the Pd-B mutant (Trp433Phe) described above).

In certain non-limiting embodiments, the present disclosure includes pneumolysin mutants wherein at least one amino acid of positions 293 and 294 (of SEQ ID NO: 1), and at least one amino acid at positions 458, 459, and 460, have been substituted with a different amino acid than found in the wild-type PLY sequence (SEQ ID NO: 1). More particularly, either or both of the gly residues at positions 293 and 294 can be substituted with an amino acid having a side chain, including but not limited to ala, leu, ile, val, pro, trp, asn, gin, phe, tyr, met, cys, thr, ser, asp, glu, arg, his, and lys. Further, either or both of the thr residues at positions 458 and 459 can be substituted with gly, ala, leu, ile, val, pro, trp, asn, gin, phe, tyr, met, cys, ser, asp, glu, arg, his, and lys. Further, the leu residue at position 460 can be substituted with gly, ala, ile, val, pro, trp, asn, gin, phe, tyr, met, cys, thr, ser, asp, glu, arg, his, and lys. For example, in one non-limiting embodiment, the glycine at position 293 has been replaced with one of ala, leu, ile, val, pro, trp, asn, gin, phe, tyr, met, cys, thr, ser, asp, glu, arg, his, and lys, and the leucine at position 460 has been replaced with one of gly, ala, ile, val, pro, trp, asn, gin, phe, tyr, met, cys, thr, ser, asp, glu, arg, his, and lys. In particular non-limiting embodiments of a mutant pneumolysin, at least one of the glycine residues at positions 293 and 294 has been mutated to a serine or threonine residue, and at least one of the threonine, threonine, and leucine residues at positions 458, 459, and 460, respectively, has been mutated to an aspartate, asparagine, or glutamate residue. For example, when position 293 has been mutated to a serine, and the leucine at position 460 has been mutated to an aspartate, the pneumolysin mutant is designated PLY-G293S/L460D (or PLY-L460D/G293S); the amino acid sequence thereof is provided as SEQ ID NO:40. In alternate non-limiting embodiments, position 460 can be substituted with D, E or N. and position 293 can be substituted with S or T such that the double mutant may comprise a D, E, or N at position 460 and an S or T at position 293.

In addition to mutants of pneumolysin, the present disclosure provides mutants of other CDCs which have substitutions in analogous positions in Loop 1, Loop 2 and/or Loop 3 of Domain 4, including mutants of Cereolysin (*Bacillus cereus*), Anthrolysin (*Bacillus anthracis*), Thuringiolysin (*Bacillus thuringiensis*), Perfringolysin (*Clostridium perfringens*), Alveolysin (*Bacillus alvei*), Caniolysin (*Streptococcus canis*), Equisimilysin (*Streptococcus equisimilis*), Streptolysin O (*Streptococcus pyogenes*), Tetanolysin (*Clostridium tetani*), Ivanolysin (*Listeria ivanovii*), Listeriolysin (*Listeria monocytogenes*), Seeligeriolysin (*Listeria seeligeri*), Suilysin (*Streptococcus suis*), Mitilysin (*Streptococcus mitis*), Platelet aggregation factor (a.k.a. PAF and Viridanolysin) (*Streptococcus mitis*), Intermedilysin (*Streptococcus intermedius*), Pyolysin (*Arcanobacterium pyogenes*), and Novyiolysin, a.k.a., tetanolysin NT (*Clostridium novyi*).

Wild-type amino acid sequences of Cereolysin, Anthrolysin, Thuringiolysin. (a.k.a., Thuringolysin or Cereolysin form BT), Perfringolysin, Alveolysin, Caniolysin, Equisimilysin, Streptolysin O, Novyiolysin, Tetanolysin, Ivanolysin, Listeriolysin, Seeligeriolysin, Suilysin, Mitilysin, Intermedilysin, Platelet aggregation factor (a.k.a. Viridanolysin or PAF), and Pyolysin are shown in SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11 SEQ ID NO:12, SEQ ID NO:13, SEQ ID NO:14, SEQ ID NO:15, SEQ ID NO:16, SEQ ID NO:17, SEQ ID NO:18, and SEQ ID NO: 19, respectively.

Another embodiment of the present disclosure is directed to a mutant of Streptolysin O comprising substitutions in at least one of positions 561 and 562 and in at least one of positions 395 and 396 of SEQ ID NO:9 and which is at least 90% identical to the wild type Streptolysin O protein. The substitutions in positions 561 and 562 may be any substitution described herein that can be made in positions 458-460 of PLY (SEQ ID NO: 1), and the substitutions in positions 395 and 396 may be any substitution described herein that can be made in positions 293 or 294 of PLY.

A variant of SEQ ID NO:18 (Platelet Aggregation Factor) which can also be mutated in accordance with the present disclosure is Lectinolysin, which is also obtained from *Streptococcus mitis*. The amino acid sequences of L1, L2 and L3 are the same as PAF. Lectinolysin differs from PAF at 12 positions, including 67, 158, 211, 303, 305-307, 311, 319, 327, 447, and 556 wherein in Lecinolysin the amino acids at these positions are T, D, T, H, E, N, K, N, E, K, T and I, respectively. The present disclosure thus includes mutants of Lectinolysin which are similar to those of the other mutants contemplated herein, and nucleic acids encoding these mutants, and compositions comprising these mutants.

The pneumolysin mutants contemplated herein also eliminate any toxic activity of the toxin, since they cannot bind to mammalian cells. Although the pneumolysin mutant Pd-B is about 21,000 times less toxic than native pneumolysin, it still exhibits sufficient toxicity to be problematic in the development of any vaccines that include it. It appears that modern vaccine development against *S. pneumoniae* is centered on using pneumolysin with other *S. pneumoniae* derived proteins; thus it appears that regardless of the other proteins used in the vaccine, a pneumolysin will be included in all effective vaccines against *S. pneumoniae* because of its importance to disease establishment and progression.

As described below, it is shown in perfringolysin, a toxin related to pneumolysin, that the undecapeptide of the protein does not mediate binding of these toxins to the mammalian cell, contrary to the conventional wisdom. The structures that do mediate binding are three short hydrophobic loops that are juxtaposed to the undecapeptide. As part of the present disclosure, it is now known that if a negatively charged aspartate or glutamate residue (for example) is placed within any single hydrophobic loop (in a position not already comprising an aspartate or glutamate), binding of the CDC to the membrane is blocked. Hence, this single point mutation eliminates binding of the CDCs, including pneumolysin, to mammalian membranes. For example, a single asparate or glutamate residue substituted for leucine 460 of pneumolysin virtually completely abrogates its hemolytic activity. Since it is known in other systems (described below) that this mutation blocks binding to the membrane of cells, it substantially eliminates any toxic activity (making it at least 200 times less toxic than the Pd-B mutant for example), but also eliminates any possible side effects that might be caused by its binding to the surface of mammalian membranes.

In certain embodiments, the mutant pneumolysins of the present disclosure lack the hemolytic activity and the pore-forming ability present in a naturally occurring *S. pneumoniae* pneumolysin protein. Generally, the polypeptide component exhibits less than about 30%, less than about 20%, less than about 10%, less than about 5%, less than about 1%, less than about 0.1%, less than about 0.001%, or less of the hemolytic activity of a naturally occurring *S. pneumoniae* pneumolysin protein.

In certain embodiments, the mutant pneumolysins of the present disclosure have substitutions in one or more of three residues that flank either side of positions 293, 370, 406 or 460, including positions 290, 291, 292, 294, 295, 296, 367, 368, 369, 371, 372, 373, 403, 404, 405, 407, 408, 409, 457, 458, 459, 461, 462, and 463.

For example, these residues may be substituted with a negatively-charged amino acid, glutamate, or aspartate (except in position 403, which already comprises aspartate), or a positively charged amino acid lysine, arginine, or histidine (except in positions 367 and 407, which already comprise histidine residues). Alternatively, these residues may be substituted with any other natural amino acid (including gly, ala, leu, ile, val, pro, trp, asn, gln, phe, tyr, met, cys, thr, or ser) which abrogates the binding activity, pore-forming, and/or hemolytic activity of the mutant.

As noted above, the amino acid sequence for wild type pneumolysin is SEQ ID NO: 1, and the reverse complement of the cDNA which encodes the pneumolysin of SEQ ID NO: 1 is shown as SEQ ID NO:20. The present disclosure further includes cDNAs of mutant pneumolysins (and reverse complements thereof) and other mutant CDCs described herein which are substituted as necessary to encode the substituted proteins (mutants) described or otherwise enabled herein, and may in turn comprise any conservative base (nucleotide) substitution to make cDNAs which encode such mutants.

It will be appreciated that the polynucleotide sequences which encode the polypeptides contemplated herein may be altered with degenerate codons yet still encode the mutant polypeptides of the present disclosure. Accordingly, the present disclosure further provides polynucleotides which hybridize to the polynucleotide sequences described herein (or the complementary sequences thereof) having at least 90% identity between sequences, or at least 95% identity, or at least 99% identity.

FIGS. 1A through 1E show an alignment of the amino acid sequences of the native versions of the CDCs identified herein. The sequences are aligned along the three hydrophobic loops corresponding to positions 367-373 (second loop, L2), 403-409 (third loop, L3) and 457-463 (first loop, L1) of pneumolysin, represented in FIG. 1A-E as positions 586-592 (second loop, L2), 622-628 (third loop, L3), and 676-682 (first loop, L1). As noted above, certain particular (but non-limiting) embodiments of the mutants of these CDCs may comprise substitutions at one or more of these positions by the negatively-charged amino acids, glutamic acid, or aspartic acid (except wherein the position already has an aspartic acid), or by the positively-charged amino acids histidine, lysine, or arginine (except by a histidine where the position already has a histidine, by a lysine where the position already has a lysine, or by an arginine where the position already has an arginine) or by any of the other 15 natural amino acids noted above wherein the resulting mutant functions in accordance with the present disclosure.

The mutants may further comprise more than one of the substitutions described herein such that the mutant has 1, 2, 3, 4, 5, 6, or 7 substituted residues in a single loop (L1, L2, L3), or the mutant may have one or more (1 to 7) substituted residues in two of the loops (e.g., L1 and L2, L1 and L3, L2 and L3), or one or more substituted residues (1 to 7) in each of the three loops (L1, L2, and L3), wherein the substitutions are selected from those listed herein, for example, the mutant may have 1 to 7 substitutions in the first loop (L1), and/or 1 to 7 substitutions in the second loop (L2), and/or 1 to 7 substitutions in the third loop (L3). For example, in certain embodiments, where the native residue is positively-charged, the substituted residue may be negatively-charged, and where the native residue is negatively-charged, the substituted residue may be positively charged. Alternatively, aspartate may be substituted with glutamate, histidine, arginine, or lysine, or glutamate may be substituted with aspartate, lysine, histidine, or asparagine, or arginine may be substituted with a different positively-charged amino acid.

The amino acid positions of Loop 1, Loop 2, and Loop 3 of each CDC described herein is listed in Table 1.

TABLE 1

Amino Acid Positions Corresponding to Domain 4 Loops

| | SEQ ID NO. | Loop 1 | Loop 2 | Loop 3 |
|---|---|---|---|---|
| Pneumolysin | 1 | 457-463 | 367-373 | 403-409 |
| Cereolysin | 2 | 498-504 | 408-414 | 444-450 |
| Anthrolysin | 3 | 501-507 | 411-417 | 447-453 |
| Thuringiolysin | 4 | 501-507 | 411-417 | 447-453 |
| Perfringolysin | 5 | 488-494 | 398-404 | 434-440 |
| Alveolysin | 6 | 490-496 | 400-406 | 436-442 |
| Caniolysin | 7 | 562-568 | 472-478 | 508-514 |
| Equisimilysin | 8 | 559-565 | 469-475 | 505-511 |
| Streptolysin O | 9 | 559-565 | 469-475 | 505-511 |
| Novyiolysin | 10 | 502-508 | 412-418 | 448-454 |
| Tetanolysin | 11 | 514-520 | 424-430 | 460-466 |
| Ivanolysin | 12 | 512-518 | 422-428 | 458-464 |
| Listeriolysin O | 13 | 513-519 | 423-429 | 459-465 |
| Seeligeriolysin | 14 | 514-520 | 424-430 | 460-466 |
| Suilysin | 15 | 484-490 | 395-401 | 431-437 |
| Mitilysin | 16 | 457-463 | 367-373 | 403-409 |
| Intermedilysin | 17 | 515-521 | 425-431 | 461-467 |
| PAF | 18 | 651-657 | 561-567 | 597-603 |
| Pyolysin | 19 | 521-527 | 431-437 | 467-473 |

Thus, provided herein are purified or isolated forms of the protein mutants, and antigenic fragments thereof, immunogenic compositions of these mutants comprising pharmaceutically-acceptable excipients, adjuvants, and/or immunostimulants, and vaccines and sera comprising one or more of the mutants disclosed or otherwise contemplated herein. The mutants or antigenic fragments thereof can be used in analytical methods for detecting the presence of alternative forms of the proteins in biological samples using techniques known in the art, for example ELISA. The present disclosure further provides nucleic acids, host cells, and vectors comprising cDNAs encoding any of the mutants provided herein and methods of their use to produce the mutants contemplated herein. The present disclosure further provides methods of administering the immunogenic compositions for treatment of conditions, diseases, and infections, caused by the CDC-producing organisms described herein.

As noted above, the present disclosure is also directed to nucleic acid sequences which encode the mutant CDCs contemplated herein. The present disclosure provides nucleic acids which encode allelic variants of the protein mutants disclosed herein, wherein the allelic variants of the protein mutants differ from the protein mutants by less than 15% of their amino acid identity, for example, at least 85% of the amino acids of the allelic variant are identical to the protein mutant, and 100% of the amino acids in the first, second, and third loops (L1, L2, and L3) are identical to those in the protein mutant. For example, the allelic variants may differ from the protein mutants by less than 12% of their amino acid identity, by less than 10% of their amino acid identity, by less than 8% of their amino acid identity, by less than 6% of their amino acid identity, by less than 4% of their identity, by less than 2% of their amino acid identity, or by less than 1% of their amino acid identity from the protein mutants described herein. Further, the present disclosure is further directed to nucleic acids which hybridize under stringent conditions with the nucleic acids which encode the mutant CDCs described herein or with the complements of the nucleic acids encoding the mutant CDCs described herein.

In one aspect, the CDC mutant polypeptides or proteins of the present disclosure comprise an amino acid sequence having at least 90%, or at least 91%, or at least 92%, or at least 93%, or at least 94%, or at least 95%, or at least 96%, or at least 97%, or at least 98%, or at least 99%, or more percent identity to the sequence presented as SEQ ID NO: 1, (as determined by a sequence alignment program), and which have at least one of the mutations described elsewhere herein.

An alignment of selected sequences in order to determine "% identity" between two or more sequences, may be performed using, for example, the CLUSTAL-W program in MacVector version 6.5, operated with default parameters, including an open gap penalty of 10.0, an extended gap penalty of 0.1, and a BLOSUM 30 similarity matrix.

In another embodiment, the term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

The immunogenic compositions described or otherwise contemplated herein may include vaccine formulations that can be used in an amount effective to elicit (stimulate) a protective immune response in an animal. For example, the generation of a protective immune response can be measured by the development of antibodies. In certain non-limiting embodiments, the amounts of the mutant CDCs contemplated herein that can form a protective immune response typically are in a unit dosage form of about 0.001 μg to 100 mg per kg of body weight, such as but not limited to, about 0.01 μg to 1 mg/kg of body weight, or about 0.1 μg to about 10 μg/kg body weight, for example, at an interval of about 1 to 6 weeks between immunizations.

The present disclosure further provides methods of stimulating an immune response against at least one disease organism. In the method, any of the immunogenic compositions disclosed herein can be administered to a patient infected with the disease organism or predisposed to infection with the disease organism. In one non-limiting embodiment, the immunogenic composition comprises a pneumolysin mutant having mutations in positions 293 and 460, such as $PLY_{L460D/G293S}$ (SEQ ID NO:40). In the method, the immunogenic composition is substantially non-toxic (or substantially non-toxic compared to the native PLY protein), does not substantially bind to cell membranes, is substantially non-hemolytic, and/or is as stable as or is substantially more stable than the PLY protein.

The present disclosure is further directed to at least one method of decreasing the occurrence and/or severity of infection in a patient. In the method, any of the immunogenic compositions disclosed or otherwise contemplated herein is administered to an infected patient or a patient predisposed to infection. In one non-limiting embodiment, the immunogenic composition comprises a pneumolysin mutant having mutations in positions 293 and 460, such as $PLY_{L460D/G293S}$ (SEQ ID NO:40). In the method, the immunogenic composition is substantially non-toxic (or substantially non-toxic compared to the native PLY protein), does not substantially bind to cell membranes, is substantially non-hemolytic, and/or is as stable as or is substantially more stable than the native PLY protein. In certain embodiments, the mutant pneumolysin polypeptides disclosed herein have about 100,000-fold less hemolytic activity than wild type pneumolysin polypeptide. In other embodiments, the mutant pneumolysin polypeptides disclosed herein have about 150,000-fold less hemolytic activity than wild type pneumolysin polypeptide. In other embodiments, the mutant pneumolysin polypeptides disclosed herein have about 200,000-fold less hemolytic activity than wild type pneumolysin polypeptide. In still other embodiments, the mutant pneumolysin polypeptides disclosed herein have about 250.000-fold less hemolytic activity than wild type pneumolysin polypeptide. In at least certain embodiments, the purified mutant pneumolysin polypeptides disclosed herein which have at least two substitutions in amino acid positions 293, 294, 458, 459, and 460, also have an increased yield upon purification over a mutant pneumolysin polypeptide having a substitution in only one of amino acid positions 293, 294, 458, 459, and 460. The increased recombinant yield may be for example, at least about 10×, at least about 15×, at least about 17×, or at least about 20×.

The immunogenic compositions disclosed herein may be administered to animals which are infected or may become infected by the disease organisms described herein, including but not limited to dogs, cats, rabbits, rodents, horses, livestock (e.g., cattle, sheep, goats, and pigs), zoo animals, ungulates, primates, and humans.

As noted above, when the mutant is a pneumolysin mutant, the present disclosure includes an immunogenic composition (such as, but not limited to, a vaccine) which can be administered to a subject for stimulating an immunogenic response in the subject. In addition to the one or more pneumolysin mutants, the immunogenic composition/vaccine may comprise other proteins or protein subunits from *S. pneumoniae*, or may comprise capsular polysaccharide material combined with or conjugated to the pneumolysin mutants or other proteins in the immunogenic composition/vaccine. For example, the capsular material may be derived from any one or more of the *S. pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, 24F, 27, 33F, or 34, or others known in the art. As noted, the immunogenic composition/vaccine may comprise an adjuvant and/or other pharmaceutically-acceptable excipients. Polysaccharides can be conjugated to the mutant, for example, via a monomeric linkage (only one end of the polysaccharide is attached to the polypeptide), a looped linkage (a single polypeptide is attached to looped polysaccharides), or a cross-linkage (multiple polysaccharides attached to multiple polypeptides).

The immunogenic compositions or vaccines containing mutant pneumolysin polypeptides of the present disclosure, or fragments thereof, may be used to treat diseases and conditions related to *Streptococcus pneumoniae*, such as, but not limited to, pneumonia, meningitis, bacteremia, and otitis media.

In certain embodiments, the mutant CDCs disclosed herein are useful for causing stimulation of T-cell proliferation or the generation of antibodies through the stimulation of B cells.

As noted above, an immunogenic composition of the present disclosure can be formed by combining the mutant CDCs contemplated herein with a pharmaceutically (physiologically) acceptable excipient, such as (but not limited to) physiological saline or buffered saline solutions at neutral pH (such as phosphate buffered saline).

The present disclosure also includes antigenic fragments of the mutant CDCs described or otherwise contemplated herein. For example, for vaccine compositions, fragments are large enough to stimulate a protective immune response. The polypeptide component must be of a length sufficient to induce such an enhanced immune response. For fragments of a naturally occurring CDC protein, the fragments are at least about 8, at least about 10, at least about 25, at least about 50, at least about 75, at least about 100, at least about 125, at least about 150, at least about 175, at least about 200, at least about 250, at least about 300, at least about 350, at least about 400, at least about 425, at least about 450, at least about 460, at least about 465, or more amino acids in length.

Fragments may comprise peptide portions from different locations of the mutants that have been joined together. In certain particular (but non-limiting) embodiments, fragments include one or more of the three loops discussed herein.

The mutant CDCs disclosed or otherwise contemplated herein are also useful to generate neutralizing antibodies which can be used as a passive immune serum to treat or ameliorate symptoms in patients. An immunogenic composition as described above could be administered to an animal (such as a horse or a human) until a neutralizing antibody response is generated. These neutralizing antibodies can then be harvested, purified, and utilized to treat patients exhibiting symptoms.

Such neutralizing antibodies are administered to patients exhibiting disease symptoms in an amount effective to neutralize the effect of the pathogen. The neutralizing antibodies can be administered intravenously, intramuscularly, intradermal, subcutaneously, and the like. A particular route is intravenously, or for localized infection, topically at the site of tissue damage with debridement. The neutralizing antibody may also be administered in conjunction with antibiotic therapy. The neutralizing antibody can be administered until a decrease in shock or tissue damage is obtained in a single dose or multiple doses. The amount of neutralizing antibodies typically administered is about 1 mg to about 1000 mg antibody per kg of body weight, such as but not limited to, about 50 mg to about 200 mg antibody per kg of body weight.

The immunogenic compositions of the present disclosure may be prepared as a pharmaceutical composition containing an immunoprotective, non-toxic amount of at least one of the presently disclosed mutant proteins in a non-toxic and sterile pharmaceutically acceptable excipient.

The immunogenic compositions of the present disclosure can be administered to the appropriate subject in any suitable manner known in the art, including (but not limited to) orally intramuscularly, intravenously, sublingual mucosal, intraarterially, intrathecally, intradermally, intraperitoneally, intranasally, intrapulmonarily, intraocularly, intravaginally, intrarectally, and/or subcutaneously. They can be introduced into the gastrointestinal tract or the respiratory tract, e.g., by inhalation of a solution or powder containing the immunogenic composition. Parenteral administration, if used, is generally characterized by injection. Injectables can be prepared in conventional forms, either as liquid solutions or suspensions, solid forms suitable for solution or suspension in liquid prior to injection, or as emulsions.

An immunogenic composition (e.g., a vaccine) is administered in an amount sufficient to elicit production of antibodies as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill. In certain embodiments, a non-limiting range of effective amounts of a mutant CDC that may be administered to a subject is, for example, about 10 ng of protein to 100 mg per kg of body weight, such as about 0.1 μg of protein to about 1 mg per kg body weight. In at least one non-limiting embodiment, the dosage provided is in a range of from about 0.25 μg to about 25 μg of protein, with or without adjuvants.

When the immunogenic composition is administered parenterally, via the intramuscular or deep subcutaneous route, the mutant protein may (in certain particular but non-limiting embodiments) be admixed or absorbed with any conventional adjuvant to attract or to enhance the immune response. Such adjuvants include but are not restricted to aluminum hydroxide, aluminum phosphate, muramyl dipeptide, bacterial lipopolysaccharides and derivatives and purified saponins from QuilA. The protein can also be presented to the immune system within microparticles such as liposomes or immunostimulating complexes (ISCOMs). As noted, a formulation containing the mutant protein/peptide fragments of the present disclosure may be designed for oral or intranasal ingestion.

The therapeutically effective and non-toxic dose of the immunogenic compositions of the present disclosure can be determined by a person of ordinary skill in the art. For example, the specific dose for any subject can depend upon a variety of factors including (but not limited to) age, general health, diet of the patient, time and route of administration, synergistic effects with other drugs being administered, and whether the immunogenic composition is administered repeatedly. If necessary the immunogenic composition will be administered repeatedly with one to three month intervals between each dose and with an optional booster dose later in time. Actual methods of preparing the appropriate dosage forms are known, or will be apparent, to those skilled in this art; see, for example, Remington's Pharmaceutical Sciences latest edition.

As noted above, the present disclosure includes polynucleotides which encode the herein-described mutant polypeptides and active fragments of the present disclosure. The polynucleotides may be in the form of RNA or in the form of DNA (including, but not limited to, cDNA, genomic DNA, and synthetic DNA). The DNA may be double-stranded or single-stranded, and if single stranded, may be the coding strand or non-coding (anti-sense) strand.

Shown in Table 2 are DNA sequences (and corresponding amino acid sequences) which directly encode (or encode via the reverse complement) the native sequences of the CDCs contemplated herein and thus which also may be mutated to form the mutant forms described or otherwise contemplated herein.

TABLE 2

Amino Acid and Nucleic Acid Sequences of Native CDC Forms

| | SEQ ID NO: (Amino Acids) | SEQ ID NO: (Nucleic Acid) |
|---|---|---|
| Pneumolysin | 1 | 20 |
| Cereolysin | 2 | 21 |
| Anthrolysin | 3 | 22 |
| Thuringiolysin | 4 | 23 |
| Perfringolysin | 5 | 24 |
| Alveolysin | 6 | 25 |
| Caniolysin | 7 | 26 |
| Equisimilysin | 8 | 27 |
| Streptolysin O | 9 | 28 |
| Novyiolysin | 10 | 29 |
| Tetanolysin | 11 | 30 |
| Ivanolysin | 12 | 31 |
| Listeriolysin O | 13 | 32 |
| Seeligeriolysin | 14 | 33 |
| Suilysin | 15 | 34 |
| Mitilysin | 16 | 35 |
| Intermedilysin | 17 | 36 |
| PAF | 18 | 37 |
| Pyolysin | 19 | 38 |

Host cells are genetically engineered (transduced, transformed, and/or transfected) with the vectors comprising a polynucleotide encoding a mutant polypeptide of the present disclosure. The vector may be, for example, in the form of a plasmid, a viral particle, a phage, etc. The engineered host cells can be cultured in conventional nutrient media that can be modified as appropriate for activating promoters, selecting transformants, or amplifying the polynucleotides which encode such polypeptides. The culture conditions, such as temperature, pH, and the like, are those previously used with the host cell selected for expression, and will be apparent to the ordinarily skilled artisan. Vectors include chromosomal, nonchromosomal, and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter, and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, in certain non-limiting embodiments, the expression vectors contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the proteins.

As representative (but non-limiting) examples of appropriate hosts, there may be mentioned: bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; plant cells, etc. The selection of an appropriate host cell is deemed to be within the scope of those skilled in the art from the teachings herein.

More particularly, the present disclosure also includes recombinant constructs comprising one or more of the sequences as described and enabled herein. The constructs comprise a vector, such as a plasmid or viral vector, into which a polynucleotide sequence has been inserted in a forward or reverse orientation. In one non-limiting embodiment, the construct further comprises regulatory sequences, including, for example, a promoter operably linked to the sequence. Large numbers of suitable vectors and promoters are known to those of skill in the art, and are commercially available. The following vectors are provided by way of non-limiting example. Bacterial: pQE70, pQE60, pQE-9 (Qiagen, Inc., Hilden, Germany), pBS, pD10, phagescript, psiX174, pbluescript SK, pBS, pNH8A, pNH16a, pNH18A, pNH46A (Stratagene, San Diego, Calif.); ptrc99a, pKK223-3, pKK233-3, pDR540, pRIT5 (Pharmacia, Stockholm, Sweden). Eukaryotic: pWLNEO, pSV2CAT, pOG44, pXT1, pSG (Stratagene, San Diego, Calif.) pSVK3, pBPV, pMSG, pSVL (Pharmacia, Stockholm, Sweden). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacd, lacZ, T3, T7, gpt, lambda $P_R$, $P_L$, and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present disclosure includes host cells containing the above-described constructs. The host cell can be a higher eukaryotic cell, such as (but not limited to) a mammalian cell; a lower eukaryotic cell, such as (but not limited to) a yeast cell; or a prokaryotic cell, such as (but not limited to) a bacterial cell. Introduction of the construct into the host cell can be effected by calcium phosphate transfection, DEAE-Dextran mediated transfection, electroporation (Davis et al., Basic Methods in Molecular Biology (1986) Elsevier Science Publishing Co., Inc., New York, N.Y.), or any other suitable technique.

The constructs in host cells can be used in a conventional manner to produce the gene product encoded by the recombinant sequence. Alternatively, the polypeptides of the present disclosure can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present disclosure. Appropriate cloning and expression vectors for use with prokaryotic and eukaryotic hosts are described by Green and Sambrook (Molecular Cloning: A Laboratory Manual, Fourth Edition, Cold Spring Harbor, N.Y., (2012)), the entire disclosure of which is hereby incorporated by reference.

Transcription of the DNA encoding the mutant polypeptides of the present disclosure by higher eukaryotes can be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host.

As a representative but non-limiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Amersham Pharmacia Biotech, Piscataway, N.J., USA) and pGEM1 (Promega, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction), and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a French press, mechanical disruption, or use of cell lysing agents, such methods are well known to those skilled in the art. However, it may be desired (but non-limiting) to use host cells which secrete the polypeptides of the present disclosure and permit recovery of the polypeptide from the culture media.

Various mammalian cell culture systems can also be employed to express recombinant protein. Examples of mammalian expression systems include the COS-7 lines of monkey kidney fibroblasts, described by Gluzman (Cell (1981) 23:175), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The mutant polypeptides that are useful as immunogens in the present disclosure may be products of chemical synthetic procedures, or products of recombinant techniques from a prokaryotic or eukaryotic host (for example, by bacterial, yeast, higher plant, insect, and mammalian cells in culture), as explained previously. Depending upon the host employed in a recombinant production procedure, the mutant polypeptides of the present disclosure may be glycosylated or may be non-glycosylated.

The individually expressed polypeptides may be isolated by recombinant expression/isolation methods that are well-known in the art. Typical examples for such isolation methods may utilize an antibody to a conserved area of the protein or to a His tag or cleavable leader or tail that is expressed as part of the protein structure.

As noted, fragments and variants of the CDC mutant proteins disclosed or otherwise contemplated herein are considered to be a part of the present disclosure. A fragment is a variant polypeptide which has an amino acid sequence that is entirely the same as part, but not all, of the amino acid sequence of the native or mutant polypeptides. The fragments can be "free-standing" or contained within a larger polypeptide of which the fragment forms a part or a region, such as (but not limited to) as a single continuous region. Particular non-limiting fragments are biologically active fragments which are those fragments that mediate activities of the polypeptides of the present disclosure, including those with similar activity or improved activity or with a decreased activity. Also included are those fragments that are antigenic or immunogenic in an animal, particularly a human. In this aspect, the present disclosure includes: (i) fragments of a mutant CDC, for example (but not by way of limitation) at least about 20-100 amino acids in length, or about 100-200 amino acids in length, and (ii) a pharmaceutical composition comprising the mutant fragment.

In one embodiment, the nucleic acids which encode the CDC mutants described herein are hybridizable to the corresponding native sequence under high stringency hybridization conditions. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

Nucleic Acid Constructs/Expression Vectors

As noted, the nucleic acids contemplated herein may be incorporated into heterologous nucleic acid constructs or vectors that are capable of introduction into and replication in a host cell. Any vector may be used as long as it is replicable and viable in the cells into which it is introduced. Large numbers of suitable vectors and promoters are known to those of skill in the art, and are commercially available. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Heterologous nucleic acid constructs of the present disclosure may include the coding sequence for the mutant CDCs contemplated herein or fragments thereof: (i) in isolation; (ii) in combination with additional coding sequences, such as (but not limited to) fusion protein or signal peptide coding sequences, where the mutant CDC coding sequence is the dominant coding sequence; (iii) in combination with non-coding sequences, such as (but not limited to) introns and control elements, such as promoter and terminator elements or 5' and/or 3' untranslated regions, effective for expression of the coding sequence in a suitable host; and/or (iv) in a vector or host environment in which the mutant CDC coding sequence is a heterologous gene.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available.

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system, the beta actin promoter and the metallothionein promoter that can upregulated by addition of certain metal salts. A promoter sequence is a DNA sequence which is recognized by the host cell for expression purposes. It is operably linked to the DNA sequence encoding the mutant polypeptide.

Unless otherwise indicated, the practice of the compositions and methods of the present disclosure employs conventional techniques of molecular biology, microbiology, recombinant DNA, and immunology, which are within the skill of one of ordinary skill in the art.

EXAMPLES

Examples are provided hereinbelow. However, the embodiments of the present disclosure are not limited in application to the specific experimentation, results and laboratory procedures described herein. Rather, the Examples are simply provided as among various embodiments and are meant to be exemplary, not exhaustive, and it will be appreciated that additional and different embodiments of the teachings of the present disclosure will doubtless suggest themselves to those of skill in the art; therefore, such other embodiments are considered to have been inferred from the disclosure herein.

Example 1

Figure 2:
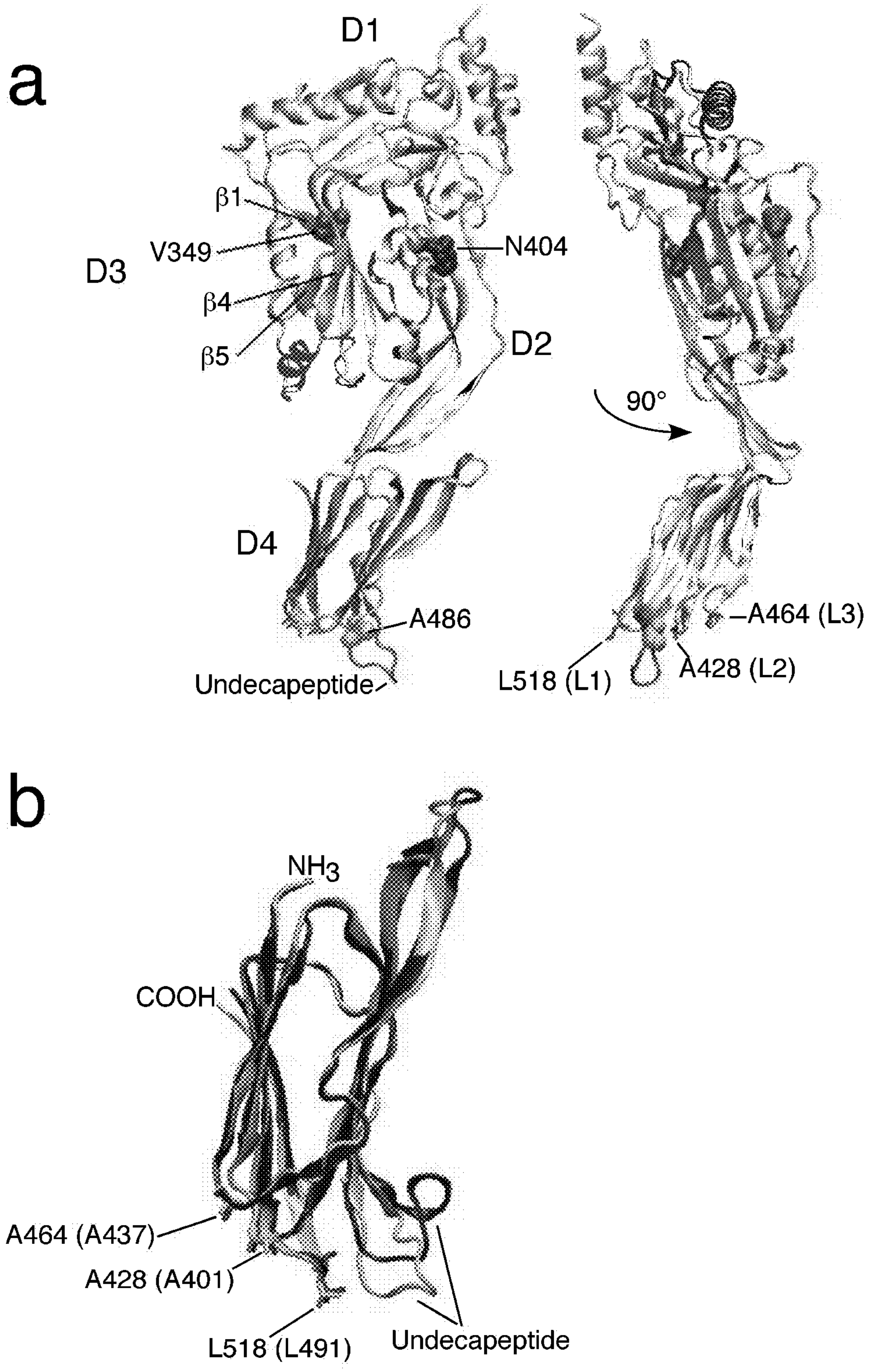
FIG. 2 shows the crystal structure of ILY (Intermedilysin) and a comparison of the D4 crystal structures of ILY and PFO (Perfringolysin). Shown in (a) is a ribbon representation of the crystal structure of ILY[25] denoting the positions of various structures and residues referred to in these studies. Shown in (b) is an overlay of a ribbon representation of the D4 structures of ILY and PFO based on the crystal structures of both proteins[23, 24]. Shown are the relative locations of the undecapeptide for both proteins and the L1-L3 loops residues of ILY and PFO (the latter in parentheses). The structural images were generated using VMD[25].

The cholesterol dependent cytolysins (CDCs) are a large family of pore-forming polypeptide toxins produced by more than 20 different species of Gram-positive bacteria[1]. Initially, the bacteria secrete these toxins as stable water-soluble monomers. The monomer binds to membranes and undergoes a specific sequence of structural changes, which promotes oligomerization and pore formation. As the name indicates, the CDC pore forming mechanism is absolutely dependent upon membrane cholesterol for its pore-forming mechanism. The dogma for several decades has been that cholesterol is the receptor for these toxins and that the conserved undecapeptide, located in domain 4 (D4) of the CDCs (FIG. 2), is important to the interaction of the CDCs with cholesterol[2-4]. However, other studies have suggested that the undecapeptide does not mediate the initial binding of these CDCs to cholesterol-rich membranes[5,6]. Hence, the structural components of these CDCs that mediate their binding to cholesterol have been vague prior to the present work.

The sensitivity of the CDC mechanism to oxidation has been known for over 80 years[7], and this trait was responsible for the title of "thiol-activated cytolysins" that was originally given to these toxins (reviewed in reference 8). The oxidation of this thiol group results in a significant loss of cytolytic activity, often >99%[2]. It was subsequently shown via sequence analysis of a great number of the CDCs that the cysteine having the sensitive thiol group resided in the conserved undecapeptide (E<u>C</u>TGLAWEWWR-SEQ ID NO:39), since this is the only cysteine present in most sequenced CDCs. The loss of cytolytic activity associated oxidation of this thiol group has been suggested to result from alterations in binding to cholesterol-rich membranes[2], thus establishing a putative link between membrane binding and the undecapeptide. The highly conserved nature of the undecapeptide also suggested a highly conserved function, perhaps mediating a direct interaction with membrane cholesterol.

The dogma that cholesterol is the receptor for the CDCs was complicated by the discovery of intermedilysin (ILY), a CDC that is secreted by *Streptococcus intermedius*. In contrast to other CDCs, ILY is human cell specific[9,10], a feature that is explained by its ability to specifically bind to human CD59, a species-specific inhibitor of the complement membrane attack complex[11,12], rather than cholesterol-rich membranes[13]. Therefore, at least two classes of CDCs now exist, ILY that binds to a specific non-sterol receptor and PFO-like CDCs that bind directly to cholesterol-rich membranes. Yet, the cytolytic mechanisms of both types of CDCs are sensitive to membrane cholesterol and neither is active on membranes that are substantially depleted of cholesterol[14]. These studies, therefore, presented an enigma; does cholesterol contribute to the ILY mechanism in a significantly different way than to the PFO-like CDCs, or is there a unifying molecular basis for the contribution of cholesterol to both classes of CDCs?

Giddings et al.[14] showed that cholesterol-depletion of hRBC membranes blocked prepore to pore conversion for all CDCs, but also affected binding of PFO-like CDCs, to the membrane. Soltani et al.[15] showed that disrupting the membrane insertion of the L1-L3 D4 loops (FIG. 2) of ILY also blocks prepore to pore conversion. Therefore, two distinct phenomena block prepore to pore conversion in ILY, depletion of membrane cholesterol[14] and disruption of the membrane insertion of the L1-L3 loops[15].

Based on these observations, a detailed investigation of the interaction of the D4 loops and undecapeptide of ILY and PFO with membranes was performed. The results of these studies indicate that the L1-L3 loops at the base of domain 4 are the primary structures that recognize cholesterol-rich membranes, rather than the undecapeptide. The interaction of these loops with cholesterol-rich membranes mediates the interaction of PFO with cholesterol-rich membranes whereas their insertion into the membrane is also necessary for the prepore to pore conversion of both PFO and ILY. Hence, these results now provide the structural basis for cholesterol sensitivity of the CDCs and provide a unifying explanation for the effect of cholesterol on both ILY and PFO-like CDCs, which use different membrane receptors.

Materials and Methods of Example 1

Bacterial Strains, Plasmids, and Chemicals

The genes for ILY and PFO were cloned into pTrcHisA (Invitrogen) as described previously[14,16]. All mutations were made in the native ILY (naturally cysteine-less) or the cysteine-less PFO ($PFO^{C459A}$) background. Native PFO contains a cysteine at residue 459 that has been changed to alanine to generate the cysteine-less PFO derivative $PFO^{C459A}$. Both PFO and $PFO^{C459A}$ exhibit similar cytolytic activities[16]. All chemicals and enzymes were obtained from Sigma, VWR, and Research Organics. All fluorescent probes were obtained from Molecular Probes (Invitrogen).

Generation and Purification of ILY and its Derivatives

Using PCR QuikChange mutagenesis (Stratagene), various amino acid substitutions were made in native ILY or $PFO^{C459A}$. DNA sequences of the mutant versions of the ILY gene were analyzed by the Oklahoma Medical Research Foundation Core DNA Sequencing Facility. The expression and purification of recombinant ILY and its derivatives from *Escherichia coli* were carried out as described[15,16]. The eluted protein was dialyzed into buffer (300 mM NaCl, 10 mM MES, 1 mM EDTA, pH 6.5) overnight at 4° C. The protein was then stored in 5 mM DTT and 10% (vol/vol) sterile glycerol at −80° C.

Chemical Modification of ILY and PFO and their Derivatives with Sulfhydryl Specific Reagents.

The cysteine derivatives of ILY were modified with the environmentally sensitive probe iodoacetamido-N,N'-dimethyl-N-(7-nitrobenz-2-oxa-1,3-diazolyl)ethylene-diamine (NBD) via the sulfhydryl group. The reaction was carried out as previously described[14]. The modified protein was stored in 10% (vol:vol) sterile glycerol, quick frozen in liquid nitrogen, and stored at −80° C. Proteins were labeled at an efficiency of 75% or greater.

Fluorescence Measurements

All fluorescence intensity measurements were performed using an SLM-8100 photon counting spectrofluorimeter as previously described[16]. For NBD measurements, an excitation wavelength of 460-480 nm and an emission wavelength of 540 nm were used with a bandpass of 4 nm. Emission scans from 500-600 nm for each sample were carried out at a resolution of 1 nm with an integration time of 1 s. Samples containing 10 μg of total toxin were incubated with human red blood cell (hRBC) ghost membranes (equivalent to 303.25 μg of membrane protein) in PBS [10 mM $Na_2HPO_4$, 2 mM $KH_2PO_4$, 137 mM NaCl, 3 mM KCl (pH 7.5)] at 37° C. for 5-10 minutes before making spectral measurements.

Liposome Preparation

Liposomes containing 1-palmitoyl-2-oleoyl-sn-glycero-3-phosphocholine (POPC; Avanti Polar Lipids) and cholesterol at a ratio of 45:55 mol % were prepared as described[16].

HRBC Ghost Membrane Preparation

HRBC ghost membranes were prepared as previously described. Membrane protein content was quantified using the Bradford method (Bio-Rad Protein Assay, Bio-Rad Laboratories, Inc.) also previously described[14].

Cholesterol Depletion and Repletion

Cholesterol extraction was performed with methyl-β-cyclodextrin (MβCD) as previously described[14]. Briefly, human huRBC ghost membranes were incubated with a final concentration of 20 mM-40 mM MβCD (made fresh for each use) at 37° C. for 2 hours. The membranes were washed three times by repeated centrifugation (14,000 rpm for 20 min at 4° C.) and resuspended in PBS to remove excess MβCD. Ghost membranes were finally suspended in PBS. Cholesterol content was measured using Cholesterol/Cholesteryl Ester Quantitation Kit (Calbiochem, Billerica, Mass.). Typically the cholesterol content of the membranes was decreased >90% by this method.

Cholesterol repletion was performed using cholesterol loaded MβCD. This method has been described previously[14]. Briefly, freshly made MβCD was added to buffer A (140 mM NaCl, 5 mM KCl, 5 mM $KH_2PO_4$, 1 mM $MgSO_4$, 10 mM HEPES, 5 mM glucose, pH 6.5) to a final concentration of 5 mM. 100 mM stock of cholesterol was made in a 1:2 (vol/vol) of chloroform:methanol. Buffer A+MβCD was heated to 80° C. in a glass container. Once heated to 80° C., suspended cholesterol was added to a final concentration of 4 mM. The solution was homogenized by sonication (4×20 s). Then the solution was filtered using 0.22 μm filter. MβCD loaded with cholesterol was added to pelleted cholesterol depleted ghost membranes and incubated for 2 hours at 37'C. The membranes were washed by repeated centrifugation as before and finally, resuspended in PBS.

Immobilization of Liposomes on L1 SPR Sensor Chip

Surface plasmon resonance (SPR) was measured with a BIAcore 3000 system using a L1 sensor chip (BIAcore, Uppsala, Sweden). The L1 sensor chip contains a dextran matrix to which hydrophobic residues are covalently bound and has routinely been used for immobilization of liposomes. In preparation of the L1 chip for liposomes, 10 μl of 20 mM CHAPS was injected at a flow rate of 10 μl/min. Liposomes (0.5 mM final lipid concentration) were then injected at the same flow rate for 10 min. After injection of liposomes, 50 mM NaOH was injected for 3 min to remove the multiple layers of lipids. This was followed by injection of 0.1 mg/ml BSA to coat the nonspecific binding sites. All injections were performed at 25° C. The L1 chip was regenerated and striped of liposomes by repeated injections of 20 mM CHAPS and 50 mM NaOH until original RU reading was reached. The regeneration procedure did not result in loss of sensor chip binding capacity.

SPR Analysis

All analysis of interaction between the liposomes and PFO derivatives were performed in HBS at 25° C. Wild type PFO (50 ng/μl) and the PFO aspartate mutants (50 ng/μl) were injected over the liposome coated chip at a flow rate of 30 μl/min for 4 mins.

Results of Example 1

Experimental Strategy.

ILY does not depend on membrane cholesterol to bind to native membranes, but its mechanism still remains sensitive to cholesterol. Unlike the PFO-like CDCs that do not bind to membranes that lack cholesterol, receptor binding, and oligomerization of ILY still occurs on cholesterol-depleted membranes[14]. Therefore, ILY was used to first identify structures that were responsible for its cholesterol-dependence. Once the structures of ILY that were sensitive to membrane cholesterol were identified, the effect of disrupting these structures was examined in PFO on its ability to bind to cholesterol-rich liposomal membranes. In this way it could be determined if the same structures in both ILY and PFO were responsible for their cholesterol dependence.

Cholesterol is not Required for the Membrane Insertion of the ILY Undecapeptide.

Figure 3:
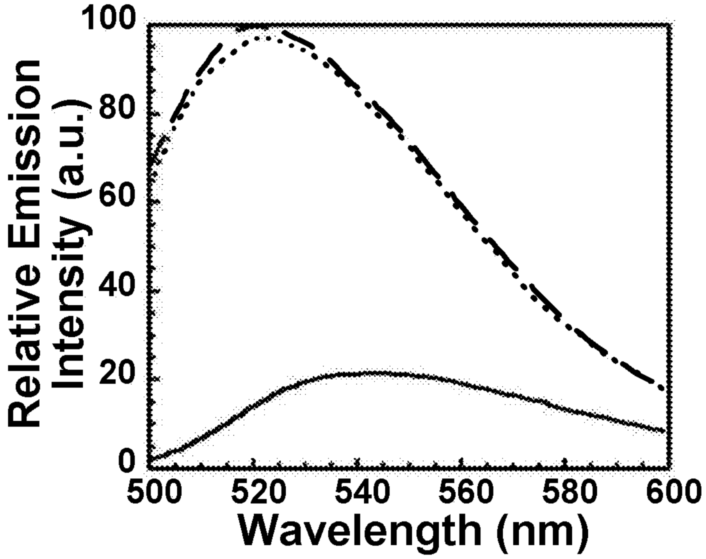
FIG. 3 illustrates that the ILY undecapeptide inserts into cholesterol-depleted membranes. ILY residue Ala-486 was mutated to a cysteine ($ILY^{A486C}$) and derivatized with NBD (iodoacetamido-N,N'-dimethyl-N-(7-nitrobenz-2-oxa-1,3-diazolyl)ethylene-diamine). The fluorescence emission of the NBD was determined when $ILY^{A486C\text{-}NBD}$ was incubated alone (solid line), with human red blood cells (hRBCs-dashed line), or with hRBCs depleted of cholesterol (dotted line).

Previous studies with ILY have shown the undecapeptide must insert into the membrane in order for the prepore to form[15]. Therefore, it was determined whether or not its insertion was sensitive to membrane cholesterol. A cysteine residue was substituted for Ala-486, which is located within the undecapeptide, and labeled with NBD via its sulfhydryl group. This residue has been shown to insert into the membrane in native ILY[15]. The fluorescence intensity of the NBD in $ILY^{A486C\text{-}NBD}$ was measured in the absence and presence of cholesterol-containing membranes or cholesterol-depleted membranes. As shown in FIG. 3, in the presence of hRBC ghost membranes, the undecapeptide inserts into the membrane as shown by the increase in fluorescence emission intensity compared to that observed for ILY in its soluble state. When the membrane is depleted of cholesterol, the same increase in fluorescence emission is observed. These results demonstrate that the membrane insertion of the undecapeptide region near Ala-486 is independent of membrane cholesterol content.

Cholesterol is Required for the Insertion of Loops L1, L2, and L3.

The membrane insertion of the three short hydrophobic loops at the tip of D4 (FIG. 2) occurs in concert and is required to anchor and properly orient the CDC monomers on the membrane[15,17]. Their insertion, in concert with the insertion of the undecapeptide, is necessary for the subsequent membrane insertion of the D3 transmembrane β-hairpins (TMHs) that leads to the formation of the transmembrane β-barrel pore[15]. Cholesterol is also required for the insertion of the TMHs and formation of the pore complex[14]. Hence, both membrane cholesterol and the membrane insertion of the L1-L3 loops are prerequisites for prepore to pore conversion[14,15]. Since the membrane insertion of the L1-L3 loops precedes the insertion D3 TMHs, it appeared reasonable that the depletion of membrane cholesterol may block the insertion of the L1-L3 loops that, in turn, would prevent the insertion of the D3 TMHs and block prepore to pore transition. Therefore it was hypothesized that cholesterol is required for membrane insertion of the L1-L3 loops.

To test this hypothesis, the membrane insertion of the L1-L3 loops into native and cholesterol-depleted huRBC ghost membranes was measured individually. It was recently shown that the ILY residues Leu-518, Ala-424 and Ala-464, located within loops L1, L2, and L3, respectively, insert into the membrane[17]. To measure insertion of each loop, a residue in each loop was mutated to a cysteine ($ILY^{A428C}$, $ILY^{A464C}$, $ILY^{L518C}$)[15], and the sulfhydryl group derivatized with NBD. As the NBD located at these sites enters the membrane, its fluorescence emission intensity increases significantly[15,17]. The emission intensity of the NBD was compared between soluble monomeric toxin, toxin bound to huRBC ghost membranes, and toxin bound to cholesterol-depleted ghost membranes.

Figure 4:
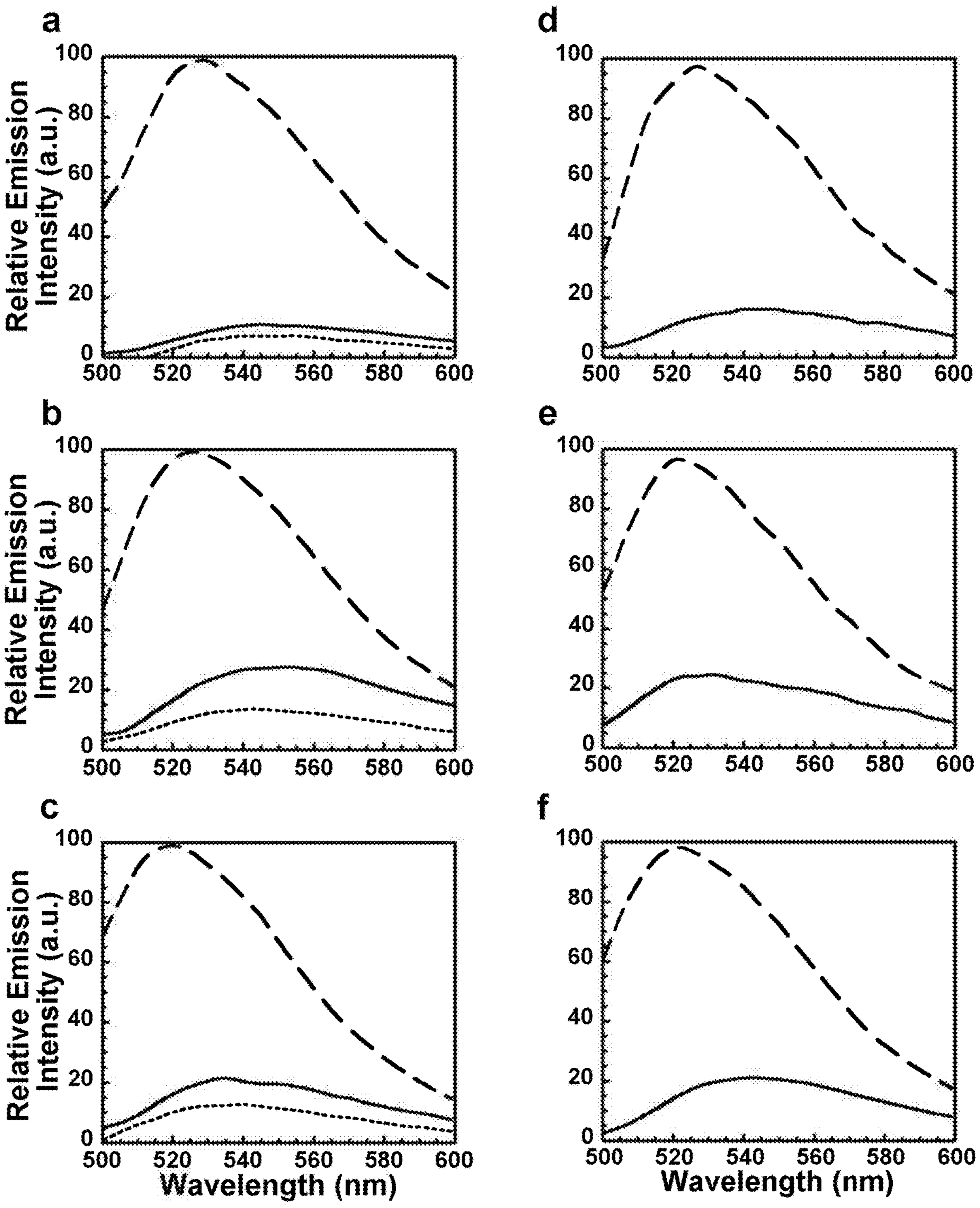
FIG. 4 illustrates that loops L1, L2, and L3 of ILY do not insert into cholesterol-depleted membranes. Each D4 loop residue known to insert into the membrane was substituted for a cysteine and modified with NBD. $ILY^{A428C\text{-}NBD}$ (a), $ILY^{A464C\text{-}NBD}$ (b), or $ILY^{L518C\text{-}NBD}$ (c) was incubated alone (solid line), with hRBCs (dashed line), or with hRBCs depleted of cholesterol (dotted line). Membrane cholesterol was then restored and the insertion of loops L1, L2, and L3 determined. $ILY^{A428C\text{-}NBD}$ (d), $ILY^{A464C\text{-}NBD}$ (e), or $ILY^{L518C\text{-}NBD}$ (f) was incubated alone (solid line) or with cholesterol replete membranes (dashed line).

In stark contrast to the increase in fluorescence emission intensity seen when each loop inserts into the membrane of native hRBC ghosts, depletion of approximately 90% of the membrane of cholesterol abrogates the membrane insertion of all three loops (FIG. 4, panels a-c). Restoration of cholesterol to the cholesterol-depleted membranes restores the ability of the loops to insert into the membrane (FIG. 4, panels d-f)). Hence, membrane cholesterol is required for the insertion of the L1-L3 loops, and, as shown previously, this insertion is necessary for prepore to pore conversion[14, 15].

Aspartate Substitution of Residues in Loops L1-L3 of PFO Prevents its Binding to Cholesterol-Rich Membranes.

The membrane insertion of the L1-L3 loops of ILY was sensitive to cholesterol depletion in native membranes, suggesting that in PFO these same loops might mediate its binding directly to cholesterol-rich membranes. However, this problem could not be approached in PFO in a similar manner to that used with ILY, since cholesterol depletion decreases the binding of PFO to the membrane. Therefore, the effect of mutating these same loops on binding of PFO to cholesterol-rich liposomes was determined. This was accomplished by the introduction of aspartate into loops L1-L3 of PFO, previously shown in ILY to prevent their insertion into the membrane's. The insertion of loops L1-L3 is coupled in ILY, and the introduction of an asparate for any single loop residue, Ala-428 (L2), Ala-464 (L3) or Leu518 (L1), blocked their membrane insertion. Therefore, it was predicted that if aspartate was substituted for any one of the analogous residues in PFO, Ala-401, Ala-437 or Leu-491, it would disrupt binding of PFO to cholesterol-rich liposomes.

Figure 5:
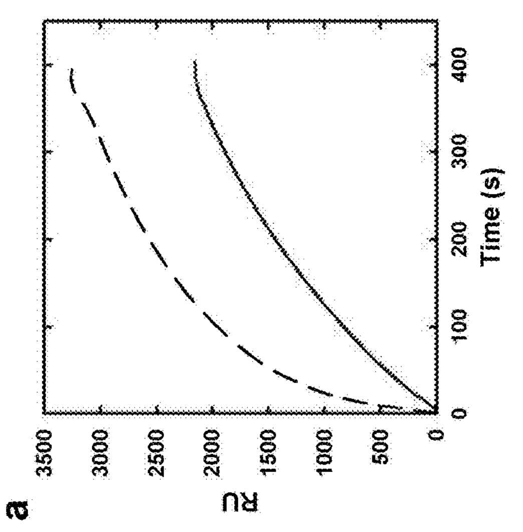
FIG. 5 shows that the L1-L3 loops mediate PFO binding to cholesterol-rich liposomes, (a) SPR analysis of the binding of native (solid line) and NEM modified PFO (dashed line), (b) SPR analysis of the binding of native PFO (solid line), $PFO^{A401D}$ (long dashed line), $PFO^{A437D}$ (short dashed line) and $PFO^{L491D}$ (dotted line).

Individual substitution of the analogous residues in PFO, Ala-401 (L2), Ala-437 (L3) and Leu-491 (L1), resulted in a loss of greater than 99.7% of the hemolytic activity for each mutant (data not shown). Binding of the PFO mutants to cholesterol-PC liposomes was measured by surface plasmon resonance (SPR). As shown in FIG. 5*a*, these mutations significantly reduced binding to cholesterol-PC liposomes when examined by SPR. Substitution of aspartate for Ala-401 (L2) or Leu-491 (L1) completely abrogated binding of PFO to the liposomes membranes, and binding by the aspartate substituted Ala-437 (L3) was less than 7% that of wild type (FIG. 5*b*). This result indicates the D4 L1-L3 loops are critical to the interaction of PFO-like CDCs with cholesterol-rich membranes.

Modification of Cys-459 of PFO Blocks the Membrane Insertion of the Undecapeptide Tryptophan Residues, but not Membrane Binding of PFO.

The conserved undecapeptide of the PFO-like CDCs has been long thought to participate in their binding to cholesterol rich membranes, primarily because chemical modification of the sulfhydryl group of the native cysteine (Cys-459) of the undecapeptide was reported to significantly impact PFO binding to low cell numbers of sheep RBCs, but not to high cell numbers[2]. Others, however, have shown that its modification does not appear to affect binding of other CDCs to cells[5,6]. Therefore, the abilities of native PFO and PFO modified via the sulfhydryl group of Cys-459 of the undecapeptide to bind to cholesterol-PC liposomes via SPR were compared.

Figure 6:
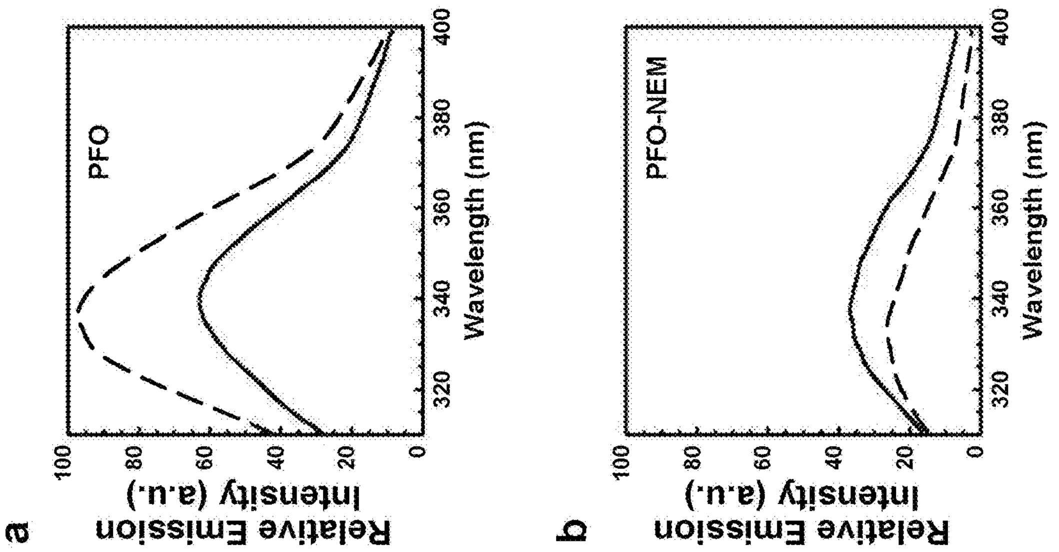
FIG. 6 illustrates that chemical modification of the PFO undecapeptide cysteine sulfhydryl blocks the membrane insertion of the undecapeptide tryptophans and conversion of the prepore to pore. The increase in the intrinsic fluorescence emission of the PFO undecapeptide tryptophans has been used to measure their insertion into the membrane[20, 21]. (a) The increase in the intrinsic fluorescence emission of the tryptophans in native PFO is shown as it moves from its soluble form (solid line) to its membrane-bound state (dashed line). (b) The same experiment shown in (a) was repeated with native PFO that had been modified at Cys-459 with NEM.

Modification of the PFO undecapeptide Cys-459 thiol with the sulfhydryl specific reagent N-ethylmaleimide (NEM) reduced the hemolytic activity by 99% (data not shown), similar to other reports in which the cysteine sulfhydryl of PFO and SLO were chemically modified[2,18]. The rate and extent of binding, however, of the NEM-modified toxin was increased over that of native toxin, as determined by SPR analysis (FIG. 6A-B). Therefore, chemical modification of Cys-459 did not disrupt binding of PFO to the membrane.

If modification of Cys-459 did not affect binding, it raised the question of what this modification does to PFO that effectively blocked its activity. Since the discovery of the CDCs nearly 90 years ago, it has been known that their cytolytic mechanism was sensitive to oxidation. The oxidation sensitive residue was ultimately linked to the highly conserved undecapeptide cysteine residue[1]. The structural effects of the cysteine modification on PFO were further examined to determine if its modification prevented a structural change in PFO that could impact its activity. The membrane insertion of the undecapeptide tryptophans 464, 466 and 467 is conformationally coupled to the insertion of the D3 TMHs. Previous studies have shown that mutations in the D3 TMH1 residues that increase their rate of insertion also increase the rate of membrane insertion of the undecapeptide tryptophan residues[19]. Since Cys-459 is juxtaposed to the tryptophan residues, it was determined if chemical modification of the cysteine thiol group blocked the membrane insertion of the tryptophan residues.

The membrane insertion of the undecapeptide tryptophan residues can be monitored by the increase in their intrinsic fluorescence intensity as they move into the nonpolar environment of the membrane[20,21]. The insertion of these tryptophans was measured in the NEM-modified and native PFO (FIGS. 6*a* and 6*b*). The modification of Cys-459 blocked the insertion of the undecapeptide tryptophans, but did not prevent it from forming an SDS-resistant oligomer, similar to native PFO (data not shown). Hence, these data show that the conformational change in the PFO structure that is reflected by the loss of the insertion of the undecapeptide tryptophan residues affects the subsequent conversion of the prepore oligomer to the pore complex.

Immunization with Pneumolysin Mutant Leu 460Asp

Figure 7:
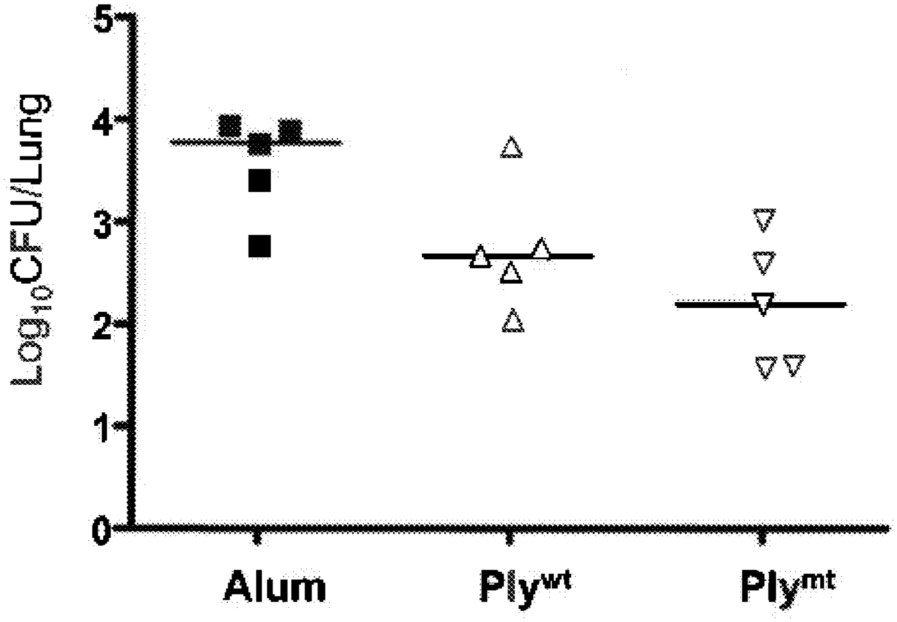
FIG. 7 shows the immunogenic response in mice immunized with a mutant pneumolysin polypeptide and a wild-type pneumolysin then inoculated with *S. pneumoniae.*

CBA/CAHN-XID mice were immunized subcutaneously with 5 μg of pneumolysin or pneumolysin mutant, using alum (aluminum hydroxide) as the adjuvant on days 0 and 14. On day 21, the mice were immunized with the proteins in diluent alone (no adjuvant). All injections were given in 0.2 ml volume. On day 35, mice were challenged with capsular type 19F strain EF3030. Seven days later, the mice were euthanized with carbon dioxide gas. The lungs were homogenized, and the numbers of colony forming units (CFU) in the lungs of each mouse was determined by plating the homogenized tissue on blood agar plates. The mice were also bled. No pneumococci were observed in the blood, demonstrating that this is a model of pneumonia and not pneumonia and sepsis. The results show that both wild-type and the mutant pneumolysin were able to protect against pneumonia in a focal pneumonia model in mice (FIG. 7).

Two long-standing hallmarks of the CDCs are the dependence of their pore-forming mechanism on the presence of membrane cholesterol and the reversible inactivation of most CDCs by oxidation of the undecapeptide cysteine. The studies herein resolve the molecular basis for both phenomena. Without wishing to be bound by theory, the membrane insertion of the L1-L3 loops, located at the base of domain 4, appears to be the primary event that is sensitive to the presence of membrane cholesterol for ILY. Upon cholesterol depletion, these loops do not insert into the membrane, and, as shown previously, cholesterol extraction from hRBC membranes[15] prevents the prepore to pore conversion of ILY. These results indicate that both effects also result from the inability of these loops to insert into cholesterol-depleted membranes. These data further indicate that the oxidation of the conserved cysteine in PFO, and presumably other PFO-like CDCs, blocks the membrane insertion of the tryptophan residues that trap PFO in a prepore state, but does not affect binding to cholesterol-rich liposomes.

The discovery of ILY, a human cell specific toxin, presented a conundrum of how ILY could discriminate between human and animal cells if cholesterol was its receptor. The human cell specificity of ILY was explained by the discovery that human CD59, a late stage, species-specific complement inhibitor, was its receptor[13]. Even though cholesterol was not the ILY receptor, its pore-forming mechanism remained sensitive to membrane cholesterol[14], and showed that cholesterol was required for a much later stage of the pore-forming mechanism in ILY; substantial depletion of membrane cholesterol blocked prepore to pore conversion. Interestingly, this was also observed for SLO and PFO[14], two CDCs that can bind directly to cholesterol-rich membranes. Although depletion of membrane cholesterol from hRBCs blocked prepore to pore conversion of PFO, it also decreased PFO binding. Therefore, cholesterol is necessary for prepore to pore conversion for all three CDCs and in addition it also contributes to membrane binding by the PFO-like CDCs.

Recently Soltani et al.[15] showed that the membrane insertion of the L1-L3 D4 loops of ILY is necessary for prepore to pore conversion. Hence, both cholesterol and membrane insertion of the L1-L3 loops were necessary for prepore to pore conversion of ILY. Without wishing to be bound by theory, the data presented herein indicates that a unifying explanation for these observations is that the membrane insertion of these loops only occurs in cholesterol-rich membranes, and this insertion is necessary for the prepore to pore conversion of both ILY and PFO-like CDCs. In addition, the ability of these loops to insert into cholesterol-rich membranes also mediates the initial binding of PFO, and presumably the PFO-like CDCs, to cholesterol-rich membrane surfaces. Therefore, these data indicate that in both ILY and PFO-like CDCs, the L1-L3 loops must insert into the membrane in order for the successful formation of the pore complex. In the case of ILY, binding is mediated first by huCD59 followed by the insertion of the L1-L3 loops into cholesterol-rich membranes, whereas these two events, binding and insertion, are one and the same in PFO and are mediated primarily by the L1-L3 loops.

It has been traditionally accepted that the undecapeptide of the PFO-like CDCs contributed or directly mediated the recognition of cholesterol-rich membranes[2,3,21]. The studies herein indicate that the L1-L3 loops are the primary structures that mediate the interaction between the CDCs and cholesterol-rich membranes. Although chemical modification of the PFO undecapeptide cysteine with NEM decreases its hemolytic activity by more than 99%, its binding to cholesterol-PC liposomes is largely unimpaired. Hence, in contrast to existing dogma, the interaction of PFO, and other PFO-like CDCs, is primarily mediated by loops L1-L3 and not the undecapeptide. Mutations within the undecapeptide could influence the interaction of L1-L3 with cholesterol rich membranes. It has been shown that mutation of undecapeptide Trp-491 of ILY blocks the insertion of L1-L3[15], and the altered structure of the native ILY undecapeptide apparently prevents the direct interaction of L1-L3 with cholesterol-rich membranes, thus allowing it to first bind to huCD59. This latter idea is reinforced by the fact that when the consensus undecapeptide structure was introduced into ILY, it enabled it to bind to nonhuman cells[22].

It is curious why the L1-L3 loops of ILY do not mediate binding to cholesterol rich membranes similar to PFO. As suggested above, it appears that the major difference in domain 4 between is the primary structure of the highly conserved undecapeptide. It is clear that ILY has lost the ability to bind directly to cholesterol-rich membranes; otherwise, it would not exhibit the human cell specificity mediated via huCD59. The crystal structures of D4 of ILY and PFO may provide an explanation for this difference in the L1-L3 loops to mediate direct binding of these two CDCs to cholesterol-rich membranes. The location and orientation of L1-L3 residues (Leu-518, Ala-428, and Ala-464) of ILY are nearly identical to the analogous residues in PFO (Leu-491, Ala-401, and Ala-437) (FIG. 4*b*). In fact, the majority of the D4 structure of the two CDCs is nearly identical (rms deviation of less than 0.6 Å, reference 23), with the exception of the undecapeptide loop and a β-tongue structure at the top of domain 4. The undecapeptide loop of ILY extends down from the base of D4 4-5Å further than the PFO undecapeptide. Hence, the ILY undecapeptide may sterically hinder the interaction of the L1-L3 loops of ILY with the cholesterol-rich surface. Perhaps only after binding to receptor is the ILY undecapeptide structure altered in such a way as to permit the insertion of the L1-L3 loops.

The present disclosure reveals a structural basis for the severe effect on activity that oxidation of the undecapeptide cysteine exhibits on the cytolytic mechanism of PFO, and presumably other PFO-like CDCs. Originally the CDCs were termed the thiol-activated cytolysins due to this feature, but the molecular basis for this effect was unknown. Early studies suggested that binding to RBCs was affected, but at the same time binding to cholesterol was unaffected, and non-lytic oligomers were still observed on the surface of the cells[2]. As shown herein, this modification prevents the insertion of the undecapeptide tryptophans and results in a prepore-trapped oligomeric structure. Although the precise structural basis for this effect is not known, previous studies have shown that the membrane insertion of the domain 3 TMHs, that form the transmembrane â-barrel pore, is conformationally coupled to the membrane insertion of the domain 4 undecapeptide tryptophan residues[19]. Hence, preventing the membrane insertion of these tryptophans may prevent the insertion of the domain 3 TMHs, thus trapping PFO in the prepore state.

Example 2

His-tagged $PLY_{wildtype}$ and PLY mutants ($PLY_{L460D}$ and $PLY_{L460D/G293S}$) were purified using an affinity column. The average protein yield was $PLY_{wildtype}$: 1 mg/ml, $PLY_{L460D}$: 1 mg/ml, and $PLY_{L460D/G293S}$: 4 mg/ml. The purified proteins were tested for hemolytic activity by incubation of serially titrated toxins with human red blood cells (RBCs). The $EC_{50}$ (effective concentration required to lyse 50%

RBCs) was calculated for each protein from a non-linear sigmoidal dose-response curve. The fold change from wild-type PLY was determined for each mutant (fold change=$EC_{50}$ wildtype/$EC_{50}$ mutant). Results for the two PLY mutants are reported as being more than a certain fold less active than wildtype PLY as the 100% RBCs lysis required for an accurate dose-response curve was unattainable at the highest protein concentrations of these derivatives. The decrease in hemolytic activity of the mutant in comparison to the wild type protein (fold-less active than $PLY_{wildtype}$) for $PLY_{L460D}$ was >10,000 fold and for $PLY_{L460D/G293S}$>260,000 fold.

The relative stability of a protein is inferred from calculating the melting temperature ($T_M$ Celsius), the temperature at which 50% of the protein has unfolded. Protein melt curves were generated using a Protein Thermal Shift Assay Dye Kit (Applied Biosystems). As the temperature is increased the protein unfolds and the dye is able to bind exposed hydrophobic regions and fluoresce. The $T_m$ for $PLY_{wildtype}$, $PLY_{L460D}$, and $PLY_{L460D/G293S}$ were 47.50±0.2, 47.69±0.2, 47.97±0.2, respectively. The insignificant differences in $T_M$ reported for the three PLY proteins indicate that introducing the indicated mutations into $PLY_{wildtype}$ had no effect on the stability of the proteins.

As indicated above, in one non-limiting embodiment, the pneumolysin mutant of the present disclosure is a double mutant designated as PLY-L460D/G293S ($PLY_{L460D/G293S}$) wherein the L of position 460 is substituted with D and the G of position 293 is substituted with S. By itself the G293S substitution only decreases hemolytic activity of the PLY mutant by about 50-fold. The L460D substitution, by itself, decreases activity of the PLY mutant by about 5000-10,000 fold. But in a PLY mutant with both substitutions, the decrease in activity exceeds 260,000-fold less than the native PLY toxin. This is a geometric decrease, not merely an "additive" decrease in activity.

Without wishing to be bound by theory, this precipitous decrease in activity is due to the blockage of two essential functions of PLY. First, the L460D substitution blocks binding to cholesterol and second, the G293S substitution traps PLY in a prepore state that cannot insert the β-barrel pore (the prepore is defined as membrane bound monomers that have oligomerized in the ring like structure, but cannot insert the β-barrel pore). Therefore, the inhibitory effect is geometric: 50×5000–10,000>250,000 fold less toxic (less hemolytic), which is in accordance with measurements that indicate it is >260,000-fold less toxic than native PLY. The G293S substitution also stabilizes the monomer structure of the L460D mutant protein and increases the yield upon purification. For example, upon purification from a 1.0 liter *E. coli* culture, the yield of the PLY-L460D/G293S mutant was approximately 52 mg vs. 3 mg of the PLY-L460D mutant (about 17× greater).

Accordingly, in certain embodiments, the present disclosure is directed to a purified or isolated mutant pneumolysin polypeptide comprising an amino acid sequence that is at least about 90% identical to SEQ ID NO:1 and having an amino acid substitution in at least one of amino acid positions 458, 459, and 460, and in at least one of amino acid positions 293 and 294. The mutant pneumolysin polypeptide may have reduced hemolytic activity and reduced pore forming activity as compared to a wild type pneumolysin polypeptide. The amino acid sequence may be at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO: 1. The mutant pneumolysin polypeptide may include amino acid substitutions in amino acid positions 293 and 458; 293 and 459; 293 and 460; 294 and 458; 294 and 459; or 294 and 460. The mutant pneumolysin polypeptide may include amino acid substitutions in amino acid positions 293, 458, and 459; 293, 459, and 460; or 293, 458, and 460. The mutant pneumolysin polypeptide may include amino acid substitutions in amino acid positions 294, 458, and 459; 294, 459, and 460; or 294, 458, and 460. The mutant pneumolysin polypeptide may include amino acid substitutions in amino acid positions 293, 294, 458, and 459; 293, 294, 459, and 460; or 293, 294, 458, and 460. The mutant pneumolysin polypeptide may include amino acid substitutions in amino acid positions 293, 294, 458, 459, and 460. The mutant pneumolysin polypeptide may comprise a serine or threonine in amino acid position 293, and an aspartic acid, glutamic acid, or asparagine in amino acid position 460. The amino acid sequence of the purified mutant pneumolysin polypeptide may be SEQ ID NO:40. The mutant pneumolysin polypeptide may have an increased yield over a wild type pneumolysin or over a mutant pneumolysin polypeptide having a substitution in only one of amino acid positions 293, 294, 458, 459, and 460. The mutant pneumolysin polypeptide may have about 250,000 fold less hemolytic activity than a wild type pneumolysin polypeptide.

In another embodiment, one or more of the mutant pneumolysin polypeptides described herein above or otherwise contemplated herein may be disposed in a pharmaceutically-acceptable excipient to form an immunogenic composition. Another embodiment includes a vaccine that includes the immunogenic composition, and which may optionally contain an adjuvant. Yet another embodiment is a nucleic acid sequence which encodes any of the mutant pneumolysin polypeptides described or otherwise contemplated herein; a further embodiment is directed to a host cell that includes said nucleic acid sequence. A yet further embodiment is directed to a method of treating, prophylactically preventing, or reducing the occurrence of a condition, disease, or infection caused by *Streptococcus pneumoniae*; in the method, a therapeutically-effective amount of any of the immunogenic compositions described or otherwise contemplated herein is administered to a subject.

In other embodiments, the present disclosure is directed to a purified or isolated mutant streptolysin O polypeptide comprising an amino acid sequence that is at least 90% identical to SEQ ID NO: 9 and having an amino acid substitution in at least one of amino acid positions 561 and 562, and in at least one of amino acid positions 395 and 396. The mutant streptolysin O polypeptide may have reduced hemolytic activity and reduced pore forming activity as compared to a wild type streptolysin O polypeptide. The amino acid sequence may be at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO: 9. The mutant streptolysin O polypeptide may include amino acid substitutions in amino acid positions 395 and 561; 395 and 562; 396 and 561; and/or 396 and 562. The mutant streptolysin O polypeptide may include amino acid substitutions in amino acid positions 395, 561, and 562; 396, 561, and 562; 395, 396, and 561; 395, 396, and 562; and 395, 396, 561 and 562. The mutant streptolysin O polypeptide may have an increased yield over a wild type streptolysin O or over a mutant streptolysin O polypeptide having a substitution in only one of amino acid positions 395, 396, 561, and 562. The mutant streptolysin O polypeptide may have about 250,000 fold less hemolytic activity than a wild type streptolysin O polypeptide.

In another embodiment, one or more of the mutant streptolysin O polypeptides described herein above or otherwise contemplated herein may be disposed in a pharmaceutically-acceptable excipient to form an immunogenic composition. Another embodiment includes a vaccine that includes the immunogenic composition, and which may optionally contain an adjuvant. Yet another embodiment is a nucleic acid sequence which encodes any of the mutant streptolysin O polypeptides described or otherwise contemplated herein; a further embodiment is directed to a host cell that includes said nucleic acid sequence. A yet further embodiment is directed to a method of treating, prophylactically preventing, or reducing the occurrence of a condition, disease, or infection caused by *Streptococcus pyogenes*; in the method, a therapeutically-effective amount of any of the immunogenic compositions described or otherwise contemplated herein is administered to a subject.

Although the present disclosure has been described in detail, it should be understood that various changes, substitutions and alterations can be made in the embodiments described herein without departing from the spirit and scope of the present disclosure. Moreover, the scope of the present disclosure is not intended to be limited to the particular embodiments of the process, compositions of matter, means, methods and steps described in the specification particularly in regard to the specific amino acid or nucleic acid sequences described or enabled herein. As one of ordinary skill in the art will readily appreciate from the present disclosure, processes, compositions of matter, means, methods, sequences, or steps, presently existing or later to be developed that perform substantially the same function or achieve substantially the same result as the corresponding embodiments described herein. Accordingly, the appended claims are intended to include within their scope all such processes, compositions of matter, means, methods, method steps, amino acid sequences, and nucleic acid sequences.

REFERENCES

The following references are specifically incorporated herein by reference, particularly in regard to the exemplary procedural or other details supplementary to those set forth herein.

1. Alouf, J. E., Billington, S. J. & Jost, B. H. Repertoire and general features of the cholesterol-dependent cytolysins in *Bacterial Toxins: A Comprehensive Sourcebook* (eds. Alouf, J. E. & Popoff, M. R.) 643-658 (Academic Press, London, 2005).
2. Iwamoto, M., Ohno-Iwashita, Y. & Ando, S. Role of the essential thiol group in the thiol-activated cytolysin from *Clostridium perfringens. Eur J Biochem* 167, 425-430 (1987).
3. Sekino-Suzuki, N., Nakamura, M., Mitsui, K. I. & Ohno-Iwashita. Y. Contribution of individual tryptophan residues to the structure and activity of theta-toxin (perfringolysin o), a cholesterol-binding cytolysin. *Eur J Biochem* 241, 941-947 (1996).
4. Jacobs, T. et al. The conserved undecapeptide shared by thiol-activated cytolysins is involved in membrane binding. *FEBS Lett.* 459, 463-466 (1999).
5. Vazquez-Boland, J. A., Dominguez, L., Rodriguez-Ferri, E. F., Femandez-Garayzabal, J. F. & Suarez, G. Preliminary evidence that different domains are involved in cytolytic activity and receptor (cholesterol) binding in listeriolysin O, the *Listeria monocytogenes* thiol-activated toxin. *FEMS Microbiol Lett* 53, 95-9 (1989).
6. Saunders, F. K., Mitchell, T. J., Walker, J. A., Andrew, P. W. & Boulnois, G. J. Pneumolysin, the thiol-activated toxin of *Streptococcus pneumoniae*, does not require a thiol group for in vitro activity. *Infect. Immun.* 57, 2547-2552 (1989).
7. Neill, J. M. & Fleming, W. L. Studies on the oxidation and reduction of immunological substances: 11 The hematoxin of the Welch *bacillus. J. Exp. Med.* 44, 215-226 (1926).
8. Alouf, J. E. & Geoffrey, C. Structure activity relationships in the sulfhydryl-activated toxins, in *Bacterial Protein Toxins* (eds. Alouf, J. E., Fehrenbach, F. J., Freer, J. H. & Jeljaszewicz, J.) 165-171 (Academic Press, London, 1984).
9. Nagamune, H. et al. Intermedilysin. A cytolytic toxin specific for human cells of a *Streptococcus intermedius* isolated from human liver abscess. *Adv Exp Med Biol* 418, 773-775 (1997).
10. Nagamune, H. et al. Intermedilysin, a novel cytotoxin specific for human cells secreted by *Streptococcus intermedius* UNS46 isolated from a human liver abscess. *Infect Immun* 64, 3093-3100 (1996).
11. Rollins, S. A., Zhao, J., Ninomiya. H. & Sims, P. J. Inhibition of homologous complement by CD59 is mediated by a species-selective recognition conferred through binding to C8 within C5b-8 or C9 within C5b-9. *J Immunol* 146, 2345-51 (1991).
12. Rollins. S. A. & Sims, P. J. The complement-inhibitory activity of CD59 resides in its capacity to block incorporation of C9 into membrane C5b-9. *J Immunol* 144, 3478-83 (1990).
13. Giddings, K. S., Zhao, J., Sims, P. J. & Tweten, R. K. Human CD59 is a receptor for the cholesterol-dependent cytolysin intermedilysin. *Nat Struct Mol Biol* 12, 1173-1178 (2004).
14. Giddings, K. S., Johnson, A. E. & Tweten, R. K. Redefining cholesterol's role in the mechanism of the cholesterol-dependent cytolysins. *Proc Natl Acad Sci USA* 100, 11315-11320 (2003).
15. Soltani, C. E., Hotze, E. M., Johnson, A. E. & Tweten, R. K Specific protein-membrane contacts are required for prepore and pore assembly by a cholesterol-dependent cytolysin. *J. Biol. Chem.* Paper is press 282 (21), 15709-15716, Apr. 5, 2007.
16. Shepard, L. A. et al. Identification of a membrane-spanning domain of the thiol-activated pore-forming toxin *Clostridium perfringens* perfringolysin O: an á-helical to â-sheet transition identified by fluorescence spectroscopy. *Biochemistry* 37, 14563-14574 (1998).
17. Ramachandran, R., Heuck, A. P., Tweten, R. K. & Johnson, A. E. Structural insights into the membrane-anchoring mechanism of a cholesterol-dependent cytolysin. *Nat Struct Biol* 9, 823-7 (2002).
18. Harris, J. R., Adrian, M., Bhakdi, S. & Palmer, M. Cholesterol-Streptolysin O Interaction: An EM Study of Wild-Type and Mutant Streptolysin O. *J Struct Biol* 121, 343-55 (1998).
19. Heuck, A. P., Hotze, E., Tweten, R. K. & Johnson, A. E. Mechanism of membrane insertion of a multimeric b-barrel protein: Perfringolysin O creates a pore using ordered and coupled conformational changes. *Molec. Cell* 6, 1233-1242 (2000).

20. Heuck, A. P., Tweten, R. K. & Johnson, A. E. Assembly and topography of the prepore complex in cholesterol-dependent cytolysins. *J Biol Chem* 278, 31218-31225 (2003).
21. Nakamura, M., Sekino, N., Iwamoto, M. & Ohno-Iwashita, Y. Interaction of theta-toxin (perfringolysin O), a cholesterol-binding cytolysin, with liposomal membranes: change in the aromatic side chains upon binding and insertion. *Biochemistry* 34, 6513-6520 (1995).
22. Nagamune, H. et al. The human-specific action of intermedilysin, a homolog of streptolysin o, is dictated by domain 4 of the protein. *Microbiol Immunol* 48, 677-92 (2004).
23. Polekhina, G., Giddings, K. S., Tweten, R. K. & Parker, M. W. Insights into the action of the superfamily of cholesterol-dependent cytolysins from studies of intermedilysin. *Proc Natl Acad Sci* 102, 600-605 (2005).
24. Rossjohn, J., Feil, S. C., McKinstry, W. J., Tweten, R. K. & Parker, M. W. Structure of a cholesterol-binding thiol-activated cytolysin and a model of its membrane form. *Cell* 89, 685-692 (1997).
25. Humphrey, W., Dalke, A. & Schulten, K. VMD: visual molecular dynamics. *J Mol Graph* 14, 33-8, 27-8 (1996).
26. Anonymous: Prevention of Pneumococcol Disease: Recommendations of the Advisory Committee on Immunization Practices (ACIP). Morbidity and Mortality Weekly Report-Recommendations and Reports: 46:1-24 (Apr. 4, 1997).

What is claimed is:

1. A purified mutant pneumolysin polypeptide comprising:

an amino acid sequence that is at least 90% identical to SEQ ID NO:1 and having:

an amino acid substitution in at least one of amino acid positions 458, 459, and 460 of SEQ ID NO:1; and an amino acid substitution in at least one of amino acid positions 293 and 294 of SEQ ID NO:1.

2. The purified mutant pneumolysin polypeptide of claim 1, wherein said mutant pneumolysin polypeptide has substitutions G293S and L460D.

3. The purified mutant pneumolysin polypeptide of claim 1, wherein the amino acid sequence is at least 95% identical to SEQ ID NO:1.

4. The purified mutant pneumolysin polypeptide of claim 1, comprising amino acid substitutions in amino acid positions 293 and 458.

5. The purified mutant pneumolysin polypeptide of claim 1, comprising amino acid substitutions in amino acid positions 293 and 459.

6. The purified mutant pneumolysin polypeptide of claim 1, comprising amino acid substitutions in amino acid positions 293 and 460.

7. The purified mutant pneumolysin polypeptide of claim 1, comprising amino acid substitutions in amino acid positions 294 and 458.

8. The purified mutant pneumolysin polypeptide of claim 1, comprising amino acid substitutions in amino acid positions 294 and 459.

9. The purified mutant pneumolysin polypeptide of claim 1, comprising amino acid substitutions in amino acid positions 294 and 460.

10. The purified mutant pneumolysin polypeptide of claim 1, comprising a substitution in amino acid position 460.

11. The purified mutant pneumolysin polypeptide of claim 1, comprising a substitution in amino acid position 293.

12. The purified mutant pneumolysin polypeptide of claim 1, comprising a serine or threonine in amino acid position 293 and an aspartic acid, glutamic acid, or asparagine in amino acid position 460.

13. The purified mutant pneumolysin polypeptide of claim 1, wherein the amino acid sequence thereof comprises SEQ ID NO:40.

14. An immunogenic composition comprising one or more of the mutant pneumolysin polypeptides of any one of claim 1 to 12 or 13 disposed in a pharmaceutically-acceptable excipient.

15. The immunogenic composition of claim 14, wherein the immunogenic composition is a vaccine.

16. The immunogenic composition of claim 14, further comprising an adjuvant.

17. A nucleic acid molecule comprising a nucleotide sequence encoding the mutant pneumolysin polypeptide of any one of claim 1 to 12 or 13.

18. A host cell, comprising the nucleic acid molecule of claim 17.

19. A method of eliciting an immunogenic response, comprising the step of:

administering to the subject the immunogenic composition of claim 14.

* * * * *

UNITED STATES PATENT AND TRADEMARK OFFICE

CERTIFICATE OF CORRECTION

PATENT NO. : 10,562,941 B2
APPLICATION NO. : 15/527919
DATED : February 18, 2020
INVENTOR(S) : Rodney K. Tweten It is certified that error appears in the above-identified patent and that said Letters Patent is hereby corrected as shown below:

On the Title Page

Page 2 Under (56) References Cited, Other Publications:

Second Column, after Line 41: Insert -- EP Application No. 111742359; Rodney K. Tweten, filed July 5, 2011; Examination Report dated April 16, 2013. --

In the Specification

Column 23, Line 51: Delete "lacd," and replace with -- lacl, --

Column 29, Line 50: Delete "37'C." and replace with -- 37°C. --

Column 31, Line 39: Delete "membrane's." and replace with -- membrane15. --

Column 37, Line 65: Delete "Femandez-Garayzabal," and replace with -- Fernandez-Garayzabal, --

Column 38, Line 9: After "substances:" delete "11" and replace with -- II --

Signed and Sealed this
Thirty-first Day of March, 2020

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 471
<212> TYPE: PRT
<213> ORGANISM: Streptococcus pneumoniae

<400> SEQUENCE: 1

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270
```

Ala Pro Gln Thr Glu Trp Lys Gln Ile Leu Asp Asn Thr Glu Val Lys
275 280 285

Ala Val Ile Leu Gly Gly Asp Pro Ser Ser Gly Ala Arg Val Val Thr
290 295 300

Gly Lys Val Asp Met Val Glu Asp Leu Ile Gln Glu Gly Ser Arg Phe
305 310 315 320

Thr Ala Asp His Pro Gly Leu Pro Ile Ser Tyr Thr Thr Ser Phe Leu
325 330 335

Arg Asp Asn Val Val Ala Thr Phe Gln Asn Ser Thr Asp Tyr Val Glu
340 345 350

Thr Lys Val Thr Ala Tyr Arg Asn Gly Asp Leu Leu Leu Asp His Ser
355 360 365

Gly Ala Tyr Val Ala Gln Tyr Tyr Ile Thr Trp Asp Glu Leu Ser Tyr
370 375 380

Asp His Gln Gly Lys Glu Val Leu Thr Pro Lys Ala Trp Asp Arg Asn
385 390 395 400

Gly Gln Asp Leu Thr Ala His Phe Thr Thr Ser Ile Pro Leu Lys Gly
405 410 415

Asn Val Arg Asn Leu Ser Val Lys Ile Arg Glu Cys Thr Gly Leu Ala
420 425 430

Trp Glu Trp Trp Arg Thr Val Tyr Glu Lys Thr Asp Leu Pro Leu Val
435 440 445

Arg Lys Arg Thr Ile Ser Ile Trp Gly Thr Thr Leu Tyr Pro Gln Val
450 455 460

Glu Asp Lys Val Glu Asn Asp
465 470

<210> SEQ ID NO 2
<211> LENGTH: 509
<212> TYPE: PRT
<213> ORGANISM: Bacillus cereus

<400> SEQUENCE: 2

Met Asn Ile Lys Lys Asn Thr Lys Arg Arg Lys Phe Leu Ala Cys Leu
1 5 10 15

Leu Val Ser Leu Cys Thr Ile Asn Tyr Ser Ser Ile Ser Phe Ala Glu
20 25 30

Thr Gln Ala Ser Asn Ala Thr Asp Val Thr Lys Asn Ala Ser Gly Ile
35 40 45

Asp Thr Gly Ile Ala Asn Leu Lys Tyr Asn Asn Gln Glu Val Leu Ala
50 55 60

Val Asn Gly Asp Lys Val Glu Ser Phe Val Pro Lys Glu Ser Ile Asn
65 70 75 80

Ser Asn Gly Lys Phe Val Val Val Glu Arg Glu Lys Lys Ser Leu Thr
85 90 95

Thr Ser Pro Val Asp Ile Ser Ile Ile Asp Ser Val Val Asn Arg Thr
100 105 110

Tyr Pro Gly Ala Val Gln Leu Ala Asn Lys Ala Phe Ala Asp Asn Gln
115 120 125

Pro Ser Leu Leu Val Ala Lys Arg Lys Pro Leu Asn Ile Ser Ile Asp
130 135 140

Leu Pro Gly Met Arg Lys Glu Asn Thr Ile Thr Val Gln Asn Pro Thr
145 150 155 160

Tyr Gly Asn Val Ala Gly Ala Val Asp Asp Leu Val Ser Thr Trp Asn

-continued

```
                165                 170                 175

Glu Lys Tyr Ser Thr Thr His Thr Leu Pro Ala Arg Met Gln Tyr Thr
            180                 185                 190

Glu Ser Met Val Tyr Ser Lys Ser Gln Ile Ala Ser Ala Leu Asn Val
        195                 200                 205

Asn Ala Lys Tyr Leu Asp Asn Ser Leu Asn Ile Asp Phe Asn Ala Val
    210                 215                 220

Ala Asn Gly Glu Lys Lys Val Met Val Ala Ala Tyr Lys Gln Ile Phe
225                 230                 235                 240

Tyr Thr Val Ser Ala Glu Leu Pro Asn Asn Pro Ser Asp Leu Phe Asp
                245                 250                 255

Asn Ser Val Thr Phe Asp Glu Leu Thr Arg Lys Gly Val Ser Asn Ser
            260                 265                 270

Ala Pro Pro Val Met Val Ser Asn Val Ala Tyr Gly Arg Thr Ile Tyr
        275                 280                 285

Val Lys Leu Glu Thr Thr Ser Lys Ser Lys Asp Val Gln Ala Ala Phe
    290                 295                 300

Lys Ala Leu Leu Lys Asn Asn Ser Val Glu Thr Ser Gly Gln Tyr Lys
305                 310                 315                 320

Asp Ile Phe Glu Glu Ser Thr Phe Thr Ala Val Val Leu Gly Gly Asp
                325                 330                 335

Ala Lys Glu His Asn Lys Val Val Thr Lys Asp Phe Asn Glu Ile Arg
            340                 345                 350

Asn Ile Ile Lys Asp Asn Ala Glu Leu Ser Leu Lys Asn Pro Ala Tyr
        355                 360                 365

Pro Ile Ser Tyr Thr Ser Thr Phe Leu Lys Asp Asn Ser Thr Ala Ala
    370                 375                 380

Val His Asn Asn Thr Asp Tyr Ile Glu Thr Thr Thr Thr Glu Tyr Ser
385                 390                 395                 400

Ser Ala Lys Met Thr Leu Asp His Tyr Gly Ala Tyr Val Ala Gln Phe
                405                 410                 415

Asp Val Ser Trp Asp Glu Phe Thr Phe Asp Gln Lys Gly Asn Glu Val
            420                 425                 430

Leu Thr His Lys Thr Trp Asp Gly Ser Gly Lys Asp Lys Thr Ala His
        435                 440                 445

Tyr Ser Thr Val Ile Pro Leu Pro Pro Asn Ser Lys Asn Ile Lys Ile
    450                 455                 460

Val Ala Arg Glu Cys Thr Gly Leu Ala Trp Glu Trp Trp Arg Thr Ile
465                 470                 475                 480

Ile Asn Glu Gln Asn Val Pro Leu Thr Asn Glu Ile Lys Val Ser Ile
                485                 490                 495

Gly Gly Thr Thr Leu Tyr Pro Thr Ala Ser Ile Ser His
            500                 505


<210> SEQ ID NO 3
<211> LENGTH: 512
<212> TYPE: PRT
<213> ORGANISM: Bacillus anthracis

<400> SEQUENCE: 3

Met Ile Phe Leu Asn Ile Lys Lys Asn Thr Lys Arg Arg Lys Phe Leu
1               5                   10                  15

Ala Cys Leu Leu Val Ser Leu Cys Thr Ile His Tyr Ser Ser Ile Ser
            20                  25                  30
```

-continued

```
Phe Ala Glu Thr Gln Ala Gly Asn Ala Thr Gly Ala Ile Lys Asn Ala
        35                  40                  45

Ser Asp Ile Asn Thr Gly Ile Ala Asn Leu Lys Tyr Asp Ser Arg Asp
    50                  55                  60

Ile Leu Ala Val Asn Gly Asp Lys Val Glu Ser Phe Ile Pro Lys Glu
65                  70                  75                  80

Ser Ile Asn Ser Asn Gly Lys Phe Val Val Val Glu Arg Glu Lys Lys
                85                  90                  95

Ser Leu Thr Thr Ser Pro Val Asp Ile Leu Ile Ile Asp Ser Val Val
            100                 105                 110

Asn Arg Thr Tyr Pro Gly Ala Val Gln Leu Ala Asn Lys Ala Phe Ala
        115                 120                 125

Asp Asn Gln Pro Ser Leu Leu Val Ala Lys Arg Lys Pro Leu Asn Ile
    130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
                165                 170                 175

Thr Trp Asn Glu Lys Tyr Ser Thr Thr His Thr Leu Pro Ala Arg Met
            180                 185                 190

Gln Tyr Thr Glu Ser Met Val Tyr Ser Lys Ser Gln Ile Ala Ser Ala
        195                 200                 205

Leu Asn Val Asn Ala Lys Tyr Leu Asp Asn Ser Leu Asn Ile Asp Phe
    210                 215                 220

Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
            260                 265                 270

Ser Asn Ser Ala Pro Pro Val Met Val Ser Asn Val Ala Tyr Gly Arg
        275                 280                 285

Thr Val Tyr Val Lys Leu Glu Thr Thr Ser Lys Ser Lys Asp Val Gln
    290                 295                 300

Ala Ala Phe Lys Ala Leu Leu Lys Asn Asn Ser Val Glu Thr Ser Gly
305                 310                 315                 320

Gln Tyr Lys Asp Ile Phe Glu Glu Ser Thr Phe Thr Ala Val Val Leu
                325                 330                 335

Gly Gly Asp Ala Lys Glu His Asn Lys Val Val Thr Lys Asp Phe Asn
            340                 345                 350

Glu Ile Arg Asn Ile Ile Lys Asp Asn Ala Glu Leu Ser Phe Lys Asn
        355                 360                 365

Pro Ala Tyr Pro Ile Ser Tyr Thr Ser Thr Phe Leu Lys Asp Asn Ala
    370                 375                 380

Thr Ala Ala Val His Asn Asn Thr Asp Tyr Ile Glu Thr Thr Thr Thr
385                 390                 395                 400

Glu Tyr Ser Ser Ala Lys Met Thr Leu Asp His Tyr Gly Ala Tyr Val
                405                 410                 415

Ala Gln Phe Asp Val Ser Trp Asp Glu Phe Thr Phe Asp Gln Asn Gly
            420                 425                 430

Lys Glu Val Leu Thr His Lys Thr Trp Glu Gly Ser Gly Lys Asp Lys
        435                 440                 445

Thr Ala His Tyr Ser Thr Val Ile Pro Leu Pro Pro Asn Ser Lys Asn
```

-continued

```
    450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
                485                 490                 495

Val Ser Ile Gly Gly Thr Thr Leu Tyr Pro Thr Ala Thr Ile Ser His
            500                 505                 510


<210> SEQ ID NO 4
<211> LENGTH: 509
<212> TYPE: PRT
<213> ORGANISM: Bacillus thuringiensis

<400> SEQUENCE: 4

Met Asn Ile Lys Lys Asn Thr Lys Arg Arg Lys Phe Leu Ala Cys Leu
1               5                   10                  15

Leu Val Ser Leu Cys Thr Ile Asn Tyr Ser Ser Ile Ser Phe Ala Glu
            20                  25                  30

Thr Gln Ala Ser Asn Ala Thr Asp Val Thr Lys Asn Ala Ser Gly Ile
        35                  40                  45

Asp Thr Gly Ile Ala Asn Leu Lys Tyr Asn Ile Gln Glu Val Leu Ala
    50                  55                  60

Val Asn Gly Asp Lys Val Glu Ser Phe Val Pro Lys Glu Ser Ile Asn
65                  70                  75                  80

Ser Asn Gly Lys Phe Val Val Val Glu Arg Glu Lys Lys Ser Leu Thr
                85                  90                  95

Thr Ser Pro Val Asp Ile Ser Ile Ile Asp Ser Val Val Asn Arg Thr
            100                 105                 110

Tyr Pro Gly Ala Val Gln Leu Ala Asn Lys Ala Phe Ala Asp Asn Gln
        115                 120                 125

Pro Ser Leu Leu Val Ala Lys Arg Lys Pro Leu Asn Ile Ser Ile Asp
    130                 135                 140

Leu Pro Gly Met Arg Lys Glu Asn Thr Ile Thr Val Gln Asn Pro Thr
145                 150                 155                 160

Tyr Gly Asn Val Ala Gly Ala Val Asp Asp Leu Val Ser Thr Trp Asn
                165                 170                 175

Glu Lys Tyr Ser Thr Thr His Thr Leu Pro Ala Arg Met Gln Tyr Thr
            180                 185                 190

Glu Ser Met Val Tyr Ser Lys Ser Gln Ile Ala Ser Ala Leu Asn Val
        195                 200                 205

Asn Ala Lys Tyr Leu Asp Asn Ser Leu Asn Ile Gly Phe Asn Ala Val
    210                 215                 220

Ala Asn Gly Glu Lys Lys Val Met Val Ala Ala Tyr Lys Gln Ile Phe
225                 230                 235                 240

Tyr Thr Val Ser Ala Glu Leu Pro Asn Asn Pro Ser Asp Leu Phe Asp
                245                 250                 255

Asn Ser Val Thr Phe Asp Glu Leu Thr Arg Lys Gly Val Asn Asn Ser
            260                 265                 270

Ala Pro Pro Val Met Val Ser Asn Val Ala Tyr Gly Arg Thr Ile Tyr
        275                 280                 285

Val Lys Leu Glu Thr Thr Ser Lys Ser Lys Asp Val Gln Ala Ala Phe
    290                 295                 300

Lys Ala Leu Leu Lys Asn Asn Ser Val Glu Thr Ser Gly Gln Tyr Lys
305                 310                 315                 320
```

```
Asp Ile Phe Glu Glu Ser Thr Phe Thr Ala Val Val Leu Gly Gly Asp
                325                 330                 335

Ala Lys Glu His Asn Lys Val Val Thr Lys Asp Phe Asn Glu Ile Arg
            340                 345                 350

Asn Ile Ile Lys Asp Asn Ala Glu Leu Ser Leu Lys Asn Pro Ala Tyr
        355                 360                 365

Pro Ile Ser Tyr Thr Ser Thr Phe Leu Lys Asp Asn Ala Thr Ala Ala
    370                 375                 380

Val His Asn Asn Thr Asp Tyr Ile Glu Thr Thr Thr Thr Glu Tyr Ser
385                 390                 395                 400

Ser Ala Lys Met Thr Leu Asp His Tyr Gly Ala Tyr Val Ala Gln Phe
                405                 410                 415

Asp Val Ser Trp Asp Glu Phe Thr Phe Asp Gln Lys Gly Asn Glu Val
            420                 425                 430

Leu Thr His Lys Thr Trp Asp Gly Ser Gly Lys Asp Lys Thr Ala His
        435                 440                 445

Tyr Ser Thr Val Ile Pro Leu Pro Pro Asn Ser Lys Asn Ile Lys Ile
    450                 455                 460

Val Ala Arg Glu Cys Thr Gly Leu Ala Trp Glu Trp Trp Arg Thr Ile
465                 470                 475                 480

Ile Asn Glu Gln Asn Val Pro Leu Thr Asn Glu Ile Lys Val Ser Ile
                485                 490                 495

Gly Gly Thr Thr Leu Tyr Pro Thr Ala Ser Ile Ser His
            500                 505


<210> SEQ ID NO 5
<211> LENGTH: 500
<212> TYPE: PRT
<213> ORGANISM: Clostridium perfringens

<400> SEQUENCE: 5

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190
```

-continued

```
Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
    210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
    290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
        355                 360                 365

Asp Asn Ser Val Ala Ala Val His Asn Lys Thr Asp Tyr Ile Glu Thr
    370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
        435                 440                 445

Ala Arg Asn Ile Arg Ile Lys Ala Arg Glu Cys Thr Gly Leu Ala Trp
    450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500


<210> SEQ ID NO 6
<211> LENGTH: 501
<212> TYPE: PRT
<213> ORGANISM: Bacillus alvei

<400> SEQUENCE: 6

Met Lys Lys Lys Ser Asn His Leu Lys Gly Arg Lys Val Leu Val Ser
1               5                   10                  15

Leu Leu Val Ser Leu Gln Val Phe Ala Phe Ala Ser Ile Ser Ser Ala
            20                  25                  30

Ala Pro Thr Glu Pro Asn Asp Ile Asp Met Gly Ile Ala Gly Leu Asn
        35                  40                  45

Tyr Asn Arg Asn Glu Val Leu Ala Ile Gln Gly Asp Gln Ile Ser Ser
```

-continued

```
    50                  55                  60

Phe Val Pro Lys Glu Gly Ile Gln Ser Asn Gly Lys Phe Ile Val Val
65                  70                  75                  80

Glu Arg Asp Lys Lys Ser Leu Thr Thr Ser Pro Val Asp Ile Ser Ile
                85                  90                  95

Val Asp Ser Ile Thr Asn Arg Thr Tyr Pro Gly Ala Ile Gln Leu Ala
            100                 105                 110

Asn Lys Asp Phe Ala Asp Asn Gln Pro Ser Leu Val Met Ala Ala Arg
        115                 120                 125

Lys Pro Leu Asp Ile Ser Ile Asp Leu Pro Gly Leu Lys Asn Glu Asn
    130                 135                 140

Thr Ile Ser Val Gln Asn Pro Asn Tyr Gly Thr Val Ser Ser Ala Ile
145                 150                 155                 160

Asp Gln Leu Val Ser Thr Trp Gly Glu Lys Tyr Ser Ser Thr His Thr
                165                 170                 175

Leu Pro Ala Arg Leu Gln Tyr Ala Glu Ser Met Val Tyr Ser Gln Asn
            180                 185                 190

Gln Ile Ser Ser Ala Leu Asn Val Asn Ala Lys Val Leu Asn Gly Thr
        195                 200                 205

Leu Gly Ile Asp Phe Asn Ala Val Ala Asn Gly Glu Lys Lys Val Met
    210                 215                 220

Val Ala Ala Tyr Lys Gln Ile Phe Tyr Thr Val Ser Ala Gly Leu Pro
225                 230                 235                 240

Asn Asn Pro Ser Asp Leu Phe Asp Asp Ser Val Thr Phe Ala Glu Leu
                245                 250                 255

Ala Arg Lys Gly Val Ser Asn Glu Ala Pro Pro Leu Met Val Ser Asn
            260                 265                 270

Val Ala Tyr Gly Arg Thr Ile Tyr Val Lys Leu Glu Thr Thr Ser Lys
        275                 280                 285

Ser Asn Asp Val Gln Thr Ala Phe Lys Leu Leu Leu Asn Asn Pro Ser
    290                 295                 300

Ile Gln Ala Ser Gly Gln Tyr Lys Asp Ile Tyr Glu Asn Ser Ser Phe
305                 310                 315                 320

Thr Ala Val Val Leu Gly Gly Asp Ala Gln Thr His Asn Gln Val Val
                325                 330                 335

Thr Lys Asp Phe Asn Val Ile Gln Ser Val Ile Lys Asp Asn Ala Gln
            340                 345                 350

Phe Ser Ser Lys Asn Pro Ala Tyr Pro Ile Ser Tyr Thr Ser Val Phe
        355                 360                 365

Leu Lys Asp Asn Ser Ile Ala Ala Val His Asn Asn Thr Glu Tyr Ile
    370                 375                 380

Glu Thr Lys Thr Thr Glu Tyr Ser Lys Gly Lys Ile Lys Leu Asp His
385                 390                 395                 400

Ser Gly Ala Tyr Val Ala Gln Phe Glu Val Tyr Trp Asp Glu Phe Ser
                405                 410                 415

Tyr Asp Ala Asp Gly Gln Glu Ile Val Thr Arg Lys Ser Trp Asp Gly
            420                 425                 430

Asn Trp Arg Asp Arg Ser Ala His Phe Ser Thr Glu Ile Pro Leu Pro
        435                 440                 445

Pro Asn Ala Lys Asn Ile Arg Ile Phe Ala Arg Glu Cys Thr Gly Leu
    450                 455                 460

Ala Trp Glu Trp Trp Arg Thr Val Val Asp Glu Tyr Asn Val Pro Leu
465                 470                 475                 480
```

Ala Ser Asp Ile Asn Val Ser Ile Trp Gly Thr Thr Leu Tyr Pro Lys
485 490 495

Ser Ser Ile Thr His
500

<210> SEQ ID NO 7
<211> LENGTH: 574
<212> TYPE: PRT
<213> ORGANISM: Streptococcus canis

<400> SEQUENCE: 7

Met Lys Asp Met Ser Asn Lys Lys Ile Phe Lys Lys Tyr Ser Arg Val
1 5 10 15

Ala Gly Leu Leu Thr Ala Ala Leu Ile Val Gly Asn Leu Val Thr Ala
20 25 30

Asn Ala Asp Ser Asn Lys Gln Asn Thr Ala Asn Thr Glu Thr Thr Thr
35 40 45

Thr Asn Glu Gln Pro Lys Pro Glu Ser Ser Glu Leu Thr Thr Glu Lys
50 55 60

Ala Gly Gln Lys Met Asp Asp Met Leu Asn Ser Asn Asp Met Ile Lys
65 70 75 80

Leu Ala Pro Lys Glu Met Pro Leu Glu Ser Ala Glu Lys Glu Glu Lys
85 90 95

Lys Ser Glu Asp Asn Lys Lys Ser Glu Glu Asp His Thr Glu Glu Ile
100 105 110

Asn Asp Lys Ile Tyr Ser Leu Asn Tyr Asn Glu Leu Glu Val Leu Ala
115 120 125

Lys Asn Gly Glu Thr Ile Glu Asn Phe Val Pro Lys Glu Gly Val Lys
130 135 140

Lys Ala Asp Lys Phe Ile Val Ile Glu Arg Lys Lys Lys Asn Ile Asn
145 150 155 160

Thr Thr Pro Val Asp Ile Ser Ile Ile Asp Ser Val Thr Asp Arg Thr
165 170 175

Tyr Pro Ala Ala Leu Gln Leu Ala Asn Lys Gly Phe Thr Glu Asn Lys
180 185 190

Pro Asp Ala Val Val Thr Lys Arg Asn Pro Gln Lys Ile His Ile Asp
195 200 205

Leu Pro Gly Met Gly Asp Lys Ala Thr Val Glu Val Asn Asp Pro Thr
210 215 220

Tyr Ala Asn Val Ser Thr Ala Ile Asp Asn Leu Val Asn Gln Trp His
225 230 235 240

Asp Asn Tyr Ser Gly Gly Asn Thr Leu Pro Ala Arg Thr Gln Tyr Thr
245 250 255

Glu Ser Met Val Tyr Ser Lys Ser Gln Ile Glu Ala Ala Leu Asn Val
260 265 270

Asn Ser Lys Ile Leu Asp Gly Thr Leu Gly Ile Asp Phe Lys Ser Ile
275 280 285

Ser Lys Gly Glu Lys Lys Val Met Ile Ala Ala Tyr Lys Gln Ile Phe
290 295 300

Tyr Thr Val Ser Ala Asn Leu Pro Asn Asn Pro Ala Asp Val Phe Asp
305 310 315 320

Lys Ser Val Thr Phe Lys Glu Leu Gln Ala Lys Gly Val Ser Asn Glu
325 330 335

Ala Pro Pro Leu Phe Val Ser Asn Val Ala Tyr Gly Arg Thr Val Phe

```
            340                 345                 350

Val Lys Leu Glu Thr Ser Ser Lys Ser Asn Asp Val Glu Ala Ala Phe
        355                 360                 365

Ser Ala Ala Leu Lys Gly Thr Asp Val Lys Thr Asn Gly Lys Tyr Ser
    370                 375                 380

Asp Ile Leu Glu Asn Ser Ser Phe Thr Ala Val Val Leu Gly Ala Asp
385                 390                 395                 400

Ala Ala Glu His Asn Lys Val Val Thr Lys Asp Phe Asp Val Ile Arg
                405                 410                 415

Asn Val Ile Lys Ala Asn Ala Thr Phe Ser Arg Lys Asn Pro Ala Tyr
            420                 425                 430

Pro Ile Ser Tyr Thr Ser Val Phe Leu Lys Asn Asn Lys Ile Ala Gly
        435                 440                 445

Val Asn Asn Arg Ser Glu Tyr Val Glu Thr Thr Ser Thr Glu Tyr Thr
    450                 455                 460

Ser Gly Lys Ile Asn Leu Ser His Gln Gly Ala Tyr Val Ala Gln Tyr
465                 470                 475                 480

Glu Ile Leu Trp Asp Glu Ile Asn Tyr Asp Asp Lys Gly Lys Glu Val
                485                 490                 495

Ile Thr Lys Arg Arg Trp Asp Asn Asn Trp Tyr Ser Lys Thr Ser Pro
            500                 505                 510

Phe Ser Thr Val Ile Pro Leu Gly Ala Asn Ser Arg Asn Ile Arg Ile
        515                 520                 525

Met Ala Arg Glu Cys Thr Gly Leu Ala Trp Glu Trp Trp Arg Lys Val
    530                 535                 540

Ile Asp Glu Arg Asp Val Lys Leu Ser Lys Glu Ile Asn Val Asn Ile
545                 550                 555                 560

Ser Gly Ser Thr Leu Ser Pro Tyr Gly Ser Ile Thr Tyr Lys
                565                 570


<210> SEQ ID NO 8
<211> LENGTH: 571
<212> TYPE: PRT
<213> ORGANISM: Streptococcus equisimilis

<400> SEQUENCE: 8

Met Ser Asn Lys Lys Ile Phe Lys Lys Tyr Ser Arg Val Ala Gly Leu
1               5                   10                  15

Leu Thr Ala Ala Leu Ile Val Gly Asn Leu Val Thr Ala Asn Ala Asp
            20                  25                  30

Ser Asn Lys Gln Asn Thr Ala Asn Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Glu Lys Lys Ser Glu
                85                  90                  95

Asp Asn Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140
```

-continued

```
Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Ser Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
```

565 570

<210> SEQ ID NO 9
<211> LENGTH: 571
<212> TYPE: PRT
<213> ORGANISM: Streptococcus pyogenes

<400> SEQUENCE: 9

Met Ser Asn Lys Lys Thr Phe Lys Lys Tyr Ser Arg Val Ala Gly Leu
1 5 10 15

Leu Thr Ala Ala Leu Ile Ile Gly Asn Leu Val Thr Ala Asn Ala Glu
20 25 30

Ser Asn Lys Gln Asn Thr Ala Ser Thr Glu Thr Thr Thr Thr Ser Glu
35 40 45

Gln Pro Lys Pro Glu Ser Ser Glu Leu Thr Ile Glu Lys Ala Gly Gln
50 55 60

Lys Met Asp Asp Met Leu Asn Ser Asn Asp Met Ile Lys Leu Ala Pro
65 70 75 80

Lys Glu Met Pro Leu Glu Ser Ala Glu Lys Glu Glu Lys Lys Ser Glu
85 90 95

Asp Lys Lys Lys Ser Glu Glu Asp His Thr Glu Glu Ile Asn Asp Lys
100 105 110

Ile Tyr Ser Leu Asn Tyr Asn Glu Leu Glu Val Leu Ala Lys Asn Gly
115 120 125

Glu Thr Ile Glu Asn Phe Val Pro Lys Glu Gly Val Lys Lys Ala Asp
130 135 140

Lys Phe Ile Val Ile Glu Arg Lys Lys Lys Asn Ile Asn Thr Thr Pro
145 150 155 160

Val Asp Ile Ser Ile Ile Asp Ser Val Thr Asp Arg Thr Tyr Pro Ala
165 170 175

Ala Leu Gln Leu Ala Asn Lys Gly Phe Thr Glu Asn Lys Pro Asp Ala
180 185 190

Val Val Thr Lys Arg Asn Pro Gln Lys Ile His Ile Asp Leu Pro Gly
195 200 205

Met Gly Asp Lys Ala Thr Val Glu Val Asn Asp Pro Thr Tyr Ala Asn
210 215 220

Val Ser Thr Ala Ile Asp Asn Leu Val Asn Gln Trp His Asp Asn Tyr
225 230 235 240

Ser Gly Gly Asn Thr Leu Pro Ala Arg Thr Gln Tyr Thr Glu Ser Met
245 250 255

Val Tyr Ser Lys Ser Gln Ile Glu Ala Ala Leu Asn Val Asn Ser Lys
260 265 270

Ile Leu Asp Gly Thr Leu Gly Ile Asp Phe Lys Ser Ile Ser Lys Gly
275 280 285

Glu Lys Lys Val Met Ile Ala Ala Tyr Lys Gln Ile Phe Tyr Thr Val
290 295 300

Ser Ala Asn Leu Pro Asn Asn Pro Ala Asp Val Phe Asp Lys Ser Val
305 310 315 320

Thr Phe Lys Asp Leu Gln Arg Lys Gly Val Ser Asn Glu Ala Pro Pro
325 330 335

Leu Phe Val Ser Asn Val Ala Tyr Gly Arg Thr Val Phe Val Lys Leu
340 345 350

Glu Thr Ser Ser Lys Ser Asn Asp Val Glu Ala Ala Phe Ser Ala Ala
355 360 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 10
<211> LENGTH: 514
<212> TYPE: PRT
<213> ORGANISM: Clostridium novyi

<400> SEQUENCE: 10

Met Lys Lys Ser Leu Lys Thr Ile Ile Arg Ser Ile Ser Phe Leu Ser
1               5                   10                  15

Ile Leu Thr Leu Thr Cys Ser Cys Asn Phe Ile Thr Ser Thr Gln Lys
            20                  25                  30

Asn Val Ser Leu Leu Ser Gly Pro Asn Lys Val Ile Lys Pro Lys Lys
        35                  40                  45

Thr Lys Ser Leu Asp Asp Arg Ile Tyr Gly Leu Lys Tyr Asp Pro Asn
    50                  55                  60

Lys Ile Leu Ser Phe Asn Gly Glu Lys Val Glu Asn Phe Val Pro Asn
65                  70                  75                  80

Glu Gly Phe Ser Thr Pro Asp Lys Tyr Ile Val Ile Lys Arg Glu Lys
                85                  90                  95

Lys Ser Ile Ser Asp Ser Thr Ala Asp Ile Ala Val Ile Asp Ser Met
            100                 105                 110

Asn Asp Lys Thr Tyr Pro Gly Ala Ile Gln Leu Ala Asn Arg Asn Leu
        115                 120                 125

Ile Glu Asn Lys Pro Asn Ile Val Ser Cys Glu Arg Lys Pro Ile Thr
    130                 135                 140

Ile Ser Ile Asp Leu Pro Gly Met Gly Glu Glu Gly Lys Thr Thr Ile
145                 150                 155                 160

Thr Ser Pro Thr Tyr Ser Ser Val Lys Ala Gly Ile Asp Ser Leu Leu
                165                 170                 175

```
Asn Lys Trp Asn Ser His Tyr Ser Ser Ile Tyr Ser Ile Pro Thr Arg
            180                 185                 190

Phe Ser Tyr Ser Asp Ser Met Val Tyr Ser Lys Ser Gln Leu Ser Ala
        195                 200                 205

Lys Leu Gly Cys Asn Phe Lys Ala Leu Asn Lys Ala Leu Asp Ile Asp
    210                 215                 220

Phe Asp Ser Ile Tyr Lys Gly Gln Lys Lys Val Met Leu Leu Ala Tyr
225                 230                 235                 240

Lys Gln Ile Phe Tyr Thr Val Asn Val Asp Ala Pro Asn His Pro Ser
                245                 250                 255

Asp Phe Phe Gly Asp Lys Val Thr Phe Asn Asp Leu Ala Lys Lys Gly
            260                 265                 270

Val Asn Ser Lys Asn Pro Pro Val Tyr Val Ser Ser Val Ser Tyr Gly
        275                 280                 285

Arg Thr Ile Tyr Val Lys Leu Glu Thr Thr Ser Lys Ser Ala Asn Val
    290                 295                 300

Lys Ala Ala Phe Lys Ala Leu Ile Glu Asn Gln Asn Ile Ser Ser Asn
305                 310                 315                 320

Ser Glu Tyr Lys Asn Ile Leu Asn Gln Ser Ser Phe Thr Ala Thr Val
                325                 330                 335

Leu Gly Gly Gly Ala Lys Glu His Asn Lys Val Ile Thr Lys Asn Phe
            340                 345                 350

Asp Glu Ile Arg Asn Ile Ile Thr Asn Asn Ser Glu Tyr Ser Pro Arg
        355                 360                 365

Asn Pro Gly Tyr Pro Ile Ala Tyr Thr Thr Ser Phe Leu Lys Asp Asn
    370                 375                 380

Ser Val Ala Thr Val Asn Asn Lys Thr Asp Tyr Ile Glu Thr Thr Ser
385                 390                 395                 400

Thr Glu Tyr Thr Asn Gly Lys Ile Thr Leu Asp His Arg Gly Ala Tyr
                405                 410                 415

Val Ala Lys Phe Asn Ile Thr Trp Asp Glu Val Ser Tyr Asp Lys Asn
            420                 425                 430

Gly Lys Glu Ile Val Glu His Lys Ser Trp Glu Gly Asn Asp Phe Gly
        435                 440                 445

Arg Thr Ala His Phe Asn Thr Glu Leu Tyr Leu Lys Gly Asn Ala Arg
    450                 455                 460

Asn Ile Cys Ile Lys Ala Lys Glu Cys Thr Gly Leu Ala Trp Glu Trp
465                 470                 475                 480

Trp Arg Thr Ile Ile Asp Asp Lys Asn Val Pro Leu Val Lys Asn Arg
                485                 490                 495

Lys Val Tyr Ile Trp Gly Thr Thr Leu Tyr Pro Arg Thr Leu Thr Glu
            500                 505                 510

Ile Glu


<210> SEQ ID NO 11
<211> LENGTH: 527
<212> TYPE: PRT
<213> ORGANISM: Clostridium tetani

<400> SEQUENCE: 11

Met Asn Lys Asn Val Leu Lys Phe Val Ser Arg Ser Leu Leu Ile Phe
1               5                   10                  15

Ser Met Thr Gly Leu Ile Ser Asn Tyr Asn Ser Ser Asn Val Leu Ala
            20                  25                  30
```

-continued

```
Lys Gly Asn Val Glu Glu His Ser Leu Ile Asn Asn Gly Gln Val Val
        35                  40                  45

Thr Ser Asn Thr Lys Cys Asn Leu Ala Lys Asp Asn Ser Ser Asp Ile
    50                  55                  60

Asp Lys Asn Ile Tyr Gly Leu Ser Tyr Asp Pro Arg Lys Ile Leu Ser
65                  70                  75                  80

Tyr Asn Gly Glu Gln Val Glu Asn Phe Val Pro Ala Glu Gly Phe Glu
                85                  90                  95

Asn Pro Asp Lys Phe Ile Val Val Lys Arg Glu Lys Lys Ser Ile Ser
            100                 105                 110

Asp Ser Thr Ala Asp Ile Ser Ile Ile Asp Ser Ile Asn Asp Arg Thr
        115                 120                 125

Tyr Pro Gly Ala Ile Gln Leu Ala Asn Arg Asn Leu Met Glu Asn Lys
    130                 135                 140

Pro Asp Ile Ile Ser Cys Glu Arg Lys Pro Ile Thr Ile Ser Val Asp
145                 150                 155                 160

Leu Pro Gly Met Ala Glu Asp Gly Lys Lys Val Val Asn Ser Pro Thr
                165                 170                 175

Tyr Ser Ser Val Asn Ser Ala Ile Asn Ser Ile Leu Asp Thr Trp Asn
            180                 185                 190

Ser Lys Tyr Ser Ser Lys Tyr Thr Ile Pro Thr Arg Met Ser Tyr Ser
        195                 200                 205

Asp Thr Met Val Tyr Ser Gln Ser Gln Leu Ser Ala Ala Val Gly Cys
    210                 215                 220

Asn Phe Lys Ala Leu Asn Lys Ala Leu Asn Ile Asp Phe Asp Ser Ile
225                 230                 235                 240

Phe Lys Gly Glu Lys Lys Val Met Leu Leu Ala Tyr Lys Gln Ile Phe
                245                 250                 255

Tyr Thr Val Ser Val Asp Pro Pro Asn Arg Pro Ser Asp Leu Phe Gly
            260                 265                 270

Asp Ser Val Thr Phe Asp Glu Leu Ala Leu Lys Gly Ile Asn Asn Asn
        275                 280                 285

Asn Pro Pro Ala Tyr Val Ser Asn Val Ala Tyr Gly Arg Thr Ile Tyr
    290                 295                 300

Val Lys Leu Glu Thr Thr Ser Lys Ser Ser His Val Lys Ala Ala Phe
305                 310                 315                 320

Lys Ala Leu Ile Asn Asn Gln Asp Ile Ser Ser Asn Ala Glu Tyr Lys
                325                 330                 335

Asp Ile Leu Asn Gln Ser Ser Phe Thr Ala Thr Val Leu Gly Gly Gly
            340                 345                 350

Ala Gln Glu His Asn Lys Ile Ile Thr Lys Asp Phe Asp Glu Ile Arg
        355                 360                 365

Asn Ile Ile Lys Asn Asn Ser Val Tyr Ser Pro Gln Asn Pro Gly Tyr
    370                 375                 380

Pro Ile Ser Tyr Thr Thr Thr Phe Leu Lys Asp Asn Ser Ile Ala Ser
385                 390                 395                 400

Val Asn Asn Lys Thr Glu Tyr Ile Glu Thr Thr Ala Thr Glu Tyr Thr
                405                 410                 415

Asn Gly Lys Ile Val Leu Asp His Ser Gly Ala Tyr Val Ala Gln Phe
            420                 425                 430

Gln Val Thr Trp Asp Glu Val Ser Tyr Asp Glu Lys Gly Asn Glu Ile
        435                 440                 445
```

```
Val Glu His Lys Ala Trp Glu Gly Asn Asn Arg Asp Arg Thr Ala His
    450                 455                 460

Phe Asn Thr Glu Ile Tyr Leu Lys Gly Asn Ala Arg Asn Ile Ser Val
465                 470                 475                 480

Lys Ile Arg Glu Cys Thr Gly Leu Ala Trp Glu Trp Trp Arg Thr Ile
                485                 490                 495

Val Asp Val Lys Asn Ile Pro Leu Ala Lys Glu Arg Thr Phe Tyr Ile
            500                 505                 510

Trp Gly Thr Thr Leu Tyr Pro Lys Thr Ser Ile Glu Thr Lys Met
        515                 520                 525


<210> SEQ ID NO 12
<211> LENGTH: 528
<212> TYPE: PRT
<213> ORGANISM: Listeria ivanovii

<400> SEQUENCE: 12

Met Lys Lys Ile Met Leu Leu Leu Met Thr Leu Leu Leu Val Ser Leu
1               5                   10                  15

Pro Leu Ala Gln Glu Ala Gln Ala Asp Ala Ser Val Tyr Ser Tyr Gln
            20                  25                  30

Gly Ile Ile Ser His Met Ala Pro Pro Ala Ser Pro Pro Ala Lys Pro
        35                  40                  45

Lys Thr Pro Val Glu Lys Lys Asn Ala Ala Gln Ile Asp Gln Tyr Ile
    50                  55                  60

Gln Gly Leu Asp Tyr Asp Lys Asn Asn Ile Leu Val Tyr Asp Gly Glu
65                  70                  75                  80

Ala Val Lys Asn Val Pro Pro Lys Ala Gly Tyr Lys Glu Gly Asn Gln
                85                  90                  95

Tyr Ile Val Val Glu Lys Lys Lys Lys Ser Ile Asn Gln Asn Asn Ala
            100                 105                 110

Asp Ile Gln Val Ile Asn Ser Leu Ala Ser Leu Thr Tyr Pro Gly Ala
        115                 120                 125

Leu Val Lys Ala Asn Ser Glu Leu Val Glu Asn Gln Pro Asp Val Leu
    130                 135                 140

Pro Val Lys Arg Asp Ser Val Thr Leu Ser Ile Asp Leu Pro Gly Met
145                 150                 155                 160

Val Asn His Asp Asn Glu Ile Val Val Gln Asn Ala Thr Lys Ser Asn
                165                 170                 175

Ile Asn Asp Gly Val Asn Thr Leu Val Asp Arg Trp Asn Asn Lys Tyr
            180                 185                 190

Ser Glu Glu Tyr Pro Asn Ile Ser Ala Lys Ile Asp Tyr Asp Gln Glu
        195                 200                 205

Met Ala Tyr Ser Glu Ser Gln Leu Val Ala Lys Phe Gly Ala Ala Phe
    210                 215                 220

Lys Ala Val Asn Asn Ser Leu Asn Val Asn Phe Gly Ala Ile Ser Glu
225                 230                 235                 240

Gly Lys Val Gln Glu Glu Val Ile Asn Phe Lys Gln Ile Tyr Tyr Thr
                245                 250                 255

Val Asn Val Asn Glu Pro Thr Ser Pro Ser Arg Phe Phe Gly Lys Ser
            260                 265                 270

Val Thr Lys Glu Asn Leu Gln Ala Leu Gly Val Asn Ala Glu Asn Pro
        275                 280                 285

Pro Ala Tyr Ile Ser Ser Val Ala Tyr Gly Arg Asp Ile Phe Val Lys
    290                 295                 300
```

```
Leu Ser Thr Ser Ser His Ser Thr Arg Val Lys Ala Ala Phe Asp Thr
305                 310                 315                 320

Ala Phe Lys Gly Lys Ser Val Lys Gly Asp Thr Glu Leu Glu Asn Ile
                325                 330                 335

Ile Gln Asn Ala Ser Phe Lys Ala Val Ile Tyr Gly Gly Ser Ala Lys
            340                 345                 350

Asp Glu Val Glu Ile Ile Asp Gly Asp Leu Ser Lys Leu Arg Asp Ile
        355                 360                 365

Leu Lys Gln Gly Ala Asn Phe Asp Lys Lys Asn Pro Gly Val Pro Ile
    370                 375                 380

Ala Tyr Thr Thr Asn Phe Leu Lys Asp Asn Gln Leu Ala Val Val Lys
385                 390                 395                 400

Asn Asn Ser Glu Tyr Ile Glu Thr Thr Ser Lys Ala Tyr Ser Asp Gly
                405                 410                 415

Lys Ile Asn Leu Asp His Ser Gly Ala Tyr Val Ala Arg Phe Asn Val
            420                 425                 430

Thr Trp Asp Glu Val Ser Tyr Asp Ala Asn Gly Asn Glu Val Val Glu
        435                 440                 445

His Lys Lys Trp Ser Glu Asn Asp Lys Asp Lys Leu Ala His Phe Thr
    450                 455                 460

Thr Ser Ile Tyr Leu Pro Gly Asn Ala Arg Asn Ile Asn Ile His Ala
465                 470                 475                 480

Lys Glu Cys Thr Gly Leu Ala Trp Glu Trp Trp Arg Thr Val Val Asp
                485                 490                 495

Asp Arg Asn Leu Pro Leu Val Lys Asn Arg Asn Val Cys Ile Trp Gly
            500                 505                 510

Thr Thr Leu Tyr Pro Ala Tyr Ser Asp Thr Val Asp Asn Pro Ile Lys
        515                 520                 525


<210> SEQ ID NO 13
<211> LENGTH: 529
<212> TYPE: PRT
<213> ORGANISM: Listeria monocytogenes

<400> SEQUENCE: 13

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Leu Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
```

-continued 145 150 155 160

Met Thr Asn Gln Asp Asn Lys Ile Val Val Lys Asn Ala Thr Lys Ser
165 170 175

Asn Val Asn Asn Ala Val Asn Thr Leu Val Glu Arg Trp Asn Glu Lys
180 185 190

Tyr Ala Gln Ala Tyr Pro Asn Val Ser Ala Lys Ile Asp Tyr Asp Asp
195 200 205

Glu Met Ala Tyr Ser Glu Ser Gln Leu Ile Ala Lys Phe Gly Thr Ala
210 215 220

Phe Lys Ala Val Asn Asn Ser Leu Asn Val Asn Phe Gly Ala Ile Ser
225 230 235 240

Glu Gly Lys Met Gln Glu Glu Val Ile Ser Phe Lys Gln Ile Tyr Tyr
245 250 255

Asn Val Asn Val Asn Glu Pro Thr Arg Pro Ser Arg Phe Phe Gly Lys
260 265 270

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

Lys Asp Glu Val Gln Ile Ile Asp Gly Asn Leu Gly Asp Leu Arg Asp
355 360 365

Ile Leu Lys Lys Gly Ala Thr Phe Asn Arg Glu Thr Pro Gly Val Pro
370 375 380

Ile Ala Tyr Thr Thr Asn Phe Leu Lys Asp Asn Glu Leu Ala Val Ile
385 390 395 400

Lys Asn Asn Ser Glu Tyr Ile Glu Thr Thr Ser Lys Ala Tyr Thr Asp
405 410 415

Gly Lys Ile Asn Ile Asp His Ser Gly Gly Tyr Val Ala Gln Phe Asn
420 425 430

Ile Ser Trp Asp Glu Ile Asn Tyr Asp Pro Glu Gly Asn Glu Ile Val
435 440 445

Gln His Lys Asn Trp Ser Glu Asn Asn Lys Ser Lys Leu Ala His Phe
450 455 460

Thr Ser Ser Ile Tyr Leu Pro Gly Asn Ala Arg Asn Ile Asn Val Tyr
465 470 475 480

Ala Lys Glu Cys Thr Gly Leu Ala Trp Glu Trp Trp Arg Thr Val Ile
485 490 495

Asp Asp Arg Asn Leu Pro Leu Val Lys Asn Arg Asn Ile Ser Ile Trp
500 505 510

Gly Thr Thr Leu Tyr Pro Lys Tyr Ser Asn Ser Val Asp Asn Pro Ile
515 520 525

Glu

<210> SEQ ID NO 14
<211> LENGTH: 530
<212> TYPE: PRT
<213> ORGANISM: Listeria seeligeri

<400> SEQUENCE: 14

Met Lys Ile Phe Gly Leu Val Ile Met Ser Leu Leu Phe Val Ser Leu
1               5                   10                  15

Pro Ile Thr Gln Gln Pro Glu Ala Arg Asp Val Pro Ala Tyr Asp Arg
            20                  25                  30

Ser Glu Val Thr Ile Ser Pro Ala Glu Thr Pro Glu Ser Pro Pro Ala
        35                  40                  45

Thr Pro Lys Thr Pro Val Glu Lys Lys His Ala Glu Glu Ile Asn Lys
    50                  55                  60

Tyr Ile Trp Gly Leu Asn Tyr Asp Lys Asn Ser Ile Leu Val Tyr Gln
65                  70                  75                  80

Gly Glu Ala Val Thr Asn Val Pro Pro Lys Lys Gly Tyr Lys Asp Gly
                85                  90                  95

Ser Glu Tyr Ile Val Val Glu Lys Lys Lys Lys Gly Ile Asn Gln Asn
            100                 105                 110

Asn Ala Asp Ile Ser Val Ile Asn Ala Ile Ser Ser Leu Thr Tyr Pro
        115                 120                 125

Gly Ala Leu Val Lys Ala Asn Arg Glu Leu Val Glu Asn Gln Pro Asn
    130                 135                 140

Val Leu Pro Val Lys Arg Asp Ser Leu Thr Leu Ser Val Asp Leu Pro
145                 150                 155                 160

Gly Met Thr Lys Lys Asp Asn Lys Ile Phe Val Lys Asn Pro Thr Lys
                165                 170                 175

Ser Asn Val Asn Asn Ala Val Asn Thr Leu Val Glu Arg Trp Asn Asp
            180                 185                 190

Lys Tyr Ser Lys Ala Tyr Pro Asn Ile Asn Ala Lys Ile Asp Tyr Ser
        195                 200                 205

Asp Glu Met Ala Tyr Ser Glu Ser Gln Leu Ile Ala Lys Phe Gly Thr
    210                 215                 220

Ala Phe Lys Ala Val Asn Asn Ser Leu Asn Val Asn Phe Glu Ala Ile
225                 230                 235                 240

Ser Asp Gly Lys Val Gln Glu Glu Val Ile Ser Phe Lys Gln Ile Tyr
                245                 250                 255

Tyr Asn Ile Asn Val Asn Glu Pro Thr Ser Pro Ser Lys Phe Phe Gly
            260                 265                 270

Gly Ser Val Thr Lys Glu Gln Leu Asp Ala Leu Gly Val Asn Ala Glu
        275                 280                 285

Asn Pro Pro Ala Tyr Ile Ser Ser Val Ala Tyr Gly Arg Gln Val Tyr
    290                 295                 300

Val Lys Leu Ser Ser Ser Ser His Ser Asn Lys Val Lys Thr Ala Phe
305                 310                 315                 320

Glu Ala Ala Met Ser Gly Lys Ser Val Lys Gly Asp Val Glu Leu Thr
                325                 330                 335

Asn Ile Ile Lys Asn Ser Ser Phe Lys Ala Val Ile Tyr Gly Gly Ser
            340                 345                 350

Ala Lys Glu Glu Val Glu Ile Ile Asp Gly Asn Leu Gly Glu Leu Arg
        355                 360                 365

Asp Ile Leu Lys Lys Gly Ser Thr Tyr Asp Arg Glu Asn Pro Gly Val
    370                 375                 380

Pro Ile Ser Tyr Thr Thr Asn Phe Leu Lys Asp Asn Asp Leu Ala Val
385                 390                 395                 400

Val Lys Asn Asn Ser Glu Tyr Ile Glu Thr Thr Ser Lys Ser Tyr Thr
                405                 410                 415

Asp Gly Lys Ile Asn Ile Asp His Ser Gly Gly Tyr Val Ala Gln Phe
420 425 430

Asn Ile Ser Trp Asp Glu Val Ser Tyr Asp Glu Asn Gly Asn Glu Ile
435 440 445

Lys Val His Lys Lys Trp Gly Glu Asn Tyr Lys Ser Lys Leu Ala His
450 455 460

Phe Thr Ser Ser Ile Tyr Leu Pro Gly Asn Ala Arg Asn Ile Asn Ile
465 470 475 480

Tyr Ala Arg Glu Cys Thr Gly Leu Phe Trp Glu Trp Trp Arg Thr Val
485 490 495

Ile Asp Asp Arg Asn Leu Pro Leu Val Lys Asn Arg Asn Val Ser Ile
500 505 510

Trp Gly Thr Thr Leu Tyr Pro Arg His Ser Asn Asn Val Asp Asn Pro
515 520 525

Ile Gln
530

<210> SEQ ID NO 15
<211> LENGTH: 497
<212> TYPE: PRT
<213> ORGANISM: Streptococcus suis

<400> SEQUENCE: 15

Met Arg Lys Ser Ser His Leu Ile Leu Ser Ser Ile Val Ser Leu Ala
1 5 10 15

Leu Val Gly Val Thr Pro Leu Ser Val Leu Ala Asp Ser Lys Gln Asp
20 25 30

Ile Asn Gln Tyr Phe Gln Ser Leu Thr Tyr Glu Pro Gln Glu Ile Leu
35 40 45

Thr Asn Glu Gly Glu Tyr Ile Asp Asn Pro Pro Ala Thr Thr Gly Met
50 55 60

Leu Glu Asn Gly Arg Phe Val Val Leu Arg Arg Glu Lys Lys Asn Ile
65 70 75 80

Thr Asn Asn Ser Ala Asp Ile Ala Val Ile Asp Ala Lys Ala Ala Asn
85 90 95

Ile Tyr Pro Gly Ala Leu Leu Arg Ala Asp Gln Asn Leu Leu Asp Asn
100 105 110

Asn Pro Thr Leu Ile Ser Ile Ala Arg Gly Asp Leu Thr Leu Ser Leu
115 120 125

Asn Leu Pro Gly Leu Ala Asn Gly Asp Ser His Thr Val Val Asn Ser
130 135 140

Pro Thr Arg Ser Thr Val Arg Thr Gly Val Asn Asn Leu Leu Ser Lys
145 150 155 160

Trp Asn Asn Thr Tyr Ala Gly Glu Tyr Gly Asn Thr Gln Ala Glu Leu
165 170 175

Gln Tyr Asp Glu Thr Met Ala Tyr Ser Met Ser Gln Leu Lys Thr Lys
180 185 190

Phe Gly Thr Ser Phe Glu Lys Ile Ala Val Pro Leu Asp Ile Asn Phe
195 200 205

Asp Ala Val Asn Ser Gly Glu Lys Gln Val Gln Ile Val Asn Phe Lys
210 215 220

Gln Ile Tyr Tyr Thr Val Ser Val Asp Glu Pro Glu Ser Pro Ser Lys
225 230 235 240

Leu Phe Ala Glu Gly Thr Thr Val Glu Asp Leu Lys Arg Asn Gly Ile

-continued

```
                245                 250                 255

Thr Asp Glu Val Pro Pro Val Tyr Val Ser Ser Val Ser Tyr Gly Arg
            260                 265                 270

Ser Met Phe Ile Lys Leu Glu Thr Ser Ser Arg Ser Thr Gln Val Gln
        275                 280                 285

Ala Ala Phe Lys Ala Ala Ile Lys Gly Val Asp Ile Ser Gly Asn Ala
    290                 295                 300

Glu Tyr Gln Asp Ile Leu Lys Asn Thr Ser Phe Ser Ala Tyr Ile Phe
305                 310                 315                 320

Gly Gly Asp Ala Gly Ser Ala Ala Thr Val Val Ser Gly Asn Ile Glu
                325                 330                 335

Thr Leu Lys Lys Ile Ile Glu Glu Gly Ala Arg Tyr Gly Lys Leu Asn
            340                 345                 350

Pro Gly Val Pro Ile Ser Tyr Ser Thr Asn Phe Val Lys Asp Asn Arg
        355                 360                 365

Pro Ala Gln Ile Leu Ser Asn Ser Glu Tyr Ile Glu Thr Thr Ser Thr
    370                 375                 380

Val His Asn Ser Ser Ala Leu Thr Leu Asp His Ser Gly Ala Tyr Val
385                 390                 395                 400

Ala Lys Tyr Asn Ile Thr Trp Glu Glu Val Ser Tyr Asn Glu Ala Gly
                405                 410                 415

Glu Glu Val Trp Glu Pro Lys Ala Trp Asp Lys Asn Gly Val Asn Leu
            420                 425                 430

Thr Ser His Trp Ser Glu Thr Ile Gln Ile Pro Gly Asn Ala Arg Asn
        435                 440                 445

Leu His Val Asn Ile Gln Glu Cys Thr Gly Leu Ala Trp Glu Trp Trp
    450                 455                 460

Arg Thr Val Tyr Asp Lys Asp Leu Pro Leu Val Gly Gln Arg Lys Ile
465                 470                 475                 480

Thr Ile Trp Gly Thr Thr Leu Tyr Pro Gln Tyr Ala Asp Glu Val Ile
                485                 490                 495

Glu


<210> SEQ ID NO 16
<211> LENGTH: 466
<212> TYPE: PRT
<213> ORGANISM: Streptococcus mitis

<400> SEQUENCE: 16

Met Ala Asn Lys Ala Val Asn Asp Phe Ile Leu Ala Met Asp Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
```

-continued

```
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Asp Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp Tyr Gln Gly Lys Glu Val Leu Thr Pro Lys Ala Trp Asn Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Asn Asp Leu Pro Leu Val
        435                 440                 445

Arg Lys Arg Thr Ile Ser Ile Trp Gly Thr Thr Leu Tyr Pro Gln Val
    450                 455                 460

Glu Asp
465


<210> SEQ ID NO 17
<211> LENGTH: 532
<212> TYPE: PRT
<213> ORGANISM: Streptococcus intermedius

<400> SEQUENCE: 17

Met Lys Thr Lys Gln Asn Ile Ala Arg Lys Leu Ser Arg Val Val Leu
1               5                   10                  15
```

-continued

```
Leu Ser Thr Leu Val Leu Ser Ser Ala Ala Pro Ile Ser Ala Ala Phe
            20                  25                  30

Ala Glu Thr Pro Thr Lys Pro Lys Ala Ala Gln Thr Glu Lys Lys Pro
        35                  40                  45

Glu Lys Lys Pro Glu Asn Ser Asn Ser Glu Ala Ala Lys Lys Ala Leu
    50                  55                  60

Asn Asp Tyr Ile Trp Gly Leu Gln Tyr Asp Lys Leu Asn Ile Leu Thr
65                  70                  75                  80

His Gln Gly Glu Lys Leu Lys Asn His Ser Ser Arg Glu Ala Phe His
                85                  90                  95

Arg Pro Gly Glu Tyr Val Val Ile Glu Lys Lys Lys Gln Ser Ile Ser
            100                 105                 110

Asn Ala Thr Ser Lys Leu Ser Val Ser Ser Ala Asn Asp Asp Arg Ile
        115                 120                 125

Phe Pro Gly Ala Leu Leu Lys Ala Asp Gln Ser Leu Leu Glu Asn Leu
    130                 135                 140

Pro Thr Leu Ile Pro Val Asn Arg Gly Lys Thr Thr Ile Ser Val Asn
145                 150                 155                 160

Leu Pro Gly Leu Lys Asn Gly Glu Ser Asn Leu Thr Val Glu Asn Pro
                165                 170                 175

Ser Asn Ser Thr Val Arg Thr Ala Val Asn Asn Leu Val Glu Lys Trp
            180                 185                 190

Ile Gln Lys Tyr Ser Lys Thr His Ala Val Pro Ala Arg Met Gln Tyr
        195                 200                 205

Glu Ser Ile Ser Ala Gln Ser Met Ser Gln Leu Gln Ala Lys Phe Gly
    210                 215                 220

Ala Asp Phe Ser Lys Val Gly Ala Pro Leu Asn Val Asp Phe Ser Ser
225                 230                 235                 240

Val His Lys Gly Glu Lys Gln Val Phe Ile Ala Asn Phe Arg Gln Val
                245                 250                 255

Tyr Tyr Thr Ala Ser Val Asp Ser Pro Asn Ser Pro Ser Ala Leu Phe
            260                 265                 270

Gly Ser Gly Ile Thr Pro Thr Asp Leu Ile Asn Arg Gly Val Asn Ser
        275                 280                 285

Lys Thr Pro Pro Val Tyr Val Ser Asn Val Ser Tyr Gly Arg Ala Met
    290                 295                 300

Tyr Val Lys Phe Glu Thr Thr Ser Lys Ser Thr Lys Val Gln Ala Ala
305                 310                 315                 320

Ile Asp Ala Val Val Lys Gly Ala Lys Leu Lys Ala Gly Thr Glu Tyr
                325                 330                 335

Glu Asn Ile Leu Lys Asn Thr Lys Ile Thr Ala Val Val Leu Gly Gly
            340                 345                 350

Asn Pro Gly Glu Ala Ser Lys Val Ile Thr Gly Asn Ile Asp Thr Leu
        355                 360                 365

Lys Asp Leu Ile Gln Lys Gly Ser Asn Phe Ser Ala Gln Ser Pro Ala
    370                 375                 380

Val Pro Ile Ser Tyr Thr Thr Ser Phe Val Lys Asp Asn Ser Ile Ala
385                 390                 395                 400

Thr Ile Gln Asn Asn Thr Asp Tyr Ile Glu Thr Lys Val Thr Ser Tyr
                405                 410                 415

Lys Asp Gly Ala Leu Thr Leu Asn His Asp Gly Ala Phe Val Ala Arg
            420                 425                 430

Phe Tyr Val Tyr Trp Glu Glu Leu Gly His Asp Ala Asp Gly Tyr Glu
```

```
        435                 440                 445

Thr Ile Arg Ser Arg Ser Trp Ser Gly Asn Gly Tyr Asn Arg Gly Ala
    450                 455                 460

His Tyr Ser Thr Thr Leu Arg Phe Lys Gly Asn Val Arg Asn Ile Arg
465                 470                 475                 480

Val Lys Val Leu Gly Ala Thr Gly Leu Ala Trp Glu Pro Trp Arg Leu
                485                 490                 495

Ile Tyr Ser Lys Asn Asp Leu Pro Leu Val Pro Gln Arg Asn Ile Ser
            500                 505                 510

Thr Trp Gly Thr Thr Leu His Pro Gln Phe Glu Asp Lys Val Val Lys
        515                 520                 525

Asp Asn Thr Asp
    530


<210> SEQ ID NO 18
<211> LENGTH: 665
<212> TYPE: PRT
<213> ORGANISM: Streptococcus mitis

<400> SEQUENCE: 18

Met Asn Gln Glu Lys Arg Leu His Arg Phe Val Lys Lys Cys Gly Leu
1               5                   10                  15

Gly Val Cys Ser Ala Val Val Ala Ala Phe Leu Leu Asn Ala Gln Gly
            20                  25                  30

Val Ala Leu Ala Thr Glu Gln Gly Asn Arg Pro Val Glu Thr Glu Asn
        35                  40                  45

Ile Ala Arg Gly Lys Gln Ala Ser Gln Ser Ser Thr Ala Tyr Gly Gly
    50                  55                  60

Ala Ala Thr Arg Ala Val Asp Gly Asn Val Asp Ser Asp Tyr Gly His
65                  70                  75                  80

His Ser Val Thr His Thr Asn Phe Glu Asp Asn Ala Trp Trp Gln Val
                85                  90                  95

Asp Leu Gly Lys Thr Glu Asn Val Gly Lys Val Lys Leu Tyr Asn Arg
            100                 105                 110

Gly Asp Gly Asn Val Ala Asn Arg Leu Ser Asn Phe Asp Val Val Leu
        115                 120                 125

Leu Asn Glu Ala Lys Gln Glu Val Ala Arg Gln His Phe Asp Ser Leu
    130                 135                 140

Asn Gly Lys Ala Glu Leu Glu Val Phe Phe Thr Ala Lys Asp Ala Arg
145                 150                 155                 160

Tyr Val Lys Val Glu Leu Lys Thr Lys Asn Thr Pro Leu Ser Leu Ala
                165                 170                 175

Glu Val Glu Val Phe Arg Ser Ala Thr Thr Gln Val Gly Gln Asp Arg
            180                 185                 190

Thr Ala Pro Val Val Asp Gln Thr Ser Ala Leu Lys Asp Tyr Leu Phe
        195                 200                 205

Gly Leu Thr Tyr Asn Pro Leu Asp Ile Leu Thr Arg Lys Gly Glu Thr
    210                 215                 220

Leu Glu Asn Arg Tyr Asn Thr Ser Ala Lys Glu Gln Asn Gly Glu Phe
225                 230                 235                 240

Val Val Val Glu Lys Ile Lys Lys Thr Leu Ser Thr Gly Thr Ala Asp
                245                 250                 255

Val Ser Ile Asn Gly Asn Gln Asn Val Phe Leu Gly Gly Leu Tyr Lys
            260                 265                 270
```

-continued

```
Ala Asn Gln Asn Leu Leu Glu Asn Gln Pro Glu Leu Ile Ser Leu Ala
        275                 280                 285

Arg Ala Lys Gly Thr Val Ser Val Asp Leu Pro Gly Met Ile His Ser
    290                 295                 300

Glu Asn Lys Ile Glu Ala Asn Pro Thr Thr Ser Gly Met Gln Glu Ala
305                 310                 315                 320

Met Asn Thr Leu Val Glu Lys Trp Thr Lys Asn Tyr Ser Ser Ser His
                325                 330                 335

Ser Val Pro Ala Arg Val Gln Tyr Glu Ser Thr Thr Ala Tyr Ser Met
            340                 345                 350

Asn Gln Leu Lys Ala Lys Phe Gly Ala Asp Phe Glu Lys Ala Gly Ala
        355                 360                 365

Pro Leu Lys Ile Asp Phe Glu Ala Val Gln Lys Gly Glu Lys Gln Ile
    370                 375                 380

Glu Val Val Asn Phe Lys Gln Ile Tyr Tyr Thr Ala Thr Phe Asp Ala
385                 390                 395                 400

Pro Thr Asn Pro Ala Ala Val Phe Asp Lys Ser Val Thr Pro Glu Asp
                405                 410                 415

Leu Lys Gln Arg Gly Val Asp Ser Gln Thr Pro Pro Val Tyr Val Ser
            420                 425                 430

Asn Val Ser Tyr Gly Arg Gln Ile Tyr Val Lys Phe Glu Ser Thr Ser
        435                 440                 445

Lys Ser Thr Glu Leu Lys Ala Ala Ile Asn Ala Val Ile Lys Gly Ala
    450                 455                 460

Thr Ile Ala Pro Asn Ser Glu Trp Ser Arg Leu Leu Lys Asn Thr Ser
465                 470                 475                 480

Val Thr Ala Val Ile Val Gly Gly Asn Ala Ser Gly Ala Ala Lys Val
                485                 490                 495

Val Thr Gly Thr Val Glu Asn Leu Lys Glu Leu Ile Arg Glu Gly Ala
            500                 505                 510

Asn Phe Ser Ala Gln Ser Pro Ala Val Pro Ile Ser Tyr Lys Thr Ala
        515                 520                 525

Phe Leu Lys Asp Asn Ala Gln Ala Thr Leu Gln Asn Ser Thr Asp Tyr
    530                 535                 540

Ile Glu Thr Lys Val Thr Ser Tyr Lys Asn Gly Phe Leu Lys Leu His
545                 550                 555                 560

His Lys Gly Ala Tyr Ile Ala Arg Tyr Tyr Ile Tyr Trp Asp Glu Ile
                565                 570                 575

Thr Tyr Asp Glu Gln Gly Asn Pro Glu Ile Arg Ser Arg Gln Trp Glu
            580                 585                 590

Asp Asn Gly Lys Asn Arg Thr Ser Gly Phe Gln Thr Glu Ile Gln Phe
        595                 600                 605

Arg Gly Asn Val Arg Asn Leu Arg Ile Lys Val Gln Glu Lys Thr Gly
    610                 615                 620

Leu Val Trp Glu Pro Trp Arg Thr Val Tyr Asn Arg Thr Asp Leu Pro
625                 630                 635                 640

Leu Val Gln Gln Arg Thr Ile Thr His Trp Gly Thr Thr Leu Asn Pro
                645                 650                 655

Lys Val Asp Glu Lys Ile Val Asn Glu
            660                 665
```

<210> SEQ ID NO 19
<211> LENGTH: 534
<212> TYPE: PRT

<213> ORGANISM: Arcanobacterium pyogenes

<400> SEQUENCE: 19

Met Lys Arg Lys Ala Phe Ala Ser Leu Val Ala Ser Val Val Ala Ala
1 5 10 15

Ala Thr Val Thr Met Pro Thr Ala Ser Phe Ala Ala Gly Leu Gly Asn
20 25 30

Ser Ser Gly Leu Thr Asp Gly Leu Ser Ala Pro Arg Ala Ser Ile Ser
35 40 45

Pro Thr Asp Lys Val Asp Leu Lys Ser Ala Gln Glu Thr Asp Glu Thr
50 55 60

Gly Val Asp Lys Tyr Ile Arg Gly Leu Lys Tyr Asp Pro Ser Gly Val
65 70 75 80

Leu Ala Val Lys Gly Glu Ser Ile Glu Asn Val Pro Val Thr Lys Asp
85 90 95

Gln Leu Lys Asp Gly Thr Tyr Thr Val Phe Lys His Glu Arg Lys Ser
100 105 110

Phe Asn Asn Leu Arg Ser Asp Ile Ser Ala Phe Asp Ala Asn Asn Ala
115 120 125

His Val Tyr Pro Gly Ala Leu Val Leu Ala Asn Lys Asp Leu Ala Lys
130 135 140

Gly Ser Pro Thr Ser Ile Gly Ile Ala Arg Ala Pro Gln Thr Val Ser
145 150 155 160

Val Asp Leu Pro Gly Leu Val Asp Gly Lys Asn Lys Val Val Ile Asn
165 170 175

Asn Pro Thr Lys Ser Ser Val Thr Gln Gly Leu Asn Gly Leu Leu Asp
180 185 190

Gly Trp Ile Gln Arg Asn Ser Lys Tyr Pro Asp His Ala Ala Lys Ile
195 200 205

Ser Tyr Asp Glu Thr Met Val Thr Ser Lys Arg Gln Leu Glu Ala Lys
210 215 220

Leu Gly Leu Gly Phe Glu Lys Val Ser Ala Lys Leu Asn Val Asp Phe
225 230 235 240

Asp Ala Ile His Lys Arg Glu Arg Gln Val Ala Ile Ala Ser Phe Lys
245 250 255

Gln Ile Tyr Tyr Thr Ala Ser Val Asp Thr Pro Thr Ser Pro His Ser
260 265 270

Val Phe Gly Pro Asn Val Thr Ala Gln Asp Leu Lys Asp Arg Gly Val
275 280 285

Asn Asn Lys Asn Pro Leu Gly Tyr Ile Ser Ser Val Ser Tyr Gly Arg
290 295 300

Gln Ile Phe Val Lys Leu Glu Thr Thr Ser Thr Ser Asn Asp Val Gln
305 310 315 320

Ala Ala Phe Ser Gly Leu Phe Lys Ala Lys Phe Gly Asn Leu Ser Thr
325 330 335

Glu Phe Lys Ala Lys Tyr Ala Asp Ile Leu Asn Lys Thr Arg Ala Thr
340 345 350

Val Tyr Ala Val Gly Gly Ser Ala Arg Gly Gly Val Glu Val Ala Thr
355 360 365

Gly Asn Ile Asp Ala Leu Lys Lys Ile Ile Lys Glu Glu Ser Thr Tyr
370 375 380

Ser Thr Lys Val Pro Ala Val Pro Val Ser Tyr Ala Val Asn Phe Leu
385 390 395 400

-continued

```
Lys Asp Asn Gln Leu Ala Ala Val Arg Ser Ser Gly Asp Tyr Ile Glu
                405                 410                 415

Thr Thr Ala Thr Thr Tyr Lys Ser Gly Glu Ile Thr Phe Arg His Gly
            420                 425                 430

Gly Gly Tyr Val Ala Lys Phe Arg Leu Lys Trp Asp Glu Ile Ser Tyr
        435                 440                 445

Asp Pro Gln Gly Lys Glu Ile Arg Thr Pro Lys Thr Trp Ser Gly Asn
    450                 455                 460

Trp Ala Ala Arg Thr Leu Gly Phe Arg Glu Thr Ile Gln Leu Pro Ala
465                 470                 475                 480

Asn Ala Arg Asn Ile His Val Glu Ala Gly Glu Ala Thr Gly Leu Ala
                485                 490                 495

Trp Asp Pro Trp Trp Thr Val Ile Asn Lys Lys Asn Leu Pro Leu Val
            500                 505                 510

Pro His Arg Glu Ile Val Leu Lys Gly Thr Thr Leu Asn Pro Trp Val
        515                 520                 525

Glu Asp Asn Val Lys Ser
    530
```

<210> SEQ ID NO 20
<211> LENGTH: 1416
<212> TYPE: DNA
<213> ORGANISM: Streptococcus pneumoniae

<400> SEQUENCE: 20

```
ctagtcattt tctaccttat cctctacctg aggatagaga gttgttcccc aaatagaaat     60

cgtccgctta cgcactagtg gcaaatcggt tttttcataa accgtacgcc accattccca    120

ggcaagcccg gtacactctc taattttgac agagagatta cgaacattcc cttttaaagg    180

aatactagtg gtaaagtgag ccgtcaaatc ctgcccattt ctgtcccaag ccttaggagt    240

caagacttcc ttaccttgat gatcatagga taattcatcc caagtaatat aatattgggc    300

aacataggca ccactatgat ccagcagtaa atctccgttt ctgtaagctg taaccttagt    360

ctcaacatag tctgtactgt tttgaaaggt cgcaactaca ttgtcacgta aaaaagaagt    420

tgtataggaa atcggcaagc ctggatgatc tgctgtaaag cgactgcctt cttgaatcaa    480

gtcctctacc atatccacct tgcctgttac aactcgggca cccgaacttg ggtcgccccc    540

taaaataacc gccttcactt ctgtattgtc caaaatctgc ttccactctg tctgaggagc    600

taccttgact ccttttatca aagcttcaaa agcagcctct acttcatcac tcttactcgt    660

ggtttccaac ttgagataga cttggcgccc ataagcaaca ctcgaaatat agaccaaagg    720

acgctctgca gaaattcctc tctgttttaa atcctctacc gttacagtat cttgaaacac    780

atctcctgga tttttaacag cgtctacgct gactgtataa taaatctgct taaaattaac    840

aatctgaatc tgcttttcac ctgaatggac agagttaaaa tcaatatcaa gagaattccc    900

tgtcttttca aagtcagaac caaacttgac cttgagttgt tccatgctgt gagccgttat    960

tttttcatac tgcattctag ctgggacatt attgacctga ccataatctt gatgccactt   1020

agccaacaaa tcgtttaccg ctccgcgaac acttgaattg ctggggtctt ccacttggag   1080

aaagctatcg ctacttgcca aaccaggcaa atcaatacta taagtcatcg gagcacgatc   1140

aaccgcaaga agagtgggat tattctctaa caaggtctca tccactacga gaagtgctcc   1200

aggatagagg cgactgtcgt tggtagctgt tacagaaata tcacttgtat ttgtcgacaa   1260

gctccgcttc tttctttcga taacaacaaa ctcatcgggt agctgattac cctctttgat   1320
```

-continued gaaacgattt tcaatacttt ctccctgatg ggtcaagagt ttctttttat cgtaattcat 1380
agctagtata aagtcattta ctgctttatt tgccat 1416

<210> SEQ ID NO 21
<211> LENGTH: 1530
<212> TYPE: DNA
<213> ORGANISM: Bacillus cereus

<400> SEQUENCE: 21
ctgaatatta agaaaaacac taaaagaaga aagttccttg catgtttatt agttagttta 60
tgcactatta attattcatc tatttccttc gcagaaacac aagcaagtaa tgcaactgat 120
gtaaccaaaa atgctagtgg cattgatact ggtatagcaa atcttaaata taataatcaa 180
gaggttttag ctgtaaatgg tgataaagta gaaagttttg ttccgaaaga aagtatcaat 240
tcaaatggta aatttgtagt agtggaacgc gagaaaaaat cacttacaac gtcaccagtc 300
gatatttcaa ttattgattc tgtagtgaat cgcacgtatc caggagctgt acaacttgca 360
aataaagctt ttgcagacaa tcaaccaagt ttattagtgg ctaagagaaa gcctttgaat 420
attagtatag acttaccggg catgagaaaa gaaaatacaa tcactgtcca aaatccgaca 480
tatggtaatg tagctggagc agtagacgat ttagtatcta cttggaatga aaagtattct 540
acaacacata cgttacctgc aagaatgcag tatacggaat ctatggttta tagtaaatca 600
caaatagcaa gtgctcttaa tgttaacgct aaatatcttg ataacagtct aaacattgat 660
tttaatgcgg ttgcaaatgg agagaaaaaa gtgatggtag cggcgtataa gcaaatattt 720
tatacggtaa gtgctgaact acctaacaat ccatccgacc tttttgataa tagcgttact 780
tttgacgagt taactcgaaa aggcgtaagt aattcggctc cacctgttat ggtttcaaat 840
gtagcttatg gtagaacgat ttatgtaaaa ttagaaacaa catctaagag caaagatgta 900
caagctgctt ttaaagcctt acttaagaat aacagcgttg aaacaagtgg acagtataaa 960 gatattttg aagaaagtac ctttactgct gtagtattag gcggagatgc gaaagagcat 1020
aacaaggttg ttactaaaga tttcaatgaa atccgaaata tcattaaaga taatgctgaa 1080
ttaagtctta aaaatccagc atacccaatt tcatatacaa gcactttctt aaaagataat 1140
tcaactgctg ctgttcataa caatacagat tatattgaga cgacaactac agaatattca 1200
agtgctaaaa tgacacttga tcattacggt gcttacgttg ctcaatttga tgtatcttgg 1260
gatgaattca catttgacca aaagggtaac gaagtactaa cacataaaac gtgggatggt 1320
agcggaaaag acaaaacggc tcattactct acagttatcc cactcccacc aaattcaaaa 1380
aatataaaaa ttgtagcaag agaatgtaca ggtcttgcat gggaatggtg gagaacaatt 1440
attaatgaac aaaatgttcc attaacaaat gaaataaaag tttcaattgg aggaacaaca 1500
ttatacccaa cagctagtat tagtcattaa 1530

<210> SEQ ID NO 22
<211> LENGTH: 1539
<212> TYPE: DNA
<213> ORGANISM: Bacillus anthracis

<400> SEQUENCE: 22
ctaatgacta atagtagcag ttggatataa tgttgttcct ccaattgaaa cctttatttc 60
atttgttaat ggaacatttt gttcattaat gatagttctc caccattccc atgcaagacc 120
tgtacattct cttgcaacga tttttatatt ttttgaattt ggtggaagag ggataactgt 180
agagtaatgg gctgttttgt ctttgccact accttcccat gttttatgtg ttagtacttc 240

```
tttcccattt tgatcaaatg taaattcatc ccaagataca tcaaattgag caacgtaagc    300
accgtaatga tcgagtgtca ttttagcact tgaatattct gtagttgtcg tctcgatata    360
atctgtattg ttatgaacag cagcagttgc attatctttt aagaacgtgc ttgtatatga    420
aattgggtat gctggatttt taaagcttaa ttcagcatta tctttaataa tatttcggat    480
ttcattgaaa tcttttgtaa caaccttgtt atgctctttc gcatctccgc ctaatactac    540
agcagtaaag gtactttctt caaaaatatc tttgtactgt ccactcgttt cgacgctgtt    600
attcttaagt agagctttaa atgcagcttg tacatcttta ctcttagatg ttgtttctaa    660
ttttacataa accgttctac cataagctac atttgaaacc ataacaggtg gagccgaatt    720
acttactcct ttacgagtta actcatcaaa agtaacacta ttatcaaaga gatcagatgg    780
attattaggt agttcagcac ttacagtata aaatatttgt ttatatgccg ccaccatcac    840
tttcttttct ccatttgcaa ctgcattaaa gtcaatattt agactgttat caagatattt    900
agcattaaca ttaagagcac ttgcgatttg tgatttacta taaaccatag attctgtata    960
ctgcattctt gcaggtaacg tatgtgttgt ggaatacttt tcattccaag tagatactaa   1020
atcatctact gctccagcca cattaccata tgtcggattt tggacagtga ttgtattttc   1080
ttttctcatg ccaggtaagt ctatactaat attcaaaggc tttctcttag ctactaataa   1140
actcggttga ttgtctgcaa atgctttatt ggcaagttgt acagctcctg gatacgtacg   1200
attcactaca gaatcaataa tcaaaatatc gactggtgac gttgtaagtg atttttttctc  1260
gcgttccact actacaaatt taccgtttga attgatactc tctttcggaa taaaactctc   1320
tactttatca ccatttactg ctaaaatatc tctactatca tactttagat ttgctatacc   1380
agtattaata tcactagcat tttttattgc accagttgca ttaccggctt gtgtttctgc   1440
aaaagaaata gacgaataat gaatggtaca tagactaact aataaacatg caaggaactt   1500
tcttctttta gtgtttttct taatattcag aaaaatcac                          1539
```

<210> SEQ ID NO 23
<211> LENGTH: 1530
<212> TYPE: DNA
<213> ORGANISM: Bacillus thuringiensis

<400> SEQUENCE: 23

```
ctgaatatta agaaaaacac taaaagaaga aagttccttg catgtttatt agttagtcta     60
tgcaccatta attattcatc tatttccttc gcagaaacac aagcaagtaa tgcgactgat    120
gtaaccaaaa atgctagtgg cattgatact ggtatagcaa atcttaaata taatattcaa    180
gaggttttag ctgtaaatgg tgataaagta gaaagttttg ttccgaaaga aagtatcaat    240
tcaaatggta aatttgtagt agtggaacgc gagaaaaaat cacttacaac gtcaccagtc    300
gatatttcaa ttattgattc tgtggtgaat cgcacgtatc caggagctgt acaacttgct    360
aataaagctt ttgcagacaa tcaaccgagt ttattagtgg ctaagagaaa gcctttgaat    420
attagtatag acttaccggg catgagaaaa gaaaatacaa tcactgtcca aaatccgaca    480
tatggtaatg tagctggagc agtagacgat ttagtatcta cttggaatga aaagtattct    540
acaacacata cgttacctgc aagaatgcag tatacggaat ctatggttta tagtaaatca    600
caaattgcaa gtgctcttaa tgttaacgct aaatatcttg ataacagtct aaatattggt    660
tttaatgcgg ttgcaaatgg agagaaaaaa gtgatggtag cggcgtataa gcaaatattt    720
tatacggtaa gtgctgaact acctaacaat ccatccgacc tttttgataa tagcgttact    780
```

```
tttgacgagt taactcgaaa aggcgtaaat aattcggctc cacctgttat ggtttcaaat    840

gtagcttatg gtagaacgat ttatgtaaaa ttagaaacaa catctaagag caaagatgta    900

caagctgctt ttaaagcctt acttaagaat aacagcgttg aaacaagtgg acagtataaa    960

gatatttttg aagaaagtac ctttactgct gtagtattag gcggagatgc gaaagaacat   1020

aacaaggttg ttactaaaga tttcaatgaa atccgaaata ttattaaaga taatgctgaa   1080

ttaagtctta aaaatccagc atacccaatt tcatatacaa gtactttctt aaaagataat   1140

gcaactgctg ctgttcataa caatacagat tatattgaga cgacaactac agaatattca   1200

agtgctaaaa tgacacttga tcattacggt gcttacgttg ctcaatttga tgtatcttgg   1260

gatgaattca catttgatca aaagggtaac gaagtactaa cacataaaac gtgggatggt   1320

agtggaaaag acaaaacggc tcattactct acagttatcc ctcttccacc gaattcaaaa   1380

aatataaaaa ttgtagcaag agaatgtaca ggtcttgcat gggaatggtg gagaacaatt   1440

attaatgaac aaaacgttcc attaacaaat gaaataaaag tttcaattgg aggaacaaca   1500

ttatacccaa cagctagtat tagtcattaa                                    1530
```

<210> SEQ ID NO 24
<211> LENGTH: 1503
<212> TYPE: DNA
<213> ORGANISM: Clostridium perfringens

<400> SEQUENCE: 24

```
atgataagat ttaagaaaac aaaattaata gcaagtattg caatggcttt atgtctgttt     60

tctcaaccag taatcagttt ctcaaaggat ataacagata aaaatcaaag tattgattct    120

ggaatatcaa gtttaagtta caatagaaat gaagttttag ctagtaatgg agataaaatt    180

gaaagctttg ttccaaagga aggtaaaaaa gctggtaata aatttatagt tgtagaacgt    240

caaaaaagat cccttacaac atcaccagta gatatatcaa taattgattc tgtaaatgac    300

cgtacatatc caggagcatt acaacttgca gataaagcat ttgtggaaaa tagacctaca    360

atcttaatgg taaaaagaaa gcctattaac attaatatag atttaccagg attaaagggc    420

gaaaatagta taaaggttga tgatccaacc tatggaaaag tttctggagc aattgatgaa    480

ttagtatcta agtggaatga aaagtattca tctacacata ctttaccagc aagaactcaa    540

tattcagaat ctatggttta tagtaaatca caaatatcaa gtgcccttaa tgttaatgct    600

aaagtccttg aaaactcact tggagtagac tttaatgcag tagcaaacaa tgagaaaaaa    660

gttatgattt tagcatataa acaaatattc tatacagtaa gtgcagattt acctaagaat    720

ccatcagatc tttttgatga cagtgttaca tttaatgatt taaaacaaaa gggagtaagt    780

aatgaagcac ctccacttat ggtttcaaat gtagcttatg gaagaacaat atatgttaag    840

ttagaaacta cttctagtag taaagatgta caagctgctt tcaaagctct tataaagaac    900

actgatataa aaaatagtca acaatataaa gatatttatg aaaatagttc cttcacagca    960

gtagttttag gaggagatgc acaagaacat aacaaagttg taactaaaga ctttgatgaa   1020

ataagaaaag taattaaaga caatgcaact tttagtacaa aaaacccagc atatccaata   1080

tcttatacta gtgttttctt aaaagataac tcagttgctg ctgttcacaa taaaacagat   1140

tatatagaaa caacttctac agagtattct aagggaaaaa taaacttaga tcatagtgga   1200

gcctatgttg cacagtttga agtagcctgg gatgaagttt catatgacaa agaaggaaat   1260

gaagttttaa ctcataaaac atgggatgga aattatcaag ataaaacagc tcactattca   1320

acagtaatac ctcttgaagc taatgcaaga aatataagaa taaaagcaag agagtgtaca   1380
```

ggccttgctt gggaatggtg gagagatgtt ataagtgaat atgatgttcc attaacaaat 1440
aatataaatg tttcaatatg gggaacaact ttataccctg gatctagtat tacttacaat 1500
taa 1503

<210> SEQ ID NO 25
<211> LENGTH: 1506
<212> TYPE: DNA
<213> ORGANISM: Bacillus alvei

<400> SEQUENCE: 25
atgaagaaaa aatcaaacca cttgaaagga aggaaagtac tcgtaagttt gttagtaagc 60
ttacaagtgt tcgcttttgc gagtatttcc tccgcagcac caaccgaacc caatgatatt 120
gatatgggga tcgcaggact gaactataat cgcaatgagg ttttggctat tcaaggggat 180
caaatcagta gttttgttcc caaagaaggc attcagtcca atggcaaatt tatcgtggtt 240
gaacgggaca aaaaatcact cacaacgtca cccgtagata tttccatcgt tgattcaatc 300
acgaatcgca cgtatccagg cgcaatacag cttgcaaata aggattttgc cgataatcag 360
cctagtctgg ttatggctgc gagaaaacca ttagatatta gcatcgatct gcctggtttg 420
aagaacgaga atacaatttc cgttcaaaat ccaaattacg gcactgtatc tagtgccatt 480
gatcagctcg tgtcgacttg ggcgagaaag tattccagca cgcatacact gcctgcaaga 540
ttacaatacg ctgaatccat ggtttacagc caaaatcaaa tttccagcgc cctgaatgtg 600
aacgctaaag tactgaacgg tacactcgga atcgacttta acgcggttgc aaatggcgag 660
aaaaaagtga tggttgctgc ttacaagcaa atcttttata ccgtaagtgc aggactgccc 720
aacaatccat cagacttgtt cgatgacagt gtgacatttg ctgagttagc tcgcaaggga 780
gtaagcaatg aggcaccgcc gctgatggta tctaacgtgg cttacggcag aactatttac 840
gtaaaattgg aaacaacttc taagagcaat gacgtacaaa cggcatttaa attgttgctc 900
aataatccta gcatacaagc tagcggacag tacaaagata tttatgagaa cagctcgttt 960
actgccgttg tactaggcgg cgacgcgcaa acccataacc aagtcgttac gaaagacttc 1020
aatgttatcc aaagtgtaat caaggacaat gcacaattta gcagcaagaa ccctgcttac 1080
ccgatttcat atacaagtgt cttcttgaaa gacaattcca ttgctgctgt tcacaacaat 1140
accgagtata tcgagacgaa aacgacggaa tattcgaagg gtaaaattaa gcttgatcat 1200
agtggtgcat atgtagctca gtttgaagta tattgggatg aattttcata tgatgcagat 1260
ggacaagaaa tcgtgactcg taaaagttgg gatggaaatt ggcgcgatag atctgctcat 1320
ttctcaacag aaatcccact tcctcctaat gccaagaaca taagaatttt tgcgagagaa 1380
tgcacaggtc ttgcttggga atggtggaga acagttgttg atgaatataa cgttccgtta 1440
gcaagcgata ttaatgtttc gatttgggga acaacgttat atccgaaatc atccattact 1500
cactaa 1506

<210> SEQ ID NO 26
<211> LENGTH: 1725
<212> TYPE: DNA
<213> ORGANISM: Streptococcus canis

<400> SEQUENCE: 26
atgaaggaca tgtctaataa aaaaatattt aaaaaataca gtcgcgtcgc tgggctatta 60
acggcagctc ttatcgttgg taatcttgtt actgctaatg ctgactcgaa caaacaaaac 120

-continued

```
actgccaata cagaaaccac aacgacaaat gaacaaccaa aaccagaaag tagtgagcta    180

actacagaaa aagcaggtca gaaaatggat gatatgctta actctaacga tatgattaag    240

cttgctccca aagaaatgcc actagaatct gcagaaaaag aagaaaaaaa gtcagaagac    300

aataaaaaaa gcgaagaaga tcatactgaa gaaatcaatg acaagattta ttcactaaat    360

tataatgagc ttgaagtact tgctaaaaat ggtgaaacca ttgaaaactt tgttcctaaa    420

gaaggcgtta agaaagctga caaatttatt gtcattgaaa gaaagaaaaa aaatatcaac    480

actacaccgg tcgatatttc catcattgac tctgtcactg ataggaccta tccagcagcc    540

cttcagctgg ctaataaagg ttttaccgaa aacaaaccag acgcagtagt caccaagcga    600

aacccacaaa aaatccatat tgatttacca ggtatgggag acaaagcaac ggttgaggtc    660

aatgacccta cctatgccaa tgtttcaaca gctattgata atcttgttaa ccaatggcat    720

gataattatt ctggtggtaa tacgcttcct gccagaacac aatatactga atcaatggta    780

tattctaaat cacagattga agcagctcta aatgttaata gtaaaatctt agatggtact    840

ttaggcattg atttcaagtc gatttcaaaa ggtgaaaaga aggtgatgat tgcagcatac    900

aagcaaattt tttacaccgt atcagcaaac cttcctaata atcctgcgga tgtgtttgat    960

aaatcagtga cctttaaaga gttgcaagca aaaggtgtca gcaatgaagc cccgccactc   1020

tttgtgagta acgtagctta tggtcgaact gtttttgtca aactagaaac aagttctaaa   1080

agtaatgatg ttgaagcggc ctttagtgca gctctaaaag gaacagatgt taaaactaat   1140

ggaaaatact ctgatatttt agaaaatagt tcatttacag ctgtcgtttt aggagcagat   1200

gctgcagagc acaataaggt agtcacaaaa gactttgatg ttattagaaa cgttatcaaa   1260

gctaatgcta ccttcagtag aaaaaaccca gcttatccta tttcatacac cagtgttttc   1320

cttaaaaata ataaaattgc gggtgtcaat aacagaagtg aatacgttga aacaacatct   1380

accgagtaca cgagtggaaa aattaacctg tctcatcaag gtgcctatgt tgctcaatat   1440

gaaatccttt gggatgaaat caattatgat gacaaaggaa aagaagtgat tactaaacga   1500

cgttgggaca acaactggta tagtaagaca tcaccattta gcacagttat cccactagga   1560

gctaattcac gaaatatccg tatcatggct agagagtgca ccggcttagc ttgggaatgg   1620

tggcgaaaag tgatcgacga aagagatgtg aaactgtcta aagaaatcaa tgtcaacatc   1680

tcaggatcaa ccctgagccc atatggttcg attacttata agtag                   1725


<210> SEQ ID NO 27
<211> LENGTH: 1715
<212> TYPE: DNA
<213> ORGANISM: Streptococcus equisimilis

<400> SEQUENCE: 27

atgtctaata aaaaaatatt taaaaaatac agtcgcgtcg ctgggctatt aacggcagct     60

cttatcgttg gtaatcttgt tactgctaat ctgactcgaa caaacaaaac actgccaata    120

cagaaaccac aacgacaaat gaacaaccaa aaccagaaag tagtgagcta actacagaaa    180

aagcaggtca gaaaatggat gatatgctta actctaacga tatgattaag cttgctccca    240

aagaaatgcc actagaatct gcagaaaaag aagaaaaaaa gtcagaagac aataaaaaaa    300

gcgaagaaga tcatactgaa gaaatcaatg acaagattta ttcactaaat tataatgagc    360

ttgaagtact tgctaaaaat ggtgaaacca ttgaaaactt tgttcctaaa gaaggcgtta    420

agaaagctga caaatttatt gtcattgaaa gaaagaaaaa aaatatcaac actacaccgg    480

tcgatatttc catcattgac tctgtcactg ataggaccta tccagcagcc cttcagctgg    540
```

-continued ctaataaagg ttttaccgaa aacaaaccag acgcagtagt caccaagcga aacccacaaa 600
aaatccatat tgatttacca ggtatgggag ataaagcaac ggttgaggtc aatgacccta 660
cctatgccaa tgtttcaaca gctattgata atcttgttaa ccaatggcat gataattatt 720
ctggtggtaa tacgcttcct gccagaacac aatatactga atcaatggta tattctaaat 780
cacagattga agcagctcta aatgttaata gtaaaatctt agatggtact ttaggcattg 840
atttcaagtc gatttcaaaa ggtgaaaaga aggtgatgat tgcagcatac aagcaaattt 900
tttacaccgt atcagcaaac cttcctaata atcctgcgga tgtgtttgat aaatcagtga 960
cctttaaaga gttgcaacga aaaggtgtca gcaatgaagc cccgccactc tttgtgagta 1020
acgtagctta tggtcgaact gtttttgtca aactagaaac aagttctaaa agtaatgatg 1080
ttgaagcggc ctttagtgca gctctaaaag gaacagatgt taaaactaat ggaaaatact 1140
ctgatatttt agaaaatagt tcatttacag ctgtcgtttt aggaggagat gctgcagagc 1200
acaataaggt agtcacaaaa gactttgatg ttattagaaa cgttatcaaa gataatgcta 1260
cattcagtag aaaaaaccca gcttatccta tttcatacac cagtgttttc cttaaaaata 1320
ataaaattgc gggtgtcaat aacagaagtg aatacgttga aacaacatct accgagtaca 1380
cgagtggaaa aattaacctg tctcatcaag gtgcctatgt tgctcaatat gaaatccttt 1440
gggatgaaat caattatgat gacaaaggaa aagaagtgat tacaaaacga cgttgggaca 1500
acaactggta tagtaagaca tcaccattta gcacagttat ccccactagga gctaattcac 1560 gaaatatccg tatcatggct agagagtgca ccggattagc ttgggaatgg tggcgaaaag 1620
tgatcgacga aagagatgtg aaactgtcta aagaaatcaa tgtcaacatc tcaggatcaa 1680
ccttgagccc atatggttcg attacttata agtag 1715

<210> SEQ ID NO 28
<211> LENGTH: 1716
<212> TYPE: DNA
<213> ORGANISM: Streptococcus pyogenes

<400> SEQUENCE: 28
atgtctaata aaaaaacatt taaaaaatac agtcgcgtcg ctgggctact aacggcagct 60
cttatcattg gtaatcttgt tactgctaat gctgaatcga acaaacaaaa cactgctagt 120
acagaaacca caacgacaag tgagcaacca aaaccagaaa gtagtgagct aactatcgaa 180
aaagcaggtc agaaaatgga tgatatgctt aactctaacg atatgattaa gcttgctccc 240
aaagaaatgc cactagaatc tgcagaaaaa gaagaaaaaa agtcagaaga caaaaaaaag 300
agcgaagaag atcacactga agaaatcaat gacaagattt attcactaaa ttataatgag 360
cttgaagtac ttgctaaaaa tggtgaaacc attgaaaatt ttgttcctaa agaaggcgtt 420
aagaaagctg ataaatttat tgtcattgaa agaaagaaaa aaaatatcaa cactacacca 480
gtcgatattt ccattattga ctctgtcact gataggacct atccagcagc ccttcagctg 540
gctaataaag gttttaccga aaacaaacca gacgcggtag tcaccaagcg aaacccacaa 600
aaaatccata ttgatttacc aggtatggga gacaaagcaa cggttgaggt caatgaccct 660
acctatgcca atgtttcaac agctattgat aatcttgtta accaatggca tgataattat 720
tctggtggta atacgcttcc tgccagaaca caatatactg aatcaatggt atattctaag 780
tcacagattg aagcagctct aaatgttaat agcaaaatct tagatggtac tttaggcatt 840
gatttcaagt cgatttcaaa aggtgaaaag aaggtgatga ttgcagcata caagcaaatt 900

-continued

```
ttttacaccg tatcagcaaa ccttcctaat aatcctgcgg atgtgtttga taaatcagtg    960

acctttaaag atttgcaacg aaaaggtgtc agcaatgaag ctccgccact ctttgtgagt   1020

aacgtagcct atggtcgaac tgtttttgtc aaactagaaa caagttctaa aagtaatgat   1080

gttgaagcgg cctttagtgc agctctaaaa ggaacagatg ttaaaacgaa tggaaaatac   1140

tctgatatct tagaaaatag ctcatttaca gctgtcgttt taggaggaga tgctgcagag   1200

cacaataagg tggtcacaaa agactttgat gttattagaa acgttatcaa agacaatgct   1260

accttcagta gaaaaaaccc agcttatcct atttcataca ccagtgtttt ccttaaaaat   1320

aataaaattg cgggtgtcaa taacagaact gaatacgttg aaacaacatc taccgagtac   1380

actagtggaa aaattaacct gtctcatcaa ggcgcgtatg ttgctcaata tgaaatcctt   1440

tgggatgaaa tcaattatga tgacaaagga aaagaagtga ttacaaaacg acgttgggac   1500

aacaactggt atagtaagac atcaccattt agcacagtta tcccactagg agctaattca   1560

cgaaatatcc gtatcatggc tagagagtgc accggcttag cttgggaatg gtggcgaaaa   1620

gtgatcgacg aaagagatgt gaaactatct aaagaaatca atgtcaacat ctcaggatca   1680

accttgagcc catatggttc gattacttat aagtag                             1716
```

<210> SEQ ID NO 29
<211> LENGTH: 1545
<212> TYPE: DNA
<213> ORGANISM: Clostridium novyi

<400> SEQUENCE: 29

```
atgaagaaat ctttaaaaac tataattcgt agcatatctt ttctctcaat attaacatta     60

acttgtagtt gcaactttat aacaagcacc cagaaaaatg taagcttatt atcgggacct    120

aataaagtta ttaaacctaa gaaaactaaa tccttagatg ataggattta tggattaaaa    180

tatgatccta ataaaatact atcatttaat ggagaaaaag ttgaaaattt tgtacctaac    240

gaaggttttt caacacccga taagtacatc gttataaaac gtgaaaagaa aagtatatca    300

gattctacag cagatatagc tgttatagac tcgatgaatg acaaaactta tcctggtgca    360

atacaacttg caaatagaaa tcttatagaa aacaagccta atatagtatc ttgtgaaaga    420

aagccaataa caataagtat agatttacct gggatgggtg aagaagggaa gacaactata    480

acttctccta cttattcttc tgttaaagca ggaattgatt cattgctaaa taagtggaat    540

tcacattatt cgtcaatata tagcattcca actagattta gctattcaga ttctatggtt    600

tatagtaagt ctcaattatc agctaaatta ggttgtaatt tcaaagcttt aaataaagca    660

ttggatattg attttgattc tatttataaa ggacaaaaga aagtaatgct tcttgcatat    720

aagcaaattt tttatacagt aaatgtagat gccccaaatc atccatcaga cttctttggg    780

gataaagtaa catttaatga cttagcaaaa aaaggagtta atagtaagaa tcctcctgta    840

tacgtttcaa gtgtatctta tggtagaact atttatgtaa aacttgaaac tacttctaaa    900

agtgccaatg taaaagctgc atttaaagca ctaatagaaa atcaaaatat aagcagtaat    960

tctgagtaca aaaatatttt aaatcaaagc tcatttacag ctacagtatt aggtggtgga   1020

gctaaagaac ataacaaagt aataactaaa aactttgatg aaataagaaa tataataact   1080

aacaactcag aatatagtcc tagaaatcca ggttatccta tagcatatac tacttctttt   1140

ctaaaagata atagtgttgc aacagtgaac aataaaacag attatataga gacaacctct   1200

acagaatata ctaatggaaa aattactctt gatcatagag gtgcatatgt agctaaattc   1260

aatattactt gggatgaagt aagctatgat aagaatggaa aagaaatagt agaacacaaa   1320
```

tcatgggaag gaaatgactt cggtagaaca gctcatttca atacagaatt atacctaaaa 1380
ggtaacgctc gaaatatttg cataaaagct aaagaatgca ctggtcttgc ttgggaatgg 1440
tggagaacta taatagatga taaaaatgtt cctttagtta aaaacagaaa agtctatatt 1500
tggggaacaa cattatatcc tagaacatta acagaaatag aataa 1545

<210> SEQ ID NO 30
<211> LENGTH: 1584
<212> TYPE: DNA
<213> ORGANISM: Clostridium tetani

<400> SEQUENCE: 30
ttacatttta gtttcaattg atgtctttgg atataatgtt gtaccccata tatagaaagt 60
tctttctttt gctagtggta tatttttaac atctacaatg gttctccacc attcccatgc 120
aagacctgta cattctctta tttttacaga tatatttcgt gcatttcctt ttaaatatat 180
ttctgtatta aaatgagccg ttctatctct attatttcct tcccaagctt tatgttcaac 240
tatttcattt cccttttcgt catagctaac ctcatcccat gttacttgga attgagcaac 300
atacgctcca ctatgatcaa gtactatttt accattagta tattctgttg cagttgtttc 360
tatatattct gttttattat ttacggatgc tatactattg tcttttaaaa atgtagtagt 420
atatgaaatt ggatatcctg gattttgtgg actatacact gaattatttt taataatatt 480
tcttatttca tcaaaatcct tagtgattat cttattatgt tcttgtgctc ctccccctaa 540
aacagtagct gtaaatgaac tttgatttaa tatatcctta tattctgcat tactacttat 600
atcctggtta ttgattagtg ctttaaaagc tgctttaaca tgtgaactct tagaggtagt 660
ttcaagtttt acataaattg ttctaccata tgcaacattt gaaacatatg caggaggatt 720
attattattt atccccttta aagccaattc atcaaaagtt acactatcac caaataaatc 780
tgatggacga tttggtgggt ctacacttac tgtataaaaa atttgtttgt atgcaagaag 840
cataaccttt ttttcacctt taaatatgga atcaaaatct atatttaatg ctttgtttaa 900
agctttaaaa ttgcatccaa ctgctgcaga taactgtgat tggctataca ccatagtatc 960
agaataactc attcttgtag gtatagtata tttagatgaa tactttgaat tccatgtatc 1020
taatatagaa tttattgcag aattaactga ggagtaggta ggtgaattaa caactttctt 1080
accatcttca gccatacccg gtaagtcaac acttatagta ataggttttc tctcacatga 1140
aattatatca ggtttgtttt ccataagatt tctgttagca agttgtatag ctccaggata 1200
agttctatca tttattgagt ctataattga aatgtctgct gtggaatctg aaatactctt 1260
cttctcacgt tttaccacaa tgaacttatc tggattttca aatccttcag caggtacaaa 1320
attttctacc tgttcaccat tatatgataa tatcttacgt ggatcatagg ataatccata 1380 aatattttg tctatgtcac tactgttgtc ttttgccaaa ttacattttg tatttgacgt 1440
tactacttgt ccattattga ttaatgaatg ttcctctaca tttcctttag ctaatacatt 1500
actggaatta taattagata ttaagccagt cattgaaaat attagcaatg aacgtgatac 1560
aaattttaat acatttttgt tcat 1584

<210> SEQ ID NO 31
<211> LENGTH: 1587
<212> TYPE: DNA
<213> ORGANISM: Listeria ivanovii

<400> SEQUENCE: 31

-continued

```
atgaaaaaaa taatgctact tttaatgaca ttgttactag taagtttacc gttagcacaa     60

gaagctcaag cagatgcctc agtatatagt taccaaggca taatttcaca catggcacca    120

ccagcgtctc cgcctgcaaa gcctaagacg ccggttgaaa agaaaaatgc agctcaaatc    180

gatcaatata tacaagggct ggattatgat aaaaacaata tattagtgta cgatggagaa    240

gctgttaaaa atgttccacc aaaagcagga tacaaagaag gaaatcaata tattgtagtg    300

gagaaaaaga aaaaatctat caatcaaaat aacgcagata ttcaagttat taactcgctt    360

gcaagcctta cttatccagg agctttagtg aaggcgaatt cagagttagt cgaaaatcaa    420

cccgatgtcc tccctgtgaa acgagattca gttacactta gtattgattt gcctggaatg    480

gttaaccatg acaatgaaat agtcgttcaa aatgcaacta aatccaatat aaatgacgga    540

gtgaatactt tagtagatcg ttggaataat aaatactccg aagaataccc aaatattagt    600

gcgaaaattg actatgatca agaaatggcc tatagcgaat cgcaattagt tgcaaaattt    660

ggtgcagcat ttaaagctgt taataatagt ttgaatgtaa actttggagc gattagtgaa    720

ggtaaggtgc aagaagaagt tattaatttc aaacaaattt attatactgt taatgttaat    780

gaacctacaa gcccttccag attctttggt aaaagtgtta ctaaagaaaa cttgcaagcg    840

ctgggcgtaa atgcggaaaa tccacccgca tacatctcta gtgttgcata tggtcgtgac    900

attttcgtga aattatcgac tagttcacac agcaccagag tgaaggctgc attcgatact    960

gcatttaagg gtaaatcagt taaaggtgat acagaattag aaaatattat tcaaaatgct   1020

tcatttaaag cggtgattta tggtggttca gccaaagatg aagtagaaat aattgatgga   1080

gatttaagca aattacgaga tattttaaaa caaggggcta attttgataa gaaaaatccg   1140

ggcgtaccga ttgcgtatac aactaatttc ttgaaagata atcagttagc agttgttaaa   1200

aataattcgg aatatatcga aacaacttct aaggcttact cggatggaaa aattaaccta   1260

gatcattccg gtgcctatgt tgcgagattc aatgttactt gggatgaagt tagctatgat   1320

gctaatggaa atgaagttgt tgaacataaa aaatggtccg aaaatgataa agataagtta   1380

gctcatttta cgacatcaat ctatttgcca gggaatgcaa ggaatattaa tattcatgcg   1440

aaagaatgta ctggcttggc ttgggaatgg tggagaacgg ttgtggatga tagaaacttg   1500

ccattagtaa aaaatagaaa tgtttgtatc tggggaacaa cgctttatcc agcgtatagt   1560

gatactgtag ataatccaat taagtaa                                       1587
```

<210> SEQ ID NO 32
<211> LENGTH: 1590
<212> TYPE: DNA
<213> ORGANISM: Listeria monocytogenes

<400> SEQUENCE: 32

```
atgaaaaaaa taatgctagt ttttattaca cttatattag ttagtctacc aattgcgcaa     60

caaactgaag caaaggatgc atctgcattc aataaagaaa atttaatttc atccatggca    120

ccaccagcat ctccgcctgc aagtcctaag acgccaatcg aaaagaaaca cgcggatgaa    180

atcgataagt atatacaagg attggattac aataaaaaca atgtattagt ataccacgga    240

gatgcagtga caaatgtgcc gccaagaaaa ggttataaag atggaaatga atatatcgtt    300

gtggagaaaa agaagaaatc catcaatcaa aataatgcag atatccaagt tgtgaatgca    360

atttcgagcc taacatatcc aggtgctctc gtgaaagcga attcggaatt agtagaaaat    420

caacccgatg ttcttcctgt caaacgtgat tcattaacac ttagcattga tttgccagga    480

atgactaatc aagacaataa aattgttgta aaaaatgcta ctaaatcgaa cgttaacaac    540
```

gcagtaaata cattagtgga aagatggaat gaaaaatatg ctcaagctta tccaaatgta 600
agtgcaaaaa ttgattatga tgacgaaatg gcttacagtg aatcacaatt aattgcaaaa 660
tttggtacgg catttaaagc tgtaaataat agcttgaatg taaacttcgg cgcaatcagt 720
gaagggaaaa tgcaagaaga agtcattagt tttaaacaaa tttactataa cgtgaatgtt 780
aatgaaccta caagaccttc cagatttttc ggcaaagctg ttactaaaga gcagttgcaa 840
gcgcttggag tgaatgcaga aaatcctcct gcatatatct caagtgtggc atatggccgt 900
caagtttatt tgaaattatc aactaattcc catagtacta aagtaaaagc tgcttttgac 960
gctgccgtaa gtgggaaatc tgtctcaggt gatgtagaac tgacaaatat catcaaaaat 1020
tcttccttca aagccgtaat ttacggtggc tccgcaaaag atgaagttca aatcatcgac 1080
ggtaacctcg gagacttacg agatattttg aaaaaaggtg ctacttttaa ccgggaaaca 1140
ccaggagttc ccattgccta tacaacaaac ttcttaaaag acaatgaatt agctgttatt 1200
aaaaacaact cagaatatat tgaaacaact tcaaaagctt atacagatgg aaaaatcaac 1260
atcgatcact ctggaggata cgttgctcaa ttcaacatct cttgggatga aataaattat 1320
gatcctgaag gtaacgaaat tgttcaacat aaaaactgga gcgaaaacaa taaaagtaag 1380
ctagctcatt tcacatcgtc catctatttg ccaggtaacg caagaaatat taatgtttac 1440
gctaaagaat gcactggttt agcttgggaa tggtggagaa cggtaattga tgaccggaac 1500
ctaccgcttg tgaaaaatag aaatatctcc atctggggca ctacacttta tccgaaatat 1560
agtaatagtg tagataatcc aatcgaataa 1590

<210> SEQ ID NO 33
<211> LENGTH: 1593
<212> TYPE: DNA
<213> ORGANISM: Listeria seeligeri

<400> SEQUENCE: 33
atgaaaatat ttggtttagt tatcatgtcg ttgctatttg ttagtttgcc aataacacaa 60
caacctgaag cgagggatgt ccccgcgtac gatagaagcg aggtgactat atctcctgct 120
gaaacaccag agtccccacc ggcaacacca aaaacacctg tagagaaaaa gcatgcggaa 180
gaaattaata aatatatttg gggattaaac tatgataaaa atagtattct ggtctatcaa 240
ggtgaagcag ttacaaacgt tccaccgaaa aagggctaca aagatggcag tgaatatatt 300
gtcgttgaaa aaaagaaaaa aggtatcaat caaaacaatg cagacatttc tgtcataaat 360
gcaatttcga gccttactta tcctggagcg ttggtaaaag caaatagaga attagtagaa 420
aatcaaccta atgtactacc agtaaaacga gattcactta cattaagtgt agatttacca 480
ggaatgacta aaaaagataa taaaatattc gttaaaaacc ctacaaagtc aaacgtaaat 540
aatgccgtga atacattagt agagcgttgg aatgataagt attcaaaagc gtatcctaat 600
attaatgcaa aaattgatta ttccgatgaa atggcttata gtgaatcaca attaattgcc 660
aaatttggga ctgcctttaa agctgttaat aatagtttga atgtaaattt tgaggcaatt 720
agtgatggga aagtacaaga agaagtcatt agttttaagc aaatttatta taatattaac 780
gttaatgaac ctacaagtcc ttccaaattc tttgggggta gtgttaccaa agaacaacta 840
gatgctttag gtgtaaatgc cgaaaatcct cctgcttaca tttctagtgt tgcttacggt 900
cgccaagttt atgtgaaact atcctctagc tcgcatagta acaaagttaa aactgctttc 960
gaggcggcga tgagtggcaa atcagtgaaa ggggatgtag aattaacaaa tattataaaa 1020

-continued aattcttctt ttaaagcagt catttatggt ggctcagcga aagaagaggt tgaaattatt 1080
gatggcaatt taggcgaact tcgagatatt ttgaaaaaag ggtccactta tgatagagaa 1140
aaccctggcg ttccgatctc gtacacaact aactttttga aagataatga cttagcggtt 1200
gttaaaaaca actcagaata tatcgaaaca acttcgaaat cttatacaga tggaaaaatt 1260
aatattgatc attctggtgg ttatgtagcc caattcaata tatcttggga tgaagtaagt 1320
tatgacgaga acggaaatga aataaaagtt cataagaaat ggggcgaaaa ttataagagt 1380
aagttagctc atttcacttc ttctatctat ttgccaggaa atgcgagaaa tattaacatc 1440
tatgcaagag aatgtaccgg cttgttttgg gaatggtgga gaactgttat agatgacaga 1500
aacttaccat tagtaaaaaa tagaaatgta tctatttggg gtacaacgct ttacccaaga 1560
cattctaata atgtagataa tccgattcag tag 1593

<210> SEQ ID NO 34
<211> LENGTH: 1494
<212> TYPE: DNA
<213> ORGANISM: Streptococcus suis

<400> SEQUENCE: 34
atgagaaaaa gttcgcactt gattttaagc tcaatagtca gtttggcact cgtaggggtc 60
acaccattga gtgttcttgc agattccaaa caagatatta atcagtattt tcaaagcttg 120
acttacgagc cacaagagat tcttacaaat gagggagaat acattgataa tccgccagca 180
acaactggta tgttagaaaa cggacgtttt gtagtacttc gcagagaaaa gaagaatatt 240
acgaacaata gtgcagatat tgctgttatt gatgctaagg ctgcaaatat ttatccaggt 300
gctttattgc gtgctgacca aaatcttctg gataataatc caacgcttat cagtattgcg 360
cggggagatc tgacgcttag tttgaattta cctggtttgg ccaatgggga tagccacact 420
gttgtaaatt ctccaacaag aagtactgtt cgaacagggg tgaataacct tctgtctaaa 480
tggaataata cgtatgctgg agagtatggc aatacccaag cagagcttca atatgatgaa 540
acaatggcat acagtatgtc acaattgaaa acgaagttcg gaacctcttt tgaaaaaatt 600
gctgtaccat tagatatcaa ttttgatgcc gtgaattcgg gtgaaaaaca ggttcagatt 660
gttaacttta aacaaattta ttatacagtt agtgttgatg aaccagaatc tccaagcaag 720
ctttttgcag aagggacaac tgtagaagat ttgaaacgaa atgggataac agatgaggta 780
cctcctgttt atgtttccag cgtttcttat ggacgctcta tgttcatcaa gttagaaact 840
agcagtagga gtacccaagt tcaagccgca tttaaagcag ccatcaaagg cgttgatatt 900
agtggcaatg ctgagtatca agacattctg aaaaatactt cattctctgc ttatattttt 960
ggtggggatg caggtagcgc ggctactgtt gtgagcggaa atattgaaac actgaagaag 1020
attattgaag aaggtgcaag atacggaaaa ctcaatccag gtgttccgat ttcgtattca 1080
accaactttg tcaaagacaa tagacctgct cagattttga gcaattcaga gtacatagaa 1140
acaacttcaa cagtccataa tagcagtgca ttgacattgg atcattcagg tgcttatgtt 1200
gcgaaataca acattacttg ggaagaagta tcttacaatg aagctggaga agaagtttgg 1260
gaaccaaaag cttgggataa gaatggtgta aatctgacct cacactggag tgaaaccatt 1320
caaattccag gaaatgctcg caatcttcat gtcaatattc aagaatgtac aggattagca 1380
tgggagtggt ggagaacagt ttatgacaaa gatttaccac ttgttggtca acgtaaaata 1440
accatctggg gaacaacgtt atacccacag tatgcggatg aggtgataga gtaa 1494

-continued

<210> SEQ ID NO 35
<211> LENGTH: 1398
<212> TYPE: DNA
<213> ORGANISM: Streptococcus mitis

<400> SEQUENCE: 35
atggcaaata aagcagtaaa tgactttata ctagctatgg attacgataa aaagaaactc 60
ttgacccatc agggagaaag tattgaaaat cgtttcatca aagaggggaa tcagctaccc 120
gatgagtttg ttgttatcga aagaaagaag cggagcctgt cgacaaatac aagtgatatt 180
tctgtgacag ctaccaacga cagtcgcctc tatcctggag cacttctcgt agtggatgag 240
accttgttag agaataatcc cactcttctt gcggtcgatc gtgctccgat gacttatagt 300
attgatttgc ctggtttggc aagtagtgat agctttctcc aagtagaaga tcccagcaat 360
tcaagtgttc gcggagcggt aaacgatttg ttggctaagt ggcatcaaga ttatggtcag 420
gtcaataatg tcccagctag aatgcagtat gaaaaaatca cggctcacag catggaacaa 480
ctcaaggtca agtttggttc tgactttgaa aagacaggga attctcttga tattgatttt 540
aactctgtcc attcgggcga aaagcagatt cagattgtta attttaagca gatttattat 600
acagtcagcg tagatgctgt taaaaatcca ggagatgtat ttcaagatac tgtaacggta 660
gaggatttga ggcagagagg aatttctgcc gatcgtcctt tggtctatat ttcgagtgtt 720
gcttatgggc gccaggttta tctcaagttg gagaccacga gtaagagtga tgaagtcgag 780
gctgcttttg aagctttgat aaaaggagtc aaggtagctc ctcagacaga gtggaagcag 840
attttggaca atacagaagt gaaggcggtt attttagggg gcgacccgag ttcgggtgcc 900
cgagttgtaa caggcaaggt ggatatggta gaggacttga ttcaagaagg cagtcgcttt 960
acagccgatc atccaggttt gccgatttct tatacaactt ctttttacg ggacaatgta 1020 gttgcgacct ttcaaaacag tacagactat gttgagacta aggtgacagc ctacagaaac 1080
ggagatttac tgctggatca tagtggtgcc tatgttgctc aatattacat tacttgggat 1140
gaattatcct atgattatca aggtaaggaa gttttgactc ctaaggcttg gaacagaaat 1200
gggcaggatt tgacggctca ttttaccact agtattcctt taaaagggaa tgttcgcaat 1260
ctctctgtca aaattagaga gtgtaccgga cttgcctggg aatggtggcg tacggtttat 1320
gaaaaaaacg atttgcccct agtgcgtaag cggacgattt ctatttgggg aacgactctt 1380
tatcctcagg tagaggat 1398

<210> SEQ ID NO 36
<211> LENGTH: 1599
<212> TYPE: DNA
<213> ORGANISM: Streptococcus intermedius

<400> SEQUENCE: 36
atgaaaacta agcagaatat tgctcgcaaa ttgtcaagag ttgttttatt aagcactctc 60
gttctctctt cggcagcacc gatttcagct gcattcgctg aaacacctac caaaccaaaa 120
gcagctcaaa cagagaaaaa acccgaaaag aaaccggaaa acagcaactc tgaagctgca 180
aaaaaagctc tgaatgatta tatttgggga ttgcagtatg ataaactaaa cattttaaca 240
caccaaggtg aaaaattgaa aaaccactct agccgcgagg catttcatcg cccaggtgag 300
tatgttgtta tcgaaaagaa aaaacaaagc atttcaaacg caacatctaa gttatctgta 360
agttcagcaa atgatgaccg catcttccca ggtgcattgc taaaagcgga ccaaagtttg 420
ttagaaaatc ttccaaccct aatcccagtt aatcgcggca aaacaactat tagtgtaaac 480

-continued

```
ttaccgggat tgaaaaatgg cgaaagtaat cttacagttg aaaatccatc caacagtaca    540

gttcgaacag ctgttaacaa tttagttgaa aaatggattc aaaaatactc taaaactcat    600

gctgtgccag ctagaatgca atatgaatct attagcgccc aaagcatgag ccaattacaa    660

gcaaaatttg gtgctgattt ctcaaaagtc ggtgcaccac ttaatgttga cttctcatct    720

gttcacaaag gtgaaaaaca agtatttatt gcgaacttta gacaagttta ctacacagct    780

agcgtagact ctccaaatag tccttctgca ctctttggct ctggtatcac accaactgat    840

ttaatcaatc gtggagttaa ttctaaaacc ccaccagttt atgtttcaaa tgtatcatat    900

ggccgtgcaa tgtatgtgaa atttgaaact acaagcaaga gtacaaaagt acaagccgct    960

attgatgctg ttgttaaagg agcaaaactt aaagctggaa cagaatatga aaatattcta   1020

aaaaatacta aaatcactgc tgttgttctc ggtggtaacc caggtgaagc ttctaaagtc   1080

atcacaggta atattgatac tttgaaagat ttgatccaaa aaggtagcaa tttcagtgct   1140

caaagtccag ctgtaccaat ctcttacact acttcttttg taaaagacaa ttctattgca   1200

actatccaaa acaacacaga ctacatcgaa acaaaagtaa catcctataa agatggtgct   1260

ctcaccctca atcatgatgg tgctttcgtt gcacgcttct atgtttattg ggaagaactc   1320

ggacatgatg ctgatggcta cgaaactatt cgctcaagat cttggagtgg aaatggctac   1380

aatcgcggtg cacactattc tacaactctc cgtttcaagg gaaatgttag aaacattcgc   1440

gtaaaagtac taggagccac tggactagct tgggagcctt ggagactgat ctatagcaag   1500

aacgatcttc ctttggttcc acaaagaaac attagcactt ggggaacaac ccttcatcca   1560

cagtttgaag ataaagttgt gaaagataac actgattaa                          1599
```

<210> SEQ ID NO 37
<211> LENGTH: 1998
<212> TYPE: DNA
<213> ORGANISM: Streptococcus mitis

<400> SEQUENCE: 37

```
atgaatcaag aaaaacgttt gcatcgcttt gtcaaaaagt gtggactcgg tgtgtgtagt     60

gctgttgttg cggccttttt attgaacgct cagggagtag ctttggctac agagcaaggg    120

aatcgtccag ttgagaccga aaacatcgct cgtggaaaac aagctagtca aagttctact    180

gcttatggag gagctgctgc acgagcagtg gacggtaatg ttgacagtga ctatgggcac    240

cattctgtaa cgcacacaaa ctttgaagac aatgcttggt ggcaagttga tcttggaaaa    300

acagagaatg ttggaaaagt taaactctac aatcgtggag atgggaatgt agctaatcgt    360

ctttccaatt ttgatgttgt tttgttaaat gaagcaaaac aagaagttgc tcgtcaacac    420

tttgatagtt tgaatgggaa ggcagaactt gaagtttttct tcaccgccaa agccgctcgt    480

tatgtaaaag tggagttgaa aactaaaaat accccattga gcttggcaga agtggaagta    540

ttccgttcag caacaactca agttggacag gatagaactg caccagtagt agatcaaaca    600

tcagcattga aagactacct tttggctta gcttataatc ctttggatat tttaactcgc    660

aagggagaaa ccttagaaaa tcgctacaac acaagtgcta aggaacaaaa tggagagttt    720

gtcgttgtag aaaaaatcaa gaaaaccctc tctacaggca cagcagatgt ttccatcaat    780

ggaaatcaaa atgtcttcct aggtggcttg tataaggcaa accaaaatct gctagaaaat    840

cagccagaat tgattagtct tgcccgtgca aaggggacag tcagcgtcga tttacctggt    900

atgattcagt ctgacagccg aattgaagca gatcctacaa ctagtggtat gcagtctgcg    960

atgaatacct tggttgaaag atggacaaag aattactcat ctagccattc cgttcctgcc   1020
```

```
cgtgttcagt atgaatcaac tacagcctat agcatgaatc aattgaaagc aaaatttggt   1080

gcagactttg aaaaagcagg tgcaccgctc aagattgact ttgaggctgt gcaaaagggt   1140

gaaaagcaaa ttgaagttgt aaactttaaa caaatctact atacagcgac atttgatgca   1200

ccgaccaatc cagcggctgt atttgacaag agtgtgacac ctgaagattt aaaacaaaga   1260

ggcgttgatt cacaaactcc acctgtatat gtatcaaatg tttcttacgg acgtcaaatc   1320

tatgttaagt ttgagtcagc aagtaagtct actgaattaa aagcagctat taatgcggtt   1380

atcaaaggcg caacaattgc tccaaattct gaatggagcc gtctattgaa gaatacttct   1440

gtaacagcgg taattgtagg aggtaatgct agcggtgccg ccaaagttgt cacaggaaca   1500

gtcgaaaact tgaaggaact catcagagaa ggagctaact ttagcgctca aagtccagct   1560

gtgccaatct catataagac tgccttccta aaagataatg cccaagcaac tttacaaaat   1620

agtacagact atatcgaaac gaaggttact tcttacaaaa atggtttctt gaaacttcat   1680

cataagggtg cttatgttgc gcgttactac atctattggg atgaaattac atatgatgaa   1740

caaggaaatc cagaaatccg ttcacgtcaa tgggaagata acggaaaaaa cagaacttca   1800

ggcttccaaa cagagattca atttagagga aatgtccgta atcttcgcat caaggttcaa   1860

gaaaagacgg gtcttgtatg ggaaccatgg cgtacagttt acaaccgcac agacttacca   1920

ctagtacaac agcgtacaat tacacattgg ggaacaactc taaaccctaa agttgatgaa   1980

aaaattgtga atgagtaa                                                  1998
```

```
<210> SEQ ID NO 38
<211> LENGTH: 1605
<212> TYPE: DNA
<213> ORGANISM: Arcanobacterium pyogenes

<400> SEQUENCE: 38

atgaaacgaa aggcttttgc atcgctagtg gcgagtgtag tcgcagcagc aactgtcacg     60

atgcccacag catcttttgc tgccggattg ggaaacagct cgggattgac ggacggcttg    120

tcagcgccgc gagcctccat ctccccgacg gataaagttg accttaagtc ggcgcaagag    180

accgacgaga cgggcgtcga taagtacatt cgtggtctga aatacgatcc ctctggtgta    240

cttgcagtca agggtgagtc tattgaaaat gtgccggtta ccaaggatca gctcaaggac    300

ggcacctaca cggtatttaa gcatgaacgc aagagtttta acaatttgcg ttcggacatc    360

tctgcgttcg atgcgaacaa cgcccacgtc tatcctggcg cgctcgtgtt agcaaataaa    420

gatcttgcaa aggtagtcc gacttcgatc ggaattgcac gtgctccgca aactgtcagc    480

gtcgacttgc caggattagt tgacggtaag aataaggtcg tcatcaacaa tcccacgaag    540

agttccgtga ctcaaggact gaacggcctt ctcgacggtt ggattcagcg caatagcaag    600

tatcctgacc atgctgcaaa gatctcctac gatgagacta tggtgacgtc aaagcgtcaa    660

ctggaggcaa agcttggcct cggatttgaa aaggtctcag ccaagctcaa cgtggacttc    720

gatgcaattc ataagcgtga acggcaggtg gctatcgctt ccttcaaaca gatttactac    780

acggctagcg tagatacacc gacatctcca catagcgttt tcggcccgaa tgtcaccgca    840

caggatttga aagatcgggg agtcaataac aagaatcctc taggatacat ttcgtcggtc    900

agctatggac gccagatttt tgtcaagctg gaaacgacct cgacttccaa tgatgtacaa    960

gcggctttta gcggcctgtt caaagctaag ttcggcaatc tttccacaga gttcaaggct   1020

aagtatgccg atatcctgaa caagacccga gctactgtgt acgctgttgg tggcagcgct   1080
```

```
agaggcggag ttgaagttgc aactggcaat atcgatgcac tcaagaagat catcaaggag   1140

gaaagcacct actctacgaa ggttcctgcc gtgcccgttt cctatgccgt caatttcttg   1200

aaggataatc agttggcagc tgttaggagc agcggtgatt acattgaaac cactgcaacg   1260

acttacaagt ctggtgagat caccttccgc catggcggtg gctacgtcgc aaagttcagg   1320

ctgaagtggg acgagatcag ctacgacccg cagggcaagg aaatccgtac acccaagacg   1380

tggagcggga attgggcagc ccgcaccctt ggcttccgtg agactattca acttccagca   1440

aacgcgcgca acatccatgt ggaagcaggc gaggcaactg gcctagcgtg ggatccgtgg   1500

tggaccgtta tcaataagaa gaatctcccc ttggtgccac atcgagagat cgtccttaag   1560

ggcacgacgc tcaatccctg ggtcgaggac aatgtcaaat cctag                    1605


<210> SEQ ID NO 39
<211> LENGTH: 11
<212> TYPE: PRT
<213> ORGANISM: Streptococcus pneumoniae

<400> SEQUENCE: 39

Glu Cys Thr Gly Leu Ala Trp Glu Trp Trp Arg
1               5                   10


<210> SEQ ID NO 40
<211> LENGTH: 471
<212> TYPE: PRT
<213> ORGANISM: Streptococcus pneumoniae

<400> SEQUENCE: 40

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220
```

-continued

```
Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Ser Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Asp Tyr Pro Gln Val
    450                 455                 460

Glu Asp Lys Val Glu Asn Asp
465                 470
```